(12) United States Patent
Hatakeyama et al.

(10) Patent No.: US 10,695,554 B2
(45) Date of Patent: *Jun. 30, 2020

(54) BIO-ELECTRODE COMPOSITION, BIO-ELECTRODE, METHOD FOR MANUFACTURING THE BIO-ELECTRODE, AND POLYMER

(71) Applicant: SHIN-ETSU CHEMICAL CO., LTD., Tokyo (JP)

(72) Inventors: Jun Hatakeyama, Joetsu (JP); Motoaki Iwabuchi, Joetsu (JP); Osamu Watanabe, Joetsu (JP); Takayuki Fujiwara, Joetsu (JP); Yasuyoshi Kuroda, Annaka (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/882,406

(22) Filed: Jan. 29, 2018

(65) Prior Publication Data

US 2018/0229023 A1 Aug. 16, 2018

(30) Foreign Application Priority Data

Feb. 14, 2017 (JP) ................. 2017-024652

(51) Int. Cl.
*A61N 1/04* (2006.01)
*A61B 5/0478* (2006.01)
(Continued)

(52) U.S. Cl.
CPC .......... *A61N 1/0496* (2013.01); *A61B 5/0408* (2013.01); *A61B 5/0448* (2013.01);
(Continued)

(58) Field of Classification Search
CPC .................. H01M 10/0565; B01J 31/0215
(Continued)

(56) References Cited

U.S. PATENT DOCUMENTS

| | | |
|---|---|---|
| 5,536,446 A | 7/1996 | Uy et al. |
| 5,981,680 A | 11/1999 | Petroff et al. |

(Continued)

FOREIGN PATENT DOCUMENTS

| | | |
|---|---|---|
| JP | H05-095924 A | 4/1993 |
| JP | 2002-332305 A | 11/2002 |

(Continued)

OTHER PUBLICATIONS

May 25, 2018 Extended Search Report issued in European Patent Application No. 18156224.0.

*Primary Examiner* — Khanh T Nguyen
(74) *Attorney, Agent, or Firm* — Oliff PLC

(57) ABSTRACT

The present invention provides a bio-electrode composition capable of forming a living body contact layer for a bio-electrode that is excellent in conductivity and biocompatibility, is light-weight, can be manufactured at low cost, and can control significant reduction in conductivity even though the bio-electrode is soaked in water or dried. The present invention is accomplished by a bio-electrode composition including an (A) ionic material and a (B) resin other than the component (A), in which the component (A) has both a repeating unit "a" of a lithium salt, a sodium salt, a potassium salt, or an ammonium salt of sulfonamide including a partial structure represented by the following general formula (1) and a repeating unit "b" having a silicon atom,

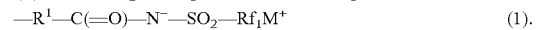
—R¹—C(=O)—N⁻—SO₂—Rf₁M⁺ (1).

14 Claims, 4 Drawing Sheets

(51) Int. Cl.

| | |
|---|---|
| *C08F 220/58* | (2006.01) |
| *A61B 5/0408* | (2006.01) |
| *A61B 5/0448* | (2006.01) |
| *A61B 5/0492* | (2006.01) |
| *C08L 33/26* | (2006.01) |
| *C08L 43/04* | (2006.01) |
| *C08F 230/08* | (2006.01) |
| *A61B 5/053* | (2006.01) |
| *C08G 69/42* | (2006.01) |
| *C08G 77/00* | (2006.01) |
| *C08F 220/60* | (2006.01) |

(52) U.S. Cl.
CPC .......... *A61B 5/0478* (2013.01); *A61B 5/0492* (2013.01); *A61B 5/0537* (2013.01); *C08F 220/58* (2013.01); *C08F 230/08* (2013.01); *C08G 69/42* (2013.01); *C08G 77/00* (2013.01); *C08L 33/26* (2013.01); *C08L 43/04* (2013.01); *A61B 2562/125* (2013.01); *A61B 2562/14* (2013.01); *C08F 220/606* (2020.02)

(58) Field of Classification Search
USPC .................................................. 429/303, 314
See application file for complete search history.

(56) References Cited

U.S. PATENT DOCUMENTS

| | | | |
|---|---|---|---|
| 2002/0009650 A1* | 1/2002 | Michot | ................ B01J 31/0215 429/314 |
| 2002/0177039 A1 | 11/2002 | Lu et al. | |
| 2002/0188069 A1 | 12/2002 | Sugo et al. | |
| 2008/0118860 A1 | 5/2008 | Harada et al. | |
| 2009/0061358 A1 | 3/2009 | Ohashi et al. | |
| 2011/0087315 A1 | 4/2011 | Richardson-Burns et al. | |
| 2015/0275060 A1 | 10/2015 | Kuroda et al. | |
| 2016/0155530 A1 | 6/2016 | Someya et al. | |
| 2016/0190641 A1* | 6/2016 | Lee | ................... H01M 10/0565 429/303 |
| 2016/0336618 A1 | 11/2016 | Lee et al. | |

FOREIGN PATENT DOCUMENTS

| | | | | |
|---|---|---|---|---|
| JP | 2003-064259 | * | 3/2003 | ............. C08L 83/06 |
| JP | 2003-225217 A | | 8/2003 | |
| JP | 2004-033468 A | | 2/2004 | |
| JP | 2004-527902 A | | 9/2004 | |
| JP | 2005-320418 A | | 11/2005 | |
| JP | 2008-111103 A | | 5/2008 | |
| JP | 2009-080474 A | | 4/2009 | |
| JP | 2011-079946 A | | 4/2011 | |
| JP | 2015-019806 A | | 2/2015 | |
| JP | 2015-100673 A | | 6/2015 | |
| JP | 2015-193803 A | | 11/2015 | |
| JP | 2016-011338 A | | 1/2016 | |
| JP | 2016-065238 A | | 4/2016 | |
| WO | 2013/039151 A1 | | 3/2013 | |

* cited by examiner (a)

(b)

TO THE IMPEDANCE
MEASUREMENT APPARATUS

BIO-ELECTRODE COMPOSITION, BIO-ELECTRODE, METHOD FOR MANUFACTURING THE BIO-ELECTRODE, AND POLYMER

TECHNICAL FIELD

The present invention relates to a bio-electrode that is used in contact with the skin of a living body capable of detecting physical conditions such as heart rate by an electric signal transmitted from the skin, a method for manufacturing the bio-electrode, a bio-electrode composition desirably used in the bio-electrode, and a polymer desirably used in the bio-electrode composition.

BACKGROUND

A recent growing popularity of Internet of Things (IoT) has accelerated the development of such major wearable devices as watches and glasses that allow for Internet access. Even in the fields of medicine and sports, wearable devices for constantly monitoring the user's physical state are increasingly demanded, and such technological development is expected to be further encouraged.

In the field of medicine, including an electrocardiogram for detecting an electric signal to measure the motion of the heart, use of wearable devices for monitoring the state of human organs by detecting extremely weak current has been examined. The electrocardiogram measurement is conducted by attaching an electrode coated with a conductive paste to a body, but this is a single (not continuous), short-time measurement. On the other hand, the above medical wearable device is aimed at monitoring the state of physical conditions for a few weeks. Accordingly, a bio-electrode used in a medical wearable device is required to make no changes in conductivity even in long-time use and cause no skin allergy. In addition to these, bio-electrodes must be light-weight and produced at low cost.

Medical wearable devices are classified into two types: direct body attachment and clothing attachment. One typical body attachment device is a bio-electrode formed of a hydrophilic gel containing water and electrolytes as ingredients of the above conductive paste (Patent Document 1). The hydrophilic gel, containing sodium, potassium, and calcium electrolytes in a hydrophilic polymer containing water, detects changes in ion concentration from the skin to convert the data into electricity. Meanwhile, one typical clothing attachment device is characterized by a method for using as an electrode a fabric including a conductive polymer, such as PEDOT-PSS (Poly-3,4-ethylenedioxythiophene-polystyrenesulfonate), and a silver paste incorporated into the fiber (Patent Document 2).

However, the use of the hydrophilic gel containing water and electrolytes unfortunately brings about loss of conductivity due to water evaporation in drying process. Meanwhile, the use of a higher ionization tendency metal such as copper can cause some users to suffer from skin allergy, as well as a conductive polymer such as PEDOT-PSS due to strong acidity.

By taking advantage of excellent conductivity, the use of electrode materials formed of metal nanowire, carbon black, or carbon nanotube has been examined (Patent Documents 3, 4, and 5). With higher contact probability, metal nanowires can conduct electricity in small quantities to be added. Nevertheless, metal nanowires, formed of a pointed thin material, may cause skin allergy. Likewise, carbon nanotubes can stimulate a living body. Although the carbon black is not as poisonous as carbon nanotube, it also stimulates the skin. Accordingly, even though these electrode materials themselves cause no allergic reaction, the biocompatibility can be degraded depending on the shape of a material and its inherent stimulation, thereby failing to satisfy both conductivity and biocompatibility.

Although metal films seem to function as an excellent bio-electrode thanks to extremely high conductivity, this is not always the case. Upon heartbeat, the human skin releases a sodium ion, a potassium ion, or a calcium ion, instead of extremely weak current. It is thus necessary to convert changes in ion concentration into current, which is what less ionized precious metals unfortunately fail to do efficiently. The resulting bio-electrode including the precious metal is characterized by high impedance and high resistance to the skin during electrical conduction.

Meanwhile, the use of a battery containing an ionic liquid has been examined (Patent Document 6). Advantageously, the ionic liquid is thermally and chemically stable, and the conductivity is excellent, providing more various battery applications. However, an ionic liquid having smaller molecular weight shown in Patent Document 6 unfortunately dissolves into water. A bio-electrode containing such an ionic liquid in use allows the ionic liquid to be extracted from the electrode by sweating, which not only lowers the conductivity, but also causes rough skin by the liquid soaking into the skin.

In addition, any bio-electrode fails to get biological information when it is apart from the skin. The detection of even changes in contact area can vary quantities of electricity traveling through the electrode, allowing the baseline of an electrocardiogram (electric signal) to fluctuate. Accordingly, in order to stably detect electric signals from the body, the bio-electrode is required to be in constant contact with the skin and make no changes in contact area. This requirement is satisfied, preferably by use of adhesive bio-electrodes. Moreover, elastic and flexible bio-electrodes are needed to follow changes in skin expansion and flexion.

PRIOR ART DOCUMENTS

Patent Documents

Patent Document 1: International Patent Laid-Open Publication No. WO 2013/039151
Patent Document 2: Japanese Unexamined Patent publication (Kokai) No. 2015-100673
Patent Document 3: Japanese Unexamined Patent publication (Kokai) No. H5-095924
Patent Document 4: Japanese Unexamined Patent publication (Kokai) No. 2003-225217
Patent Document 5: Japanese Unexamined Patent publication (Kokai) No. 2015-019806
Patent Document 6: Japanese Unexamined Patent publication (Kokai) No. 2004-527902

SUMMARY OF THE INVENTION

Problem to be Solved by the Invention

The present invention was made in view of the situation to solve the problems, and has an object to provide a bio-electrode composition capable of forming a living body contact layer for a bio-electrode that is excellent in conductivity and biocompatibility, is light-weight, can be manufactured at low cost, and can control significant reduction in conductivity even though the bio-electrode is soaked in water or dried, a bio-electrode including a living body contact layer formed of the bio-electrode composition, a method for manufacturing the bio-electrode, and a polymer desirably used in the bio-electrode composition.

Means for Solving the Problem

To solve these problems, the present invention provides a bio-electrode composition including an (A) ionic material and a (B) resin other than the component (A), wherein the component (A) has both a repeating unit "a" of a lithium salt, a sodium salt, a potassium salt, or an ammonium salt of sulfonamide having a partial structure represented by the following general formula (1) and a repeating unit "b" having a silicon atom,

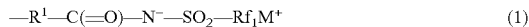

wherein, $R^1$ represents a single bond, or a linear, a branched, or a cyclic divalent hydrocarbon group having 1 to 40 carbon atoms, which may be substituted by a heteroatom, or mediated by a heteroatom; $Rf_1$ represents a linear or a branched alkyl group or a phenyl group having 1 to 4 carbon atoms, having one or more fluorine atoms or a trifluoromethyl group; and $M^+$ represents any of a lithium ion, a sodium ion, a potassium ion, or an ammonium ion.

The bio-electrode composition thus obtained can include a living body contact layer for a bio-electrode that is excellent in conductivity and biocompatibility, is lightweight, can be produced at low cost, and can control significant reduction in conductivity even though the bio-electrode is soaked in water or dried.

Also, the component (A) is preferably a polymer including repeating units "a1" and "b1" represented by the following general formula (2) as the repeating units "a" and "b", respectively,

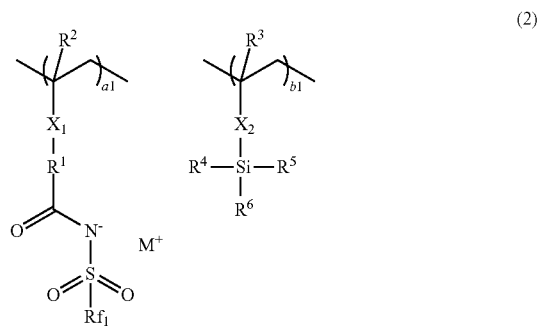

wherein, $R^1$, $Rf_1$, and $M^+$ represent the same meanings as before; each of $R^2$ and $R^3$ independently represents a hydrogen atom or a methyl group; $X_1$ represents any of a single bond, a phenylene group, a naphthylene group, an ether group, an ester group, or an amide group; $X_2$ represents any of an arylene group having 6 to 12 carbon atoms, a —C(=O)—O—$R^7$— group, or a —C(=O)—NH—$R^7$— group; $R^7$ represents any of a single bond, a linear, a branched, or a cyclic alkylene group, or a phenylene group having 2 to 12 carbon atoms, and may include one or more groups selected from an ether group, a carbonyl group, an ester group, and an amide group; each of $R^4$, $R^5$, and $R^6$ independently represents a linear, a branched, or a cyclic alkyl group having 1 to 6 carbon atoms, or an aryl group having 6 to 10 carbon atoms, and may include one or more selected from a siloxane bond, a silicon atom, and a halogen atom; $R^4$ and $R^5$, or $R^4$, $R^5$, and $R^6$ may be bonded to form a ring or a three-dimensional structure; and "a1" and "b1" are numbers satisfying the equations 0<a1<1.0, 0<b1<1.0.

The bio-electrode composition including such a component (A) can form a living body contact layer that is more excellent in conductivity and biocompatibility. Copolymerization of a repeating unit "b1" containing a silicon atom can improve the water repellency, and a dry electrode film including the polymer that is brought in contact with the skin is less affected by sweating or moisture.

In addition, the component (A) is preferably a polymer including a repeating unit "d" represented by the following general formula (2)', in addition to the repeating units "a" and "b",

wherein, $R^8$ represents a hydrogen atom or a methyl group; $X_3$ represents any of a single bond, a phenylene group, a naphthylene group, an ether group, an ester group, a phenylene group having an ester group, or an amide group; $R^9$ represents a linear or a branched alkylene group having 1 to 80 carbon atoms, having at least one ether group, and may include an aromatic group; and "d" is a number satisfying the equation 0≤d<1.0.

The component (A) including such a repeating unit "d" having an ether chain, can form a bio-electrode film having improved ion conductivity and higher precision.

The component (A) preferably includes an ammonium ion represented by the following general formula (3) as the $M^+$,

wherein, each of $R^{101d}$, $R^{101e}$, $R^{101f}$, and $R^{101g}$ independently represents any of a hydrogen atom, a linear, a branched, or a cyclic alkyl group having 1 to 12 carbon atoms, a linear, a branched, or a cyclic alkenyl group or an alkynyl group having 2 to 12 carbon atoms, or an aromatic group having 4 to 20 carbon atoms, and may include one or more selected from an ether group, a carbonyl group, an ester group, a hydroxy group, an amino group, a nitro group, a sulfonyl group, a sulfinyl group, a halogen atom, and a sulfur atom; $R^{101d}$ and $R^{101e}$, or $R^{101d}$, $R^{101e}$, and $R^{101f}$ may form a ring together with a nitrogen atom bonded thereto, and in this case, $R^{101d}$ and $R^{101e}$, or $R^{101d}$, $R^{101e}$, and $R^{101f}$ represent an alkylene group having 3 to 10 carbon atoms, or form a heteroaromatic ring having a nitrogen atom in the formula in the ring.

The bio-electrode composition including such a component (A) can form a living body contact layer that is more excellent in conductivity and biocompatibility.

In addition, the component (B) preferably includes a silicone resin having a $R_xSiO_{(4-x)/2}$ unit, wherein R represents a substituted or an unsubstituted monovalent hydrocarbon group having 1 to 10 carbon atoms, and x represents a number of 2.5 to 3.5, and a $SiO_2$ unit, diorganosiloxane having an alkenyl group, and organohydrogen polysiloxane having a SiH group.

The bio-electrode composition including such a component (B) can form a living body contact layer that is particularly favorable in compatibility of the component (A) and the component (B), adhesion to a conductive substrate, adhesion to the skin, elasticity, and water repellency.

Preferably, the bio-electrode composition further includes an organic solvent.

Such an organic solvent can further improve the application of a bio-electrode composition.

Preferably, the bio-electrode composition further includes a carbon material.

Such a bio-electrode composition can form a living body contact layer that is more excellent in conductivity.

Preferably, the carbon material is formed of carbon black and/or carbon nanotube.

Such a carbon material can particularly desirably be used in the bio-electrode composition of the present invention.

The present invention provides a bio-electrode including a conductive substrate and a living body contact layer formed on the conductive substrate, wherein the living body contact layer is a cured product of the bio-electrode composition.

The bio-electrode thus obtained can form a living body contact layer that is excellent in conductivity and biocompatibility, is light-weight, can be manufactured at low cost, and can control significant reduction in conductivity even though the bio-electrode is soaked in water or dried.

Preferably, the conductive substrate includes one or more substances selected from gold, silver, silver chloride, platinum, aluminum, magnesium, tin, tungsten, iron, copper, nickel, stainless, chromium, titanium, and carbon.

Such a conductive substrate can particularly desirably be used in the bio-electrode of the present invention.

The present invention provides a method for manufacturing a bio-electrode including a conductive substrate and a living body contact layer formed on the conductive substrate, including: applying the bio-electrode composition to the conductive substrate to be cured to form the living body contact layer.

The manufacturing method thus obtained can readily manufacture at low cost a bio-electrode including a living body contact layer that is excellent in conductivity and biocompatibility, is light-weight, and controls significant reduction in conductivity even though the bio-electrode is soaked in water or dried.

Preferably, the conductive substrate includes one or more substances selected from gold, silver, silver chloride, platinum, aluminum, magnesium, tin, tungsten, iron, copper, nickel, stainless, chromium, titanium, and carbon.

Such a conductive substrate can particularly desirably be used in the method for manufacturing a bio-electrode of the present invention.

The present invention provides a polymer including repeating units "a1" and "b1" represented by the following general formula (2),

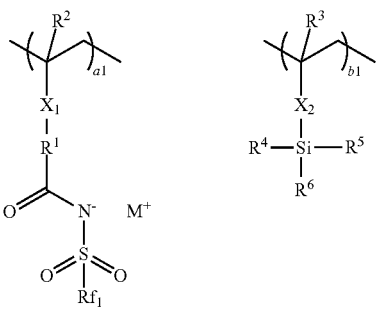

wherein, $R^1$ represents a single bond, or a linear, a branched, or a cyclic divalent hydrocarbon group having 1 to 40 carbon atoms, which may be substituted by a heteroatom, or mediated by a heteroatom; $Rf_1$ represents a linear or a branched alkyl group or a phenyl group having 1 to 4 carbon atoms, having one or more fluorine atoms or a trifluoromethyl group; $M^+$ represents any of a lithium ion, a sodium ion, a potassium ion, or an ammonium ion; each of $R^2$ and $R^3$ independently represents a hydrogen atom or a methyl group; $X_1$ represents any of a single bond, a phenylene group, a naphthylene group, an ether group, an ester group, or an amide group; $X_2$ represents any of an arylene group having 6 to 12 carbon atoms, a —C(=O)—O—$R^7$— group, or a —C(=O)—NH—$R^7$— group; $R^7$ represents any of a single bond, a linear, a branched, or a cyclic alkylene group, or a phenylene group having 2 to 12 carbon atoms, and may include one or more groups selected from an ether group, a carbonyl group, an ester group, and an amide group; each of $R^4$, $R^5$, and $R^6$ independently represents a linear, a branched, or a cyclic alkyl group having 1 to 6 carbon atoms, or an aryl group having 6 to 10 carbon atoms, and may include one or more selected from a siloxane bond, a silicon atom, and a halogen atom; $R^4$ and $R^5$, or $R^4$, $R^5$, and $R^6$ may be bonded to form a ring or a three-dimensional structure; "a1" and "b1" are numbers satisfying the equations 0<a1<1.0, 0<b1<1.0.

Such a polymer can desirably be used in a bio-electrode composition capable of forming a living body contact layer for a bio-electrode that is excellent in conductivity and biocompatibility, is light-weight, can be manufactured at low cost, and can control significant reduction in conductivity even though the bio-electrode is soaked in water or dried.

Preferably, the polymer includes, in addition to the repeating units "a1" and "b1" a repeating unit "d" represented by the following general formula (2)′,

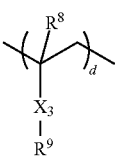

wherein, $R^8$ represents a hydrogen atom or a methyl group; $X_3$ represents any of a single bond, a phenylene group, a naphthylene group, an ether group, an ester group, a phenylene group having an ester group, or an amide group; $R^9$ represents a linear or a branched alkylene group having 1 to 80 carbon atoms, having at least one ether group, and may include an aromatic group; d is a number satisfying the equation 0≤d<1.0.

The component (A) including such a repeating unit "d" having an ether chain, can form a bio-electrode film with improved ion conductivity and higher precision.

Effect of the Invention

As described above, the bio-electrode composition of the present invention can form a living body contact layer for a bio-electrode that is capable of efficiently transmitting electric signals from the skin to a device (or that is excellent in conductivity), generating no allergy despite its long-time attachment to the skin (or that is excellent in biocompatibility), is light-weight, can be manufactured at low cost, and can control significant reduction in conductivity even though the bio-electrode is soaked in water or dried. Also, the addition of a carbon material can further improve the conductivity, and a combined use of adhesive and elastic polymers can manufacture particularly adhesive and elastic bio-electrodes. Furthermore, the use of additives can improve the elasticity and adhesion to the skin. The resin constituent and the thickness of a living body contact layer can be adjusted as required to control the elasticity and adhesion. Accordingly, a bio-electrode including a living body contact layer using such a bio-electrode composition of the present invention is particularly desirable as a bio-electrode used in medical wearable devices. The method for manufacturing a bio-electrode of the present invention can readily manufacture such a bio-electrode at low cost. In addition, the polymer of the present invention can desirably be used in the bio-electrode composition.

DESCRIPTION OF THE PREFERRED EMBODIMENTS

Figure 1:
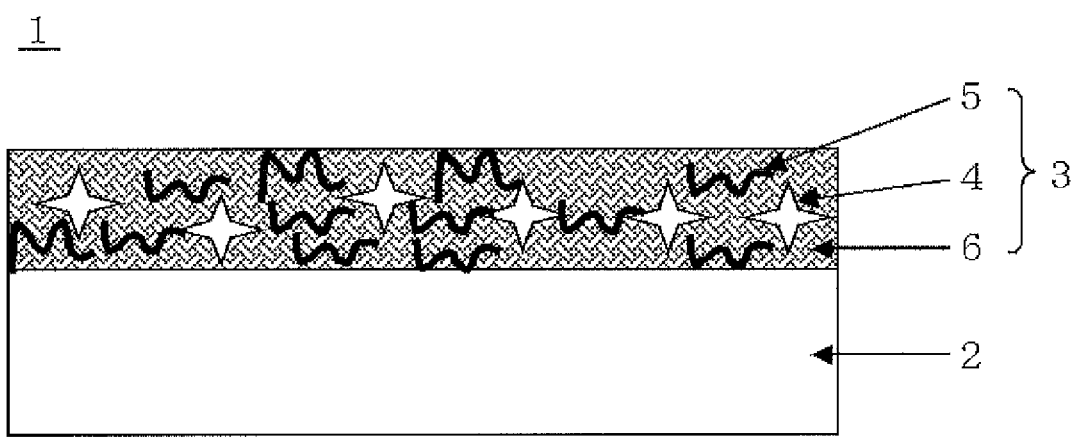
FIG. 1 is a schematic cross-sectional view showing one example of a bio-electrode of the present invention.

As described above, the development of a bio-electrode composition capable of forming a living body contact layer for a bio-electrode that is excellent in conductivity and biocompatibility, is light-weight, can be manufactured at low cost, and can control significant reduction in conductivity even though the bio-electrode is soaked in water or dried, a bio-electrode including a living body contact layer formed of the bio-electrode composition, a method for manufacturing the bio-electrode, and a polymer desirably used in the bio-electrode composition, is demanded.

Inventors of the present invention have focused on an ionic liquid as an ionic material (conductive material) to be blended into a bio-electrode composition for forming a living body contact layer for a bio-electrode. Advantageously, the ionic liquid is thermally and chemically stable, and the conductivity is excellent, providing more various battery applications. Illustrative example of the ionic liquid includes hydrochloride, oxalate, iodate, trifluoromethane sulfonate, nonafluorobutanesulfonate salt, bis(trifluoromethane sulfonyl) imide acid salt, hexafluorophosphate salt, and tetrafluoroborate salt of sulfonium, phosphonium, ammonium, morpholinium, pyridinium, pyrrolidinium, and imidazolium. However, since these salts (those having smaller molecular weight, in particular) are normally highly hydrophilic, a bio-electrode for forming a living body contact layer from a bio-electrode composition including these salts is unfortunately subjected to salt extraction by sweating or washing to lower the conductivity. Since tetrafluoroborate salts are highly poisonous and other salts are highly water-soluble, they are readily immersed into the skin to cause rough skin (or, strong stimulation to the skin).

When an acid for forming a neutralization salt has a high acidity, the ion polarization is significant to improve the ion conductivity, thereby allowing a lithium salt of bis(trifluoromethane sulfonyl) imide acid or tris(trifluoromethane sulfonyl) methide acid as a lithium-ion battery to show high ion conductivity. Meanwhile, higher acid strength provides the salt with stronger living body stimulation, showing a trade-off between ion conductivity and living body stimulation. Nevertheless, salts for bio-electrode applications must satisfy both high ion conductivity and low living body stimulation.

Inventors of the present invention have carried out an extended investigation and found that a lithium salt, a sodium salt, a potassium salt, or an ammonium salt of sulfonamide in which a fluorosulfonic group is bonded to one side of a nitrogen atom and a carbonyl group is bonded to the other side shows a lower acidity than a lithium salt, a sodium salt, a potassium salt, or an ammonium salt of bissulfonamide in which a fluoroalkyl group is bonded to both sides of the sulfonamide, thereby causing lower living body stimulation, and high ion conductivity due to higher acidity than a lithium salt, a sodium salt, a potassium salt, or an ammonium salt of sulfonamide in which a fluorosulfonic group is bonded to one side of a nitrogen atom and an alkyl group is bonded to the other side. Also, higher molecular weight of an ion compound lowers the immersion into the skin and the resulting stimulation to the skin, and the ion compound is preferably a polymer of high molecular weight. Inventors of the present invention conceived synthesis of a polymer by copolymerizing a monomer containing a silicon atom using the ion compound having a polymerizable double bond. Furthermore, inventors of the present invention found that by mixing the salt with e.g., a silicone-based, an acrylic-based, or a urethane-based adhesive agent (resin), a living body contact layer can be formed to satisfy both conductivity and biocompatibility, control significant reduction in conductivity even though the bio-electrode is soaked in water or dried, and stably detect electric signals from a bio-electrode that is always close to the skin. Based on that information, the present invention was accomplished.

Specifically, the present invention provides a bio-electrode composition including an (A) ionic material and a (B) resin other than the component (A), wherein the component (A) has both a repeating unit "a" of a lithium salt, a sodium salt, a potassium salt, or an ammonium salt of sulfonimide having a partial structure represented by the following general formula (1) and a repeating unit "b" having a silicon atom,

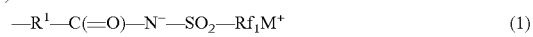

wherein, $R^1$ represents a single bond, or a linear, a branched, or a cyclic divalent hydrocarbon group having 1 to 40 carbon atoms, which may be substituted by a heteroatom, or mediated by a heteroatom; $Rf_1$ represents a linear or a branched alkyl group or a phenyl group having 1 to 4 carbon atoms, having one or more fluorine atoms or a trifluoromethyl group; $M^+$ represents any of a lithium ion, a sodium ion, a potassium ion, or an ammonium ion.

The present invention also provides a polymer including repeating units "a1" and "b1" represented by the following general formula (2),

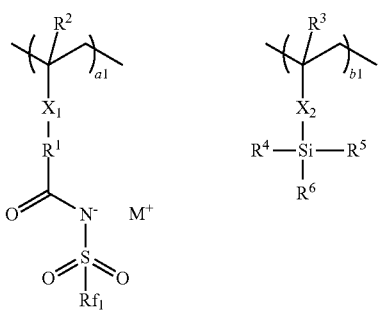

(2)

wherein, $R^1$ represents a single bond, or a linear, a branched, or a cyclic divalent hydrocarbon group having 1 to 40 carbon atoms, which may be substituted by a heteroatom, or mediated by a heteroatom; $Rf_1$ represents a linear or a branched alkyl group or a phenyl group having 1 to 4 carbon atoms, having one or more fluorine atoms or a trifluoromethyl group; $M^+$ represents any of a lithium ion, a sodium ion, a potassium ion, or an ammonium ion; each of $R^2$ and $R^3$ independently represents a hydrogen atom or a methyl group; $X_1$ represents any of a single bond, a phenylene group, a naphthylene group, an ether group, an ester group, or an amide group; $X_2$ represents any of an arylene group having 6 to 12 carbon atoms, a —C(=O)—O—$R^7$— group, or a —C(=O)—NH—$R^7$— group; $R^7$ represents any of a single bond, a linear, a branched, or a cyclic alkylene group, or a phenylene group having 2 to 12 carbon atoms, and may include one or more groups selected from an ether group, a carbonyl group, an ester group, and an amide group; each of $R^4$, $R^5$, and $R^6$ independently represents a linear, a branched, or a cyclic alkyl group having 1 to 6 carbon atoms, or an aryl group having 6 to 10 carbon atoms, and may include one or more selected from a siloxane bond, a silicon atom, and a halogen atom; $R^4$ and $R^5$, or $R^4$, $R^5$, and $R^6$ may be bonded to form a ring or a three-dimensional structure; and "a1" and "b1" are numbers satisfying the equations $0<a1<1.0$ and $0<b1<1.0$.

The present invention will be described in detail, but the present invention is not restricted thereto.

Bio-Electrode Composition

The bio-electrode composition of the present invention includes an (A) ionic material and a (B) resin. Each component of the bio-electrode of the present invention will be described in more detail.

(A) Ionic Material (Salt)

The salt blended into the bio-electrode composition of the present invention as an (A) ionic material (conductive material) is a polymer including both a repeating unit "a" of a lithium salt, a sodium salt, a potassium salt, or an ammonium salt of sulfonamide having a partial structure represented by the following general formula (1) with a fluorosulfonic group bonded on one side of a nitrogen atom and a carbonyl group bonded on the other side, and a repeating unit "b" having a silicon atom,

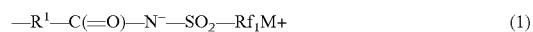

(1)

wherein, $R^1$ represents a single bond, or a linear, a branched, or a cyclic divalent hydrocarbon group having 1 to 40 carbon atoms, which may be substituted by a heteroatom, or mediated by a heteroatom; $Rf_1$ represents a linear or a branched alkyl group or a phenyl group having 1 to 4 carbon atoms, having one or more fluorine atoms or a trifluoromethyl group; $M^+$ represents any of a lithium ion, a sodium ion, a potassium ion, or an ammonium ion.

Preferably, a polymer salt blended into the bio-electrode composition of the present invention as an (A) ionic material is a polymer of the present invention including repeating units "a1" and "b1" represented by the following general formula (2) as the above repeating units "a" and "b",

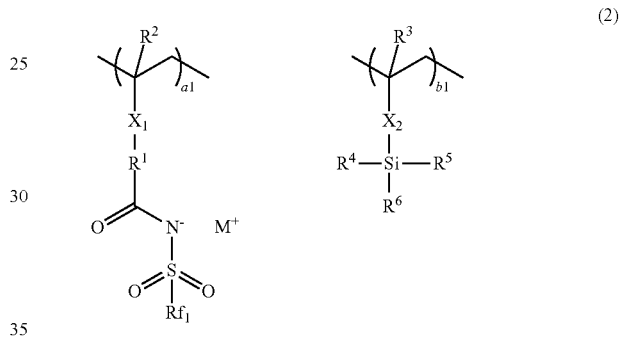

(2)

wherein, $R^1$, $Rf_1$, and $M^+$ represent the same meanings as before. Each of $R^2$ and $R^3$ independently represents a hydrogen atom or a methyl group; $X_1$ represents any of a single bond, a phenylene group, a naphthylene group, an ether group, an ester group, or an amide group; $X_2$ represents any of an arylene group having 6 to 12 carbon atoms, a —C(=O)—O—$R^7$— group, or a —C(=O)—NH—$R^7$— group; $R^7$ represents any of a single bond, a linear, a branched, or a cyclic alkylene group, or a phenylene group having 2 to 12 carbon atoms, and may include one or more groups selected from an ether group, a carbonyl group, an ester group, and an amide group; each of $R^4$, $R^5$, and $R^6$ independently represents a linear, a branched, or a cyclic alkyl group having 1 to 6 carbon atoms, or an aryl group having 6 to 10 carbon atoms, and may include one or more selected from a siloxane bond, a silicon atom, and a halogen atom; $R^4$ and $R^5$, or $R^4$, $R^5$, and $R^6$ may be bonded to form a ring or a three-dimensional structure; and "a1" and "b1" are numbers satisfying the equations $0<a1<1.0$ and $0<b1<1.0$.

Repeating Unit "a"

The component (A) has a repeating unit "a" of a lithium salt, a sodium salt, a potassium salt, or an ammonium salt of sulfonimide having a partial structure represented by the general formula (1) of the bio-electrode composition of the present invention. The repeating unit "a" is preferably a repeating unit "a1" in the general formula (2).

The monomer of sulfonamide for obtaining the repeating unit "a1" in the general formula (2) is represented by the following general formula (4),

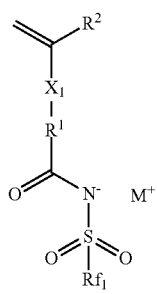
(4)
wherein, $R^1$, $R^2$, $X_1$, $Rf_1$, and $M^+$ represent the same meanings as before.
Illustrative example of the monomer represented by the general formula (4) includes the following monomers,
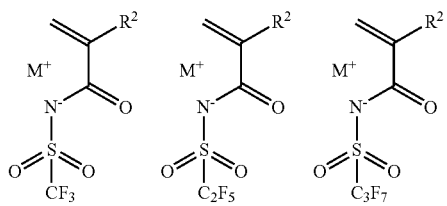
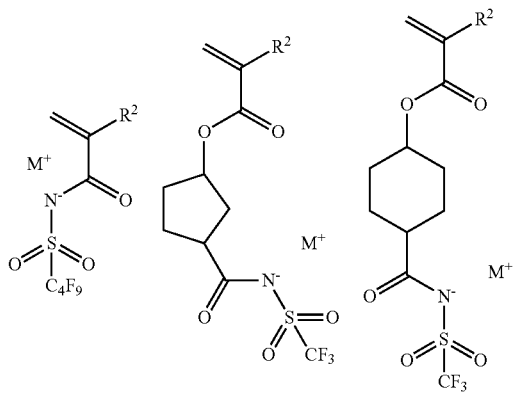
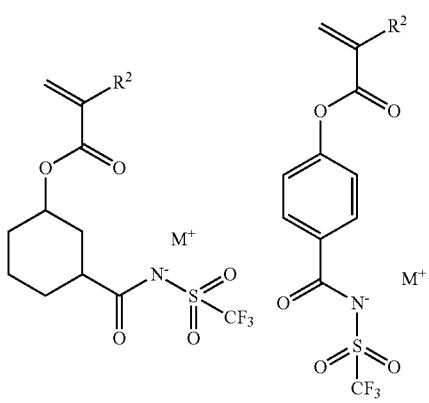
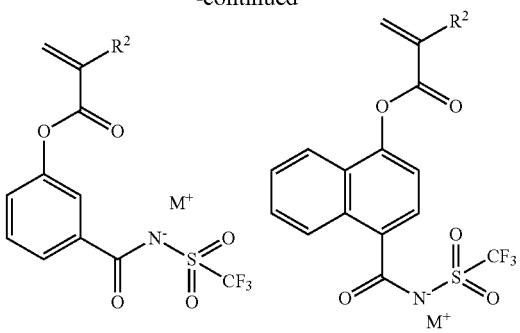
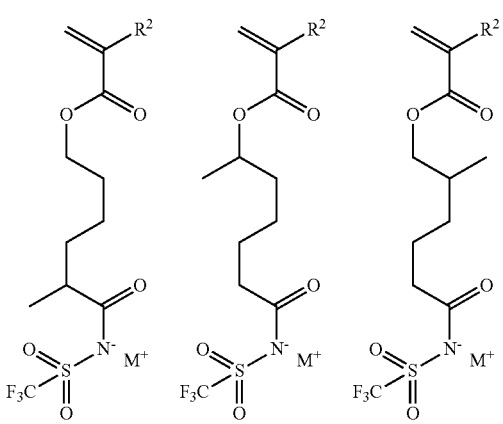
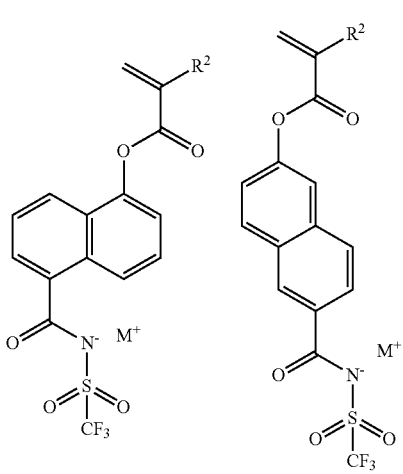
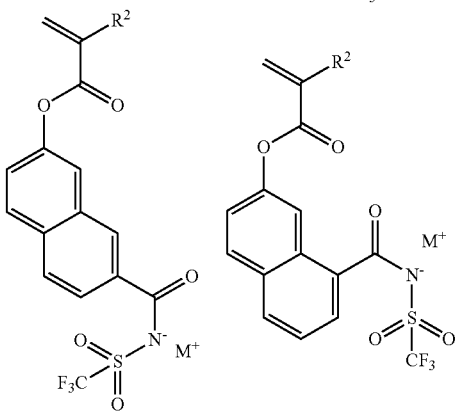

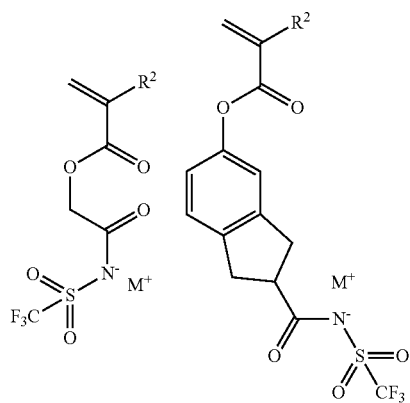
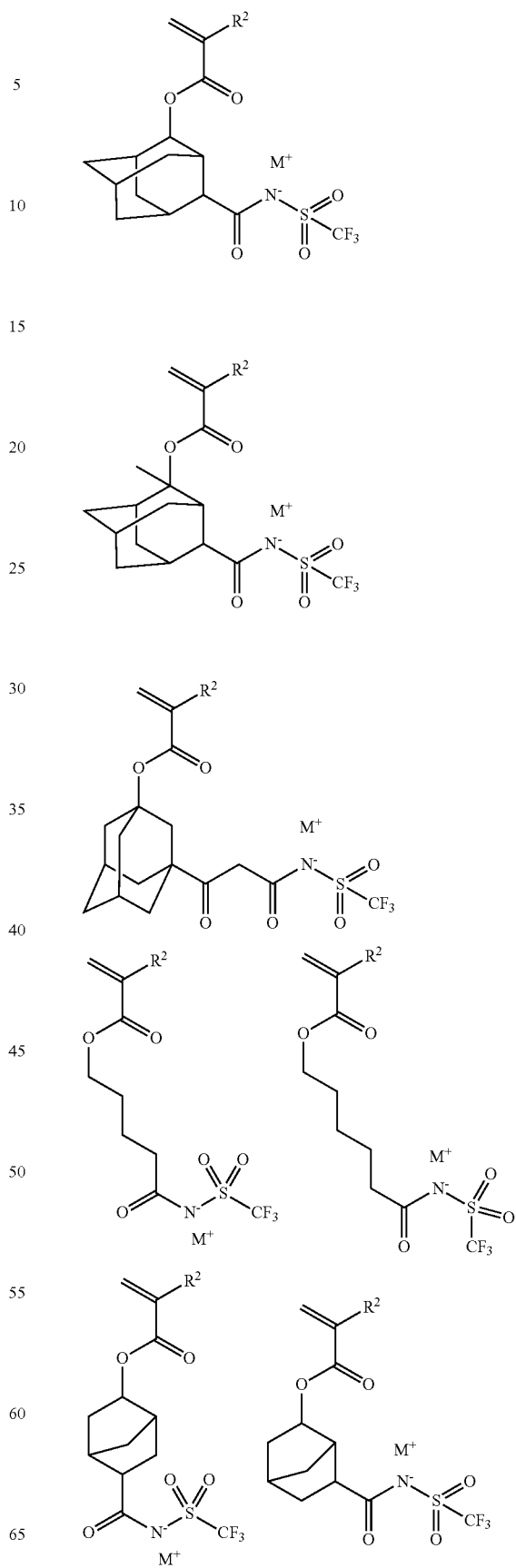

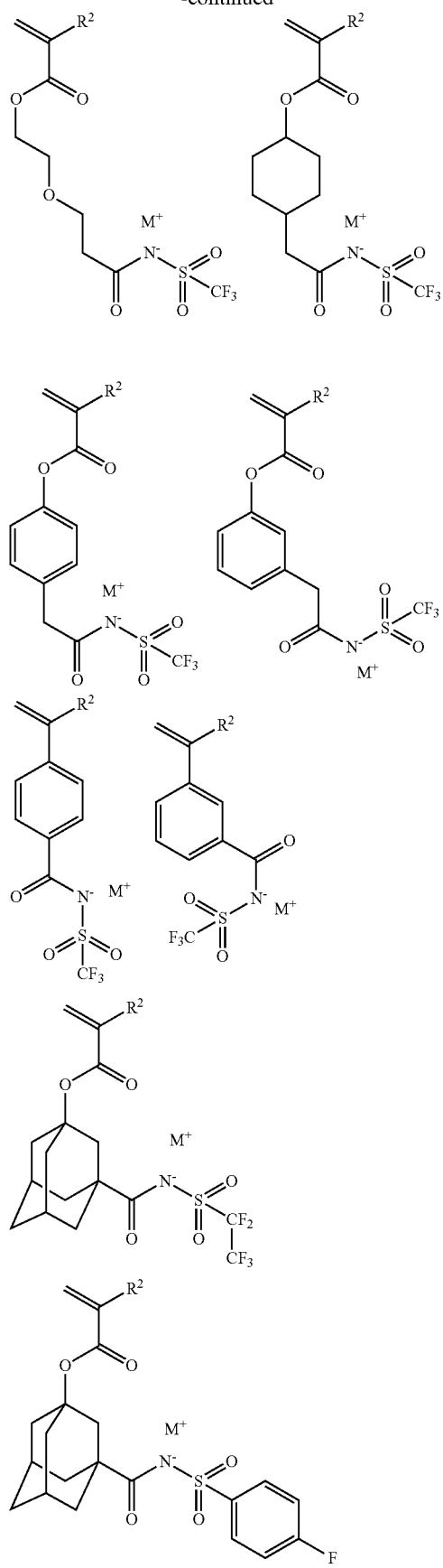
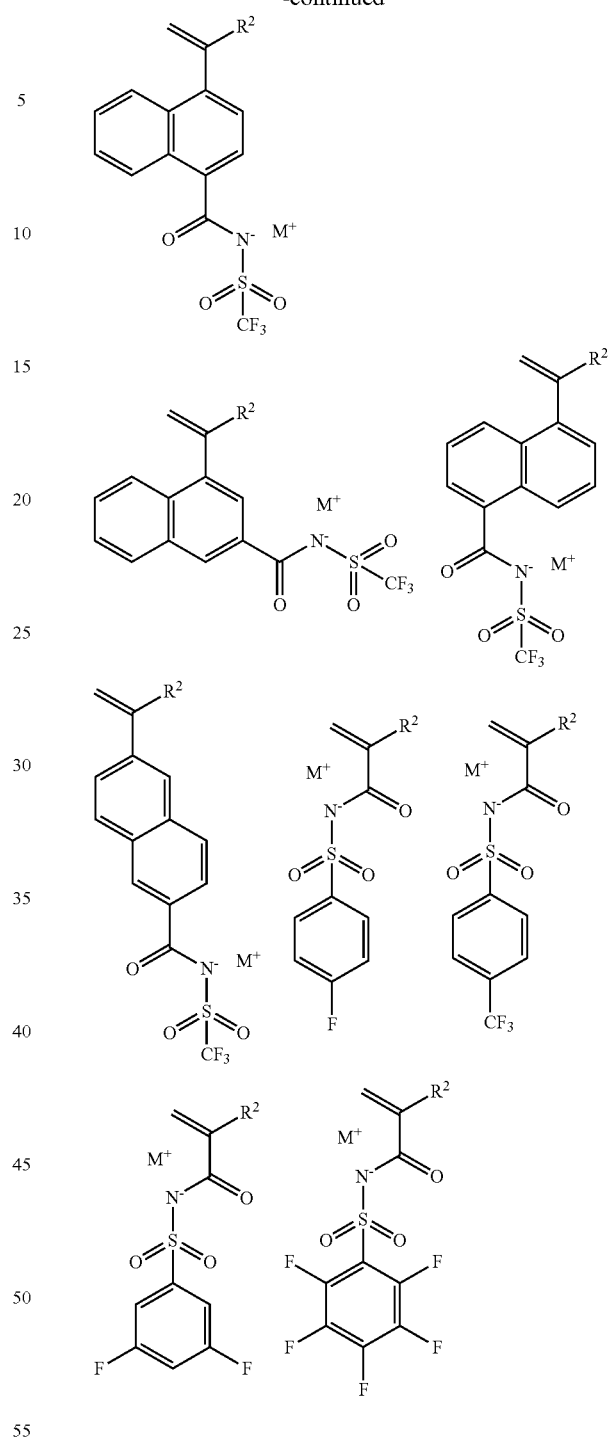

wherein, $R^2$ and $M^+$ represent the same meanings as before.

Illustrative example of the method for synthesizing a monomer of a lithium salt, an sodium salt, a potassium salt, or an ammonium salt for obtaining the repeating unit represented by the general formula (4) includes the method for reacting an oxychloride having a polymerizable group and fluoroalkane sulfonamide in the presence of a base in an organic solvent represented by the following formula. The method for synthesizing a monomer of the present invention is not restricted thereto,

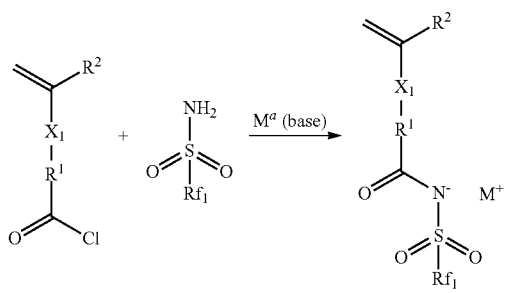
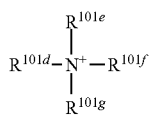

wherein, $R^1$, $R^2$, $X_1$, $Rf_1$, and $M^+$ represent the same meanings as before. $M^a$ represents a base.

In the above formula, the amount of oxychloride to be used is preferably 0.5 to 3 moles, and more preferably 0.8 to 1.5 moles relative to 1 mole of fluoroalkane sulfonamide. Also, oxychloride can be synthesized by a known method by action of oxalyl chloride and thionyl chloride on carboxylic acid in an organic solvent from a corresponding carboxylic acid.

The fluoroalkane sulfonamide may be a commercially available product, and ammonia may be reacted with a corresponding fluoroalkane sulfonylhalides or fluoroalkane sulfonic acid anhydride for monomer synthesis.

The base $M^a$ is not particularly restricted. Illustrative example thereof includes lithium carbonate, lithium hydroxide, sodium carbonate, sodium hydroxide, sodium hydride, potassium carbonate, potassium hydroxide, potassium hydride, trimethylamine, triethylamine, diisopropylethylamine, pyridine, lutidine, collidine, and N,N-dimethylaminopyridine. The amount of a base to be used is preferably 1.0 to 4.0 moles relative to 1 mole of fluoroalkane sulfonamide. For monomer synthesis, when $M^+$ is a sodium ion, the sodium-based base can be used, and when $M^+$ is a potassium ion, the potassium-based base can be used. When $M^+$ is a tertiary or a quaternary ammonium ion, its corresponding tertiary amine or quaternary amine salt can be used for monomer synthesis. When $M^+$ is an ammonium ion, cation exchange is subjected to a monomer of a sodium ion or a potassium ion for monomer synthesis.

Illustrative example of the reaction solvent includes acetonitrile, chloride methylene, dichloroethane, acetone, 2-butanone, ethyl acetate, dimethyl formamide, N-methylpyrrolidone, tetrahydrofuran, 1,4-dioxane, toluene, xylene, hexane, heptane, and chlorobenzene can be used singularly or mixed in combination therewith, and can be reacted in solventless state. The reaction temperature is preferably −10° C. to a boiling point of a solvent, more preferably 0° C. to a boiling point of a solvent. The reaction time is usually 30 minutes to 40 hours.

In the above formula, in place of oxychloride, acid anhydride can be used for a similar reaction, as well as a corresponding sulfonamide salt such as trifluoromethane sulfonamide potassium salt, in place of fluoroalkane sulfonamide.

The component (A), as $M^+$ in a repeating unit "a" (repeating unit "a1"), includes an ammonium ion (ammonium cation) represented by the following general formula (3), $$R^{101d}-\underset{\underset{R^{101g}}{|}}{\overset{\overset{R^{101e}}{|}}{N^+}}-R^{101f} \quad (3)$$

wherein, each of $R^{101d}$, $R^{101e}$, $R^{101f}$, and $R^{101g}$ independently represents any of a hydrogen atom, a linear, a branched, or a cyclic alkyl group having 1 to 12 carbon atoms, a linear, a branched, or a cyclic alkenyl group or an alkynyl group having 2 to 12 carbon atoms, or an aromatic group having 4 to 20 carbon atoms, and may include one or more selected from an ether group, a carbonyl group, an ester group, a hydroxy group, an amino group, a nitro group, a sulfonyl group, a sulfinyl group, a halogen atom, and a sulfur atom; $R^{101d}$ and $R^{101e}$, or $R^{101d}$, $R^{101e}$, and $R^{101f}$ may form a ring together with a nitrogen atom bonded to these, and in this case, $R^{101d}$ and $R^{101e}$, or $R^{101d}$, $R^{101e}$, and $R^{101f}$ represent an alkylene group having 3 to 10 carbon atoms, or form a heteroaromatic ring having a nitrogen atom in the formula in the ring.

Illustrative example of the ammonium ion represented by the general formula (3) includes the following ammonia,

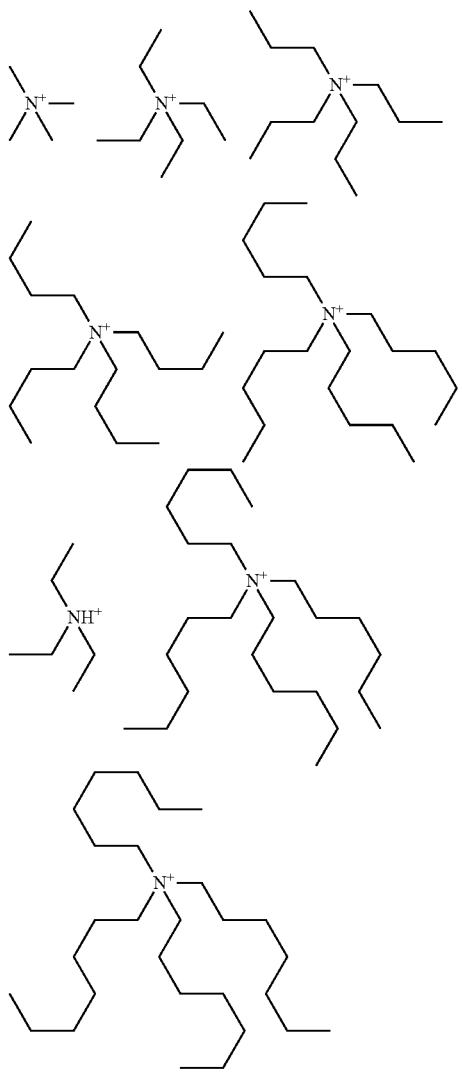

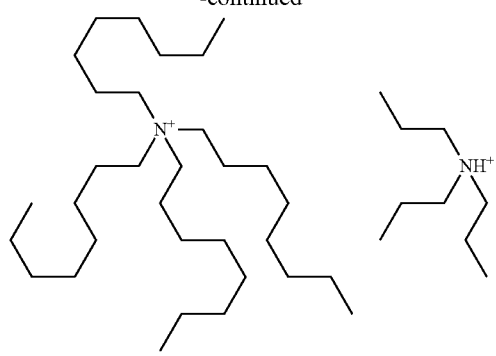
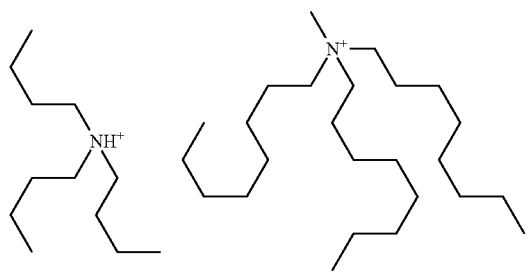
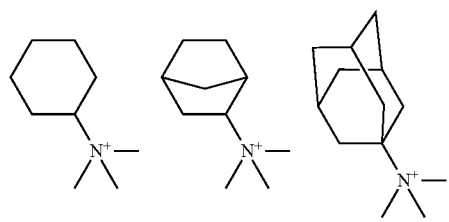
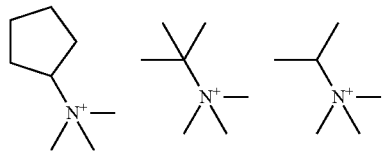
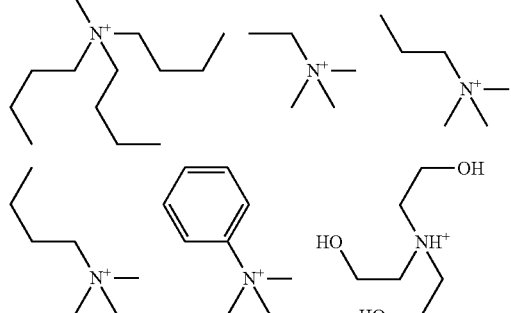
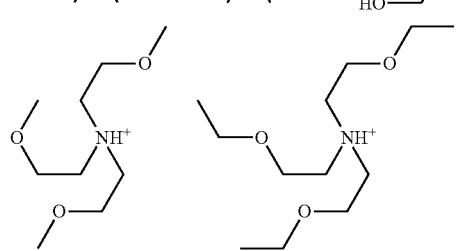
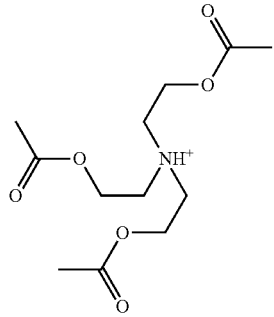
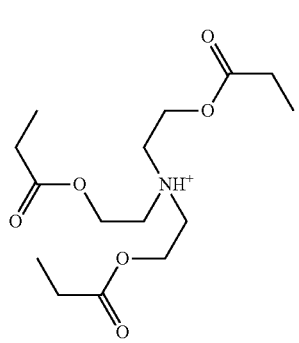
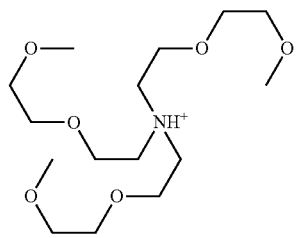
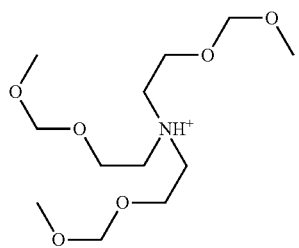
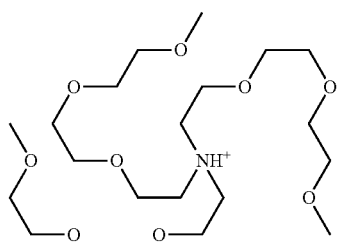
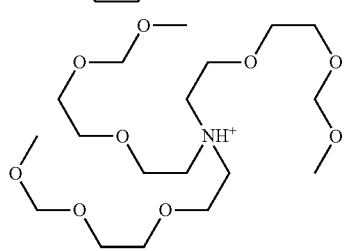

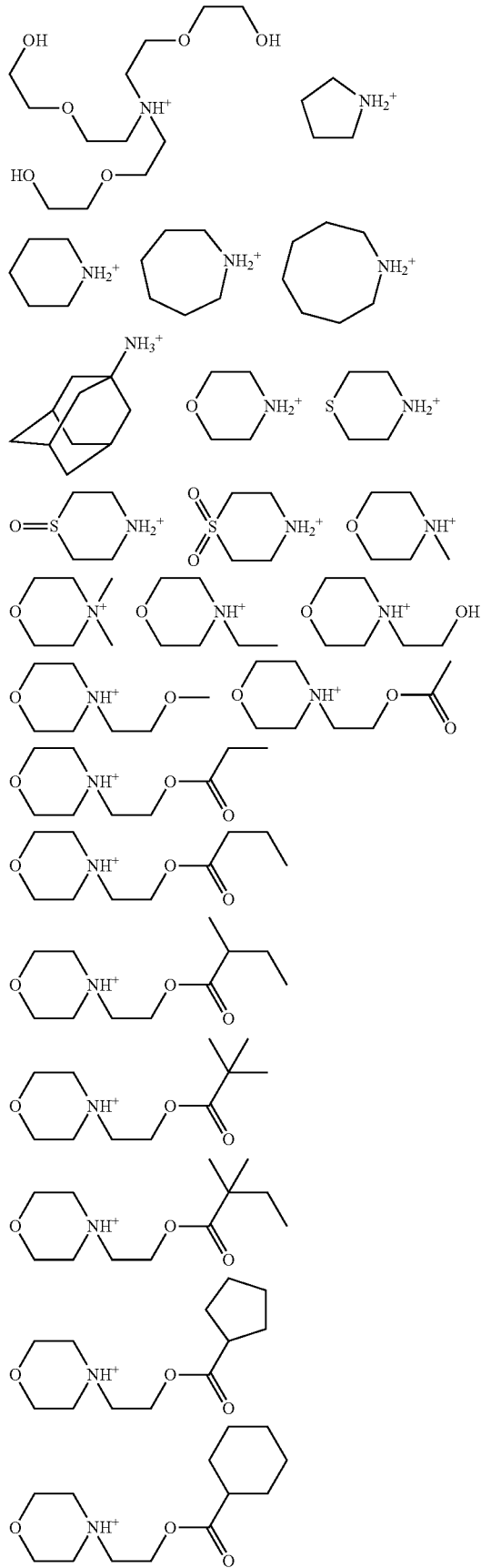
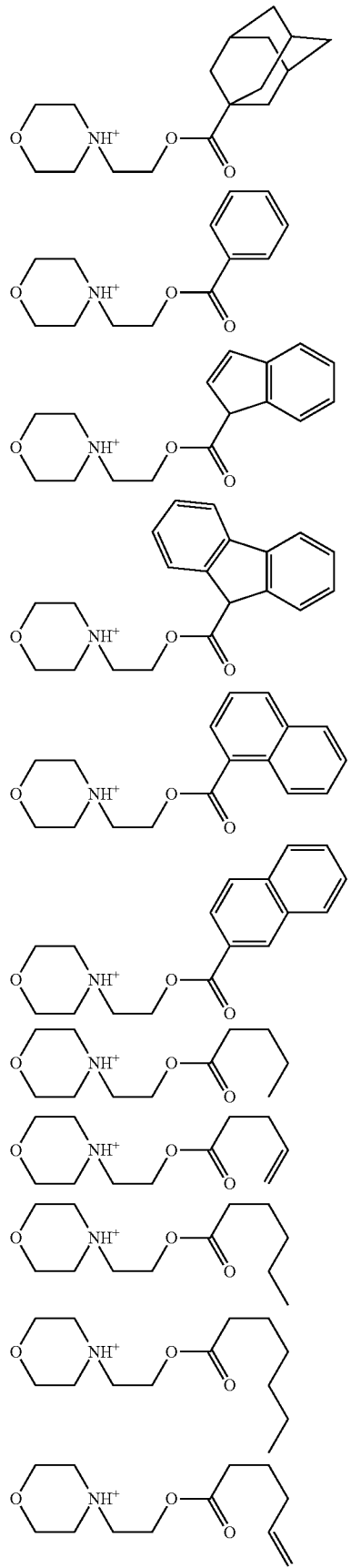

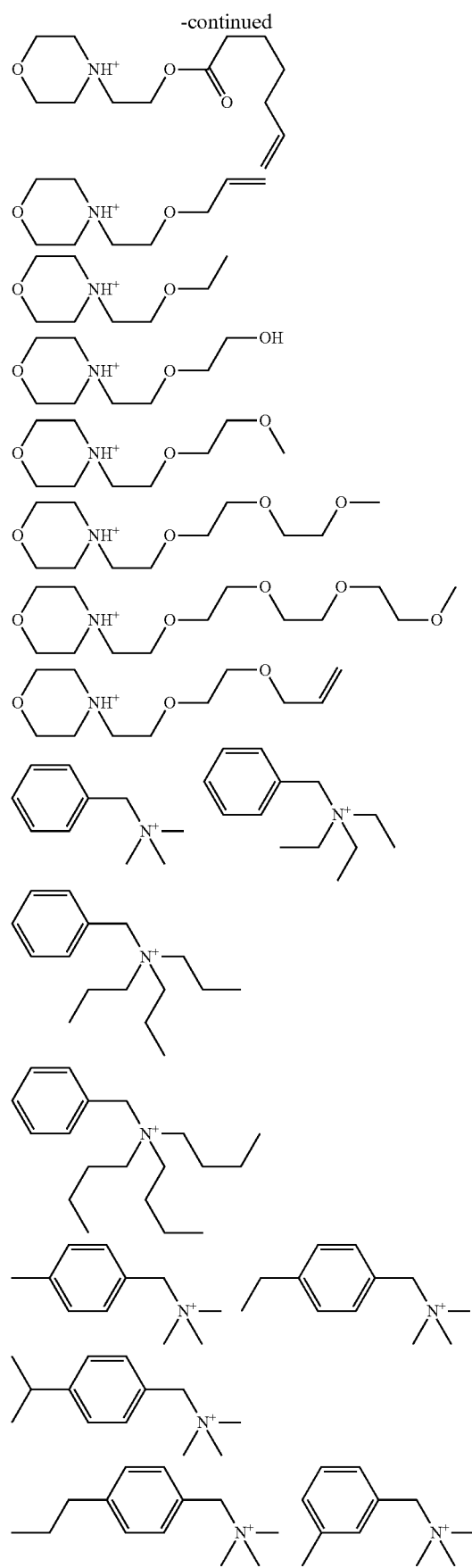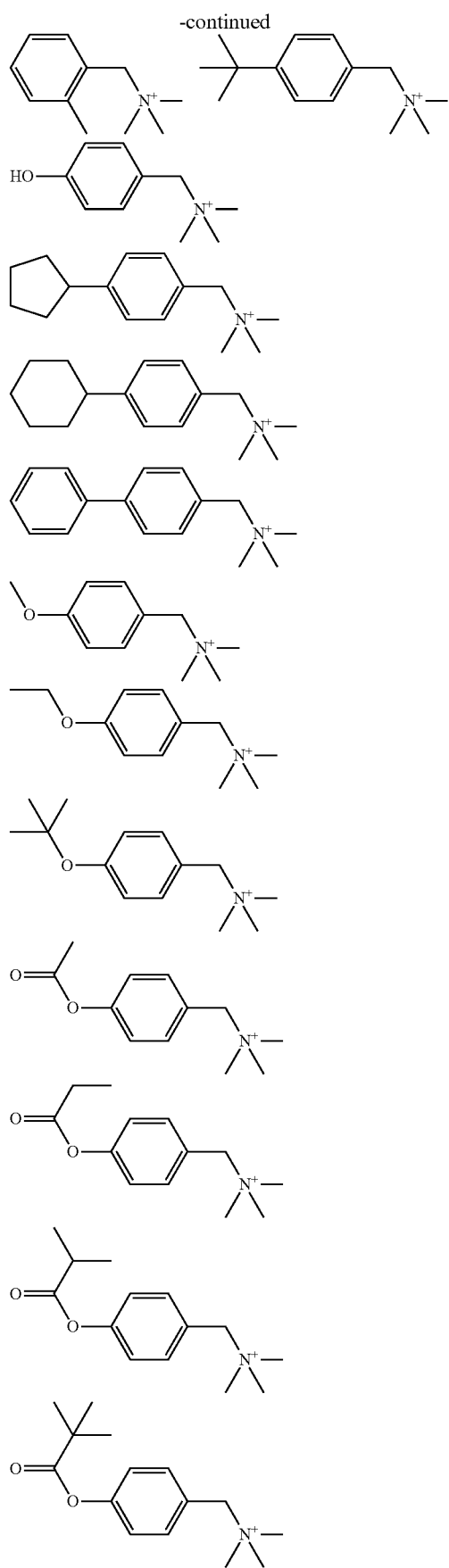

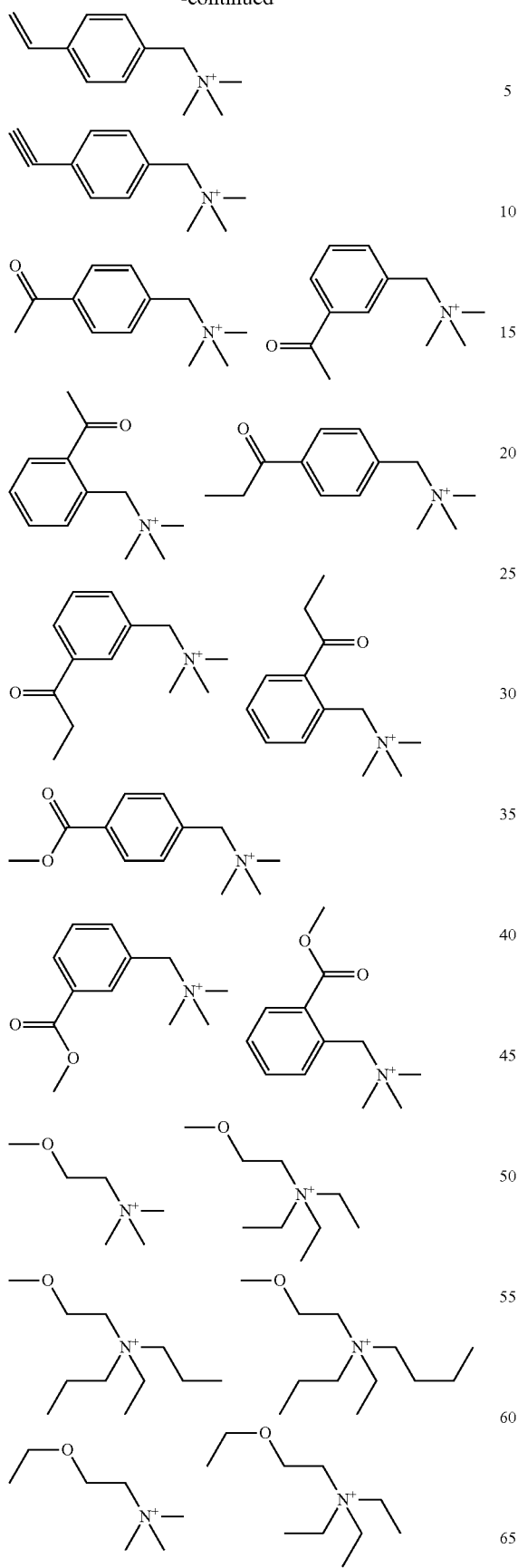
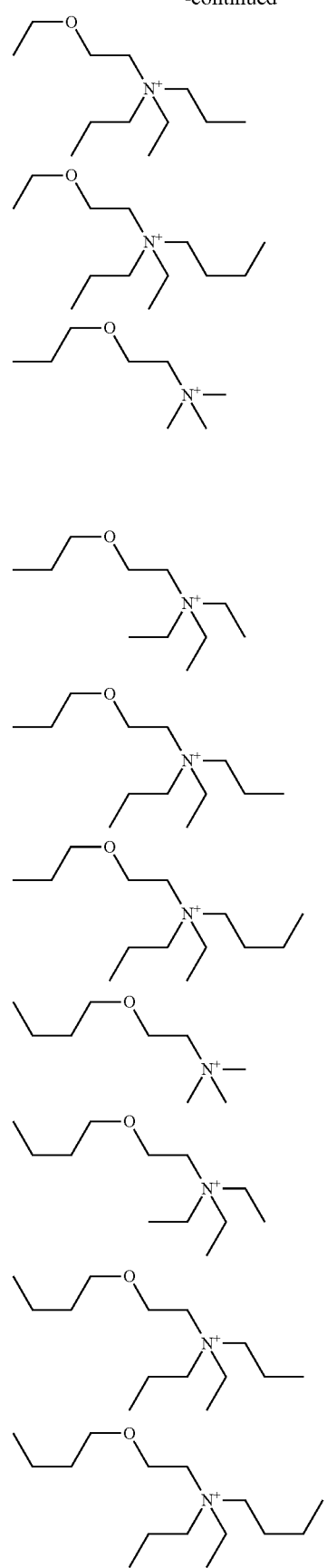

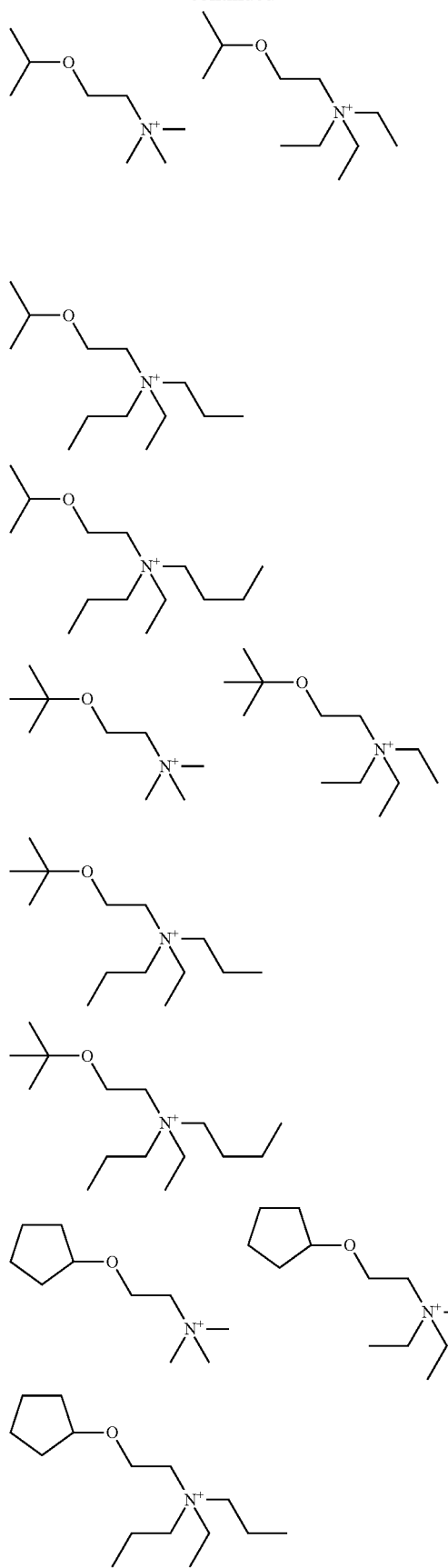
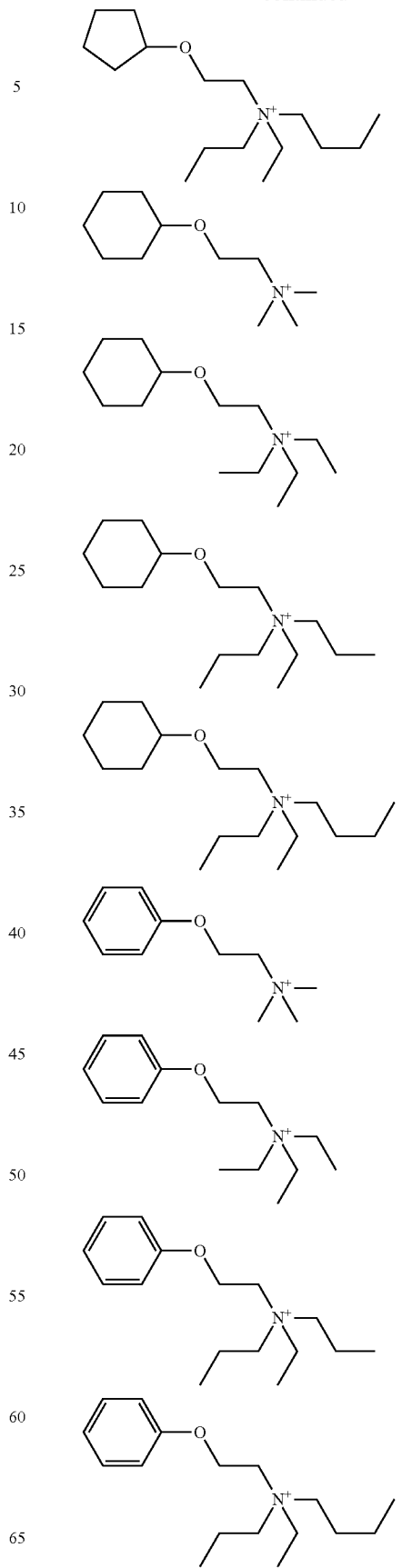

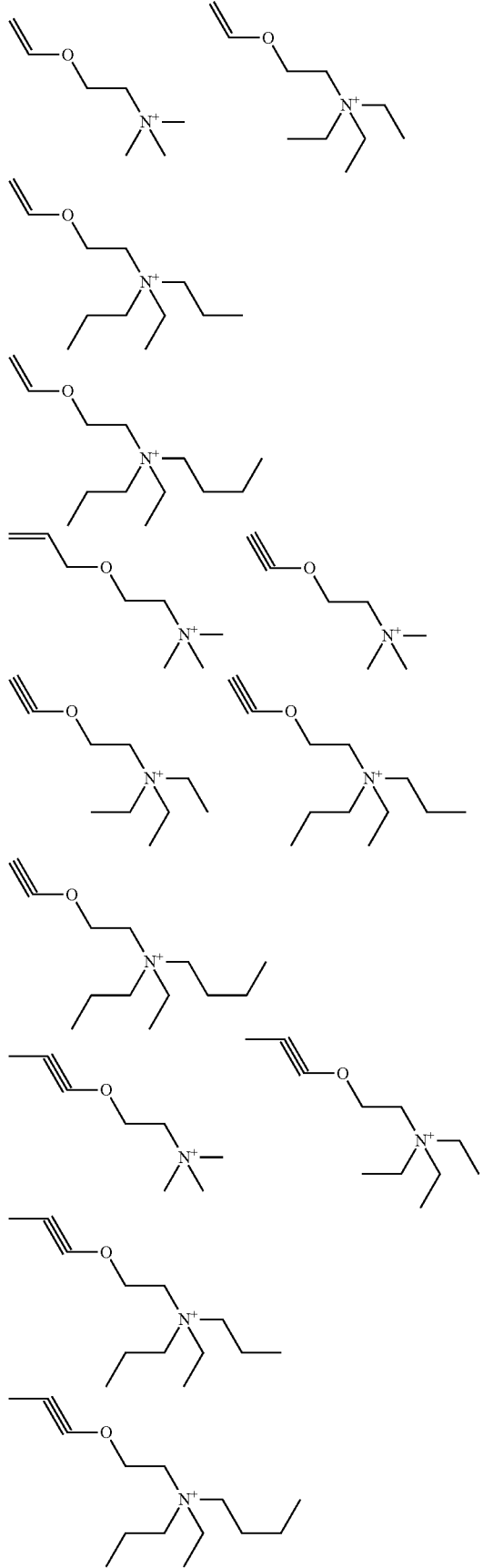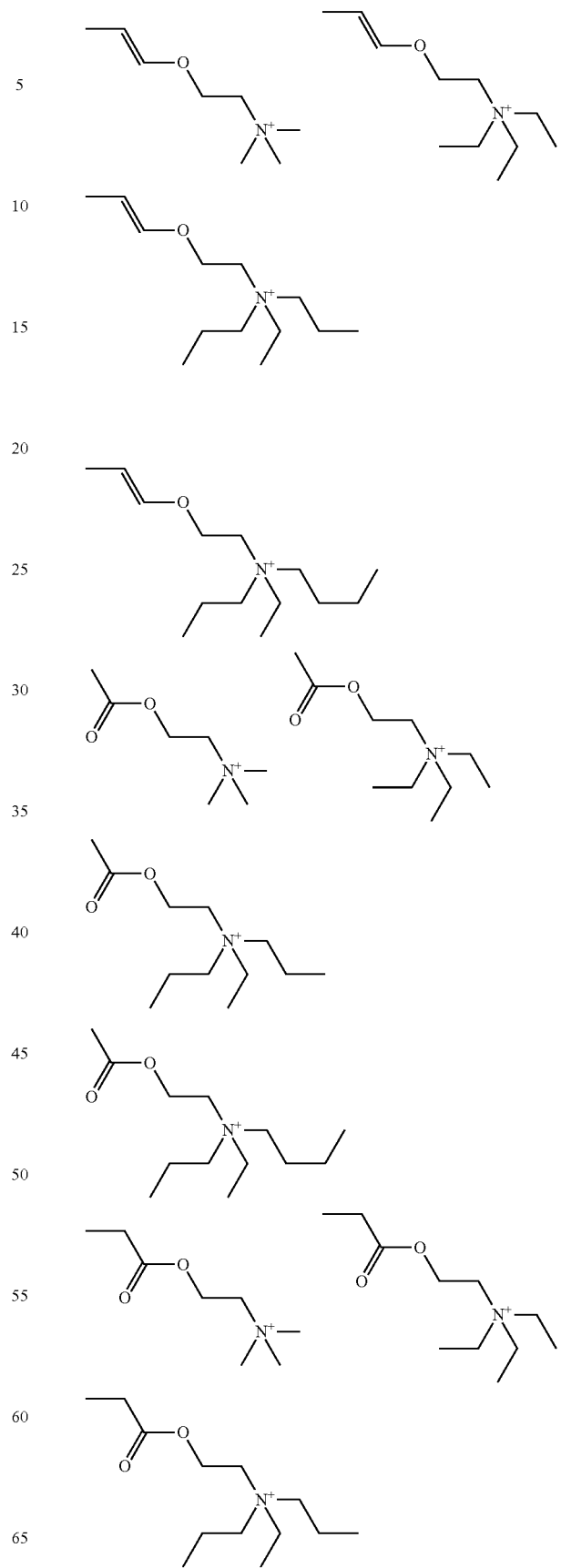

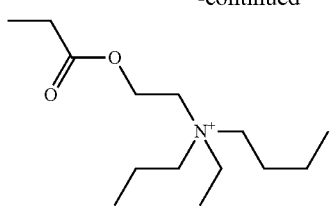
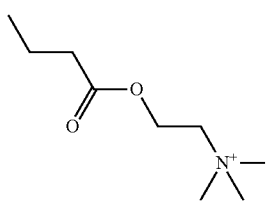
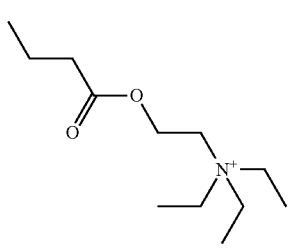
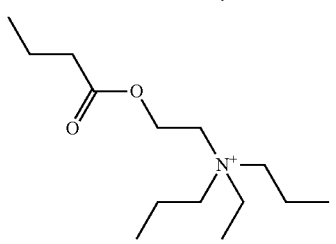
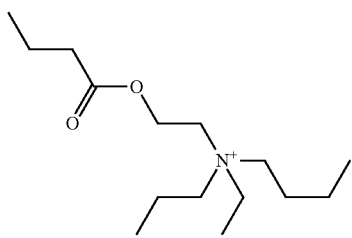
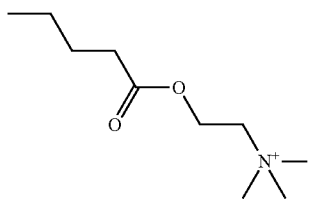
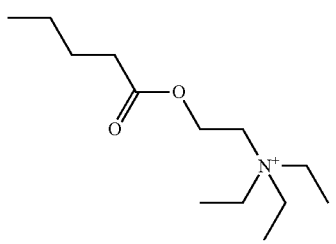
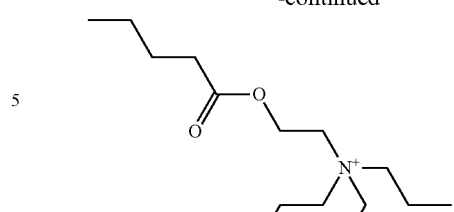
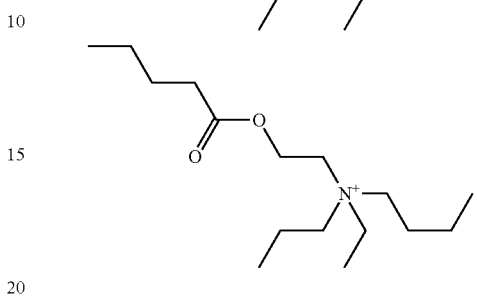
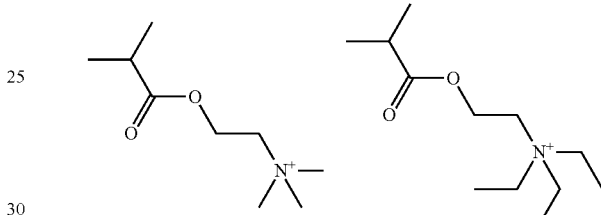
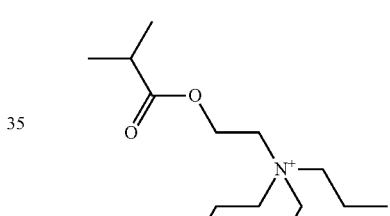
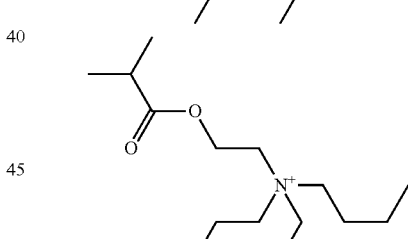
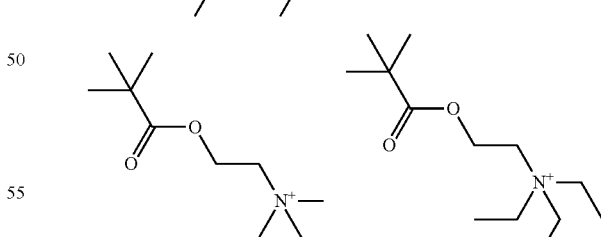
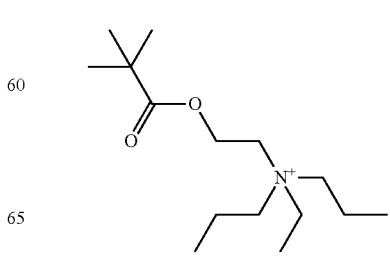

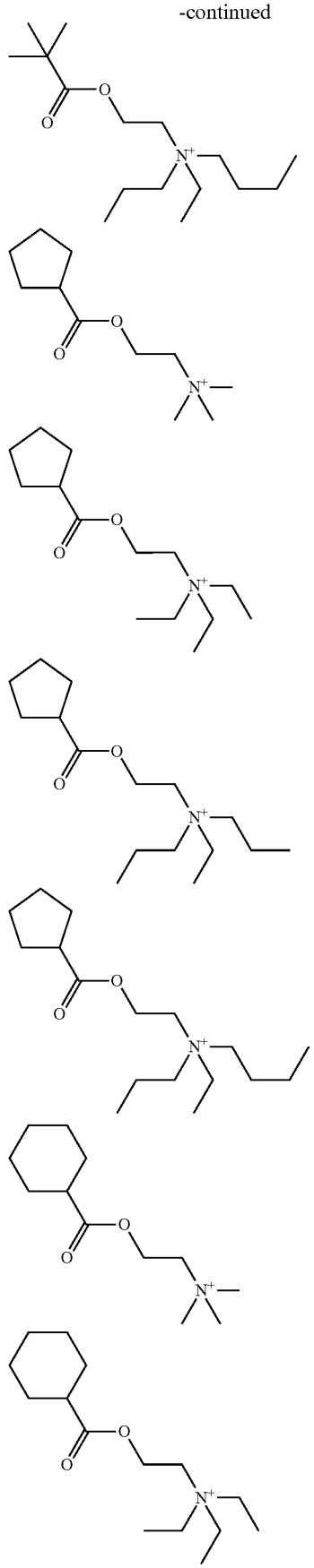
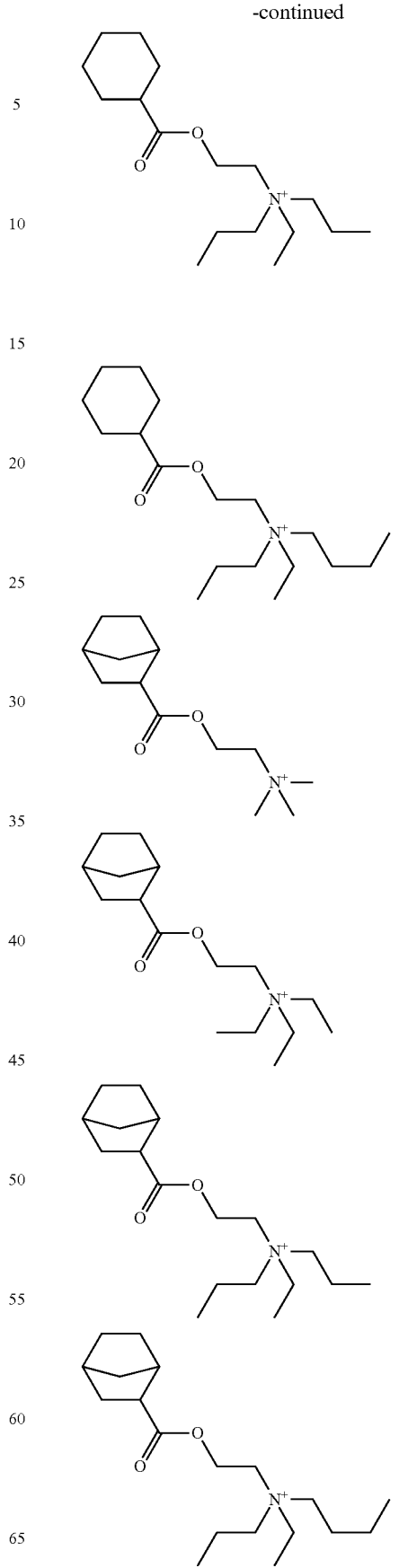

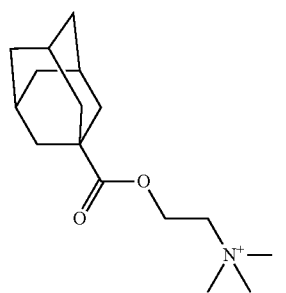
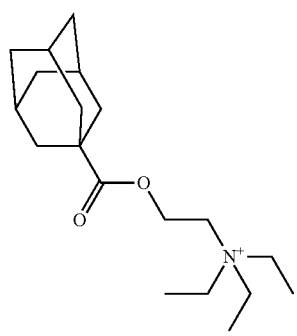
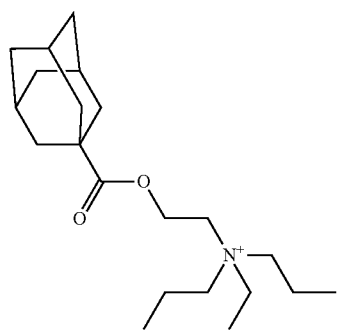
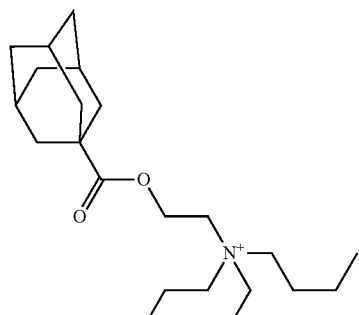
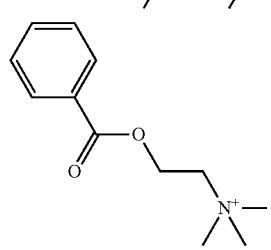
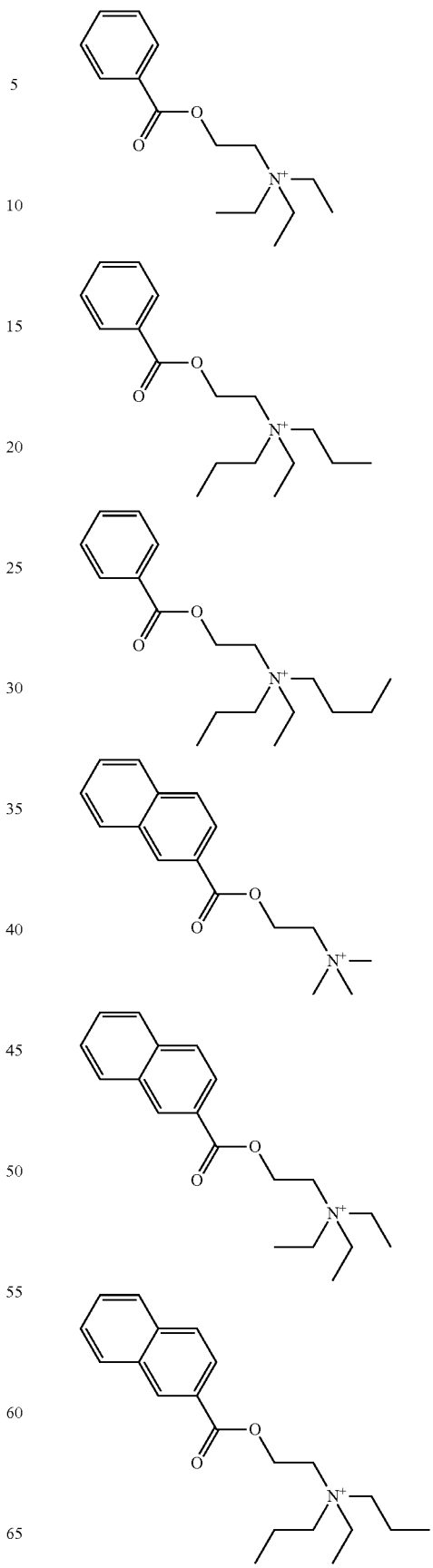

37
-continued
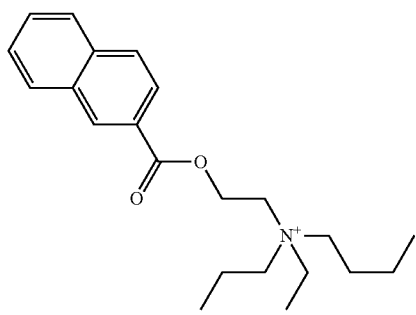
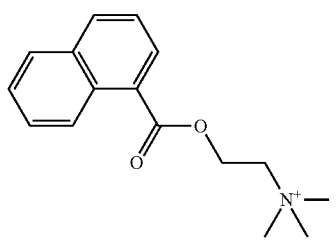
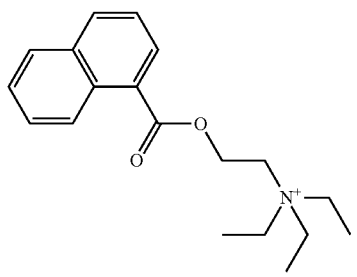
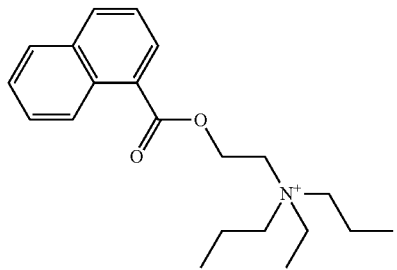
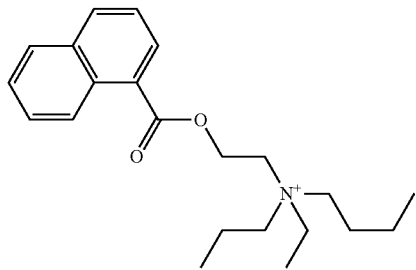
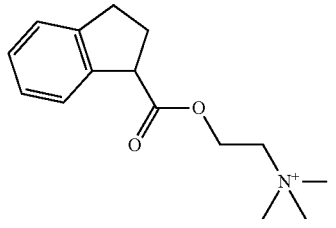
38
-continued
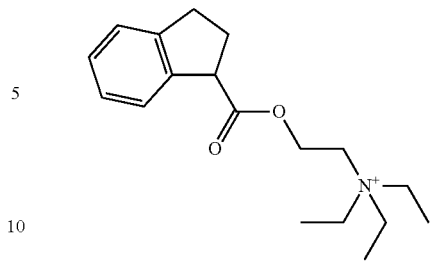
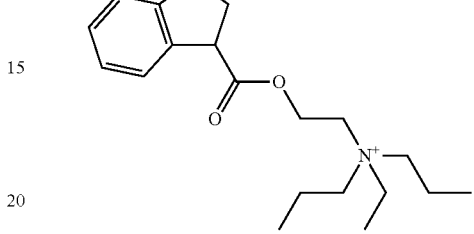
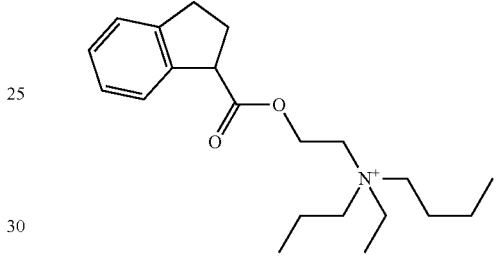
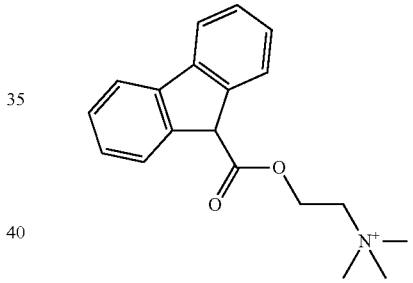
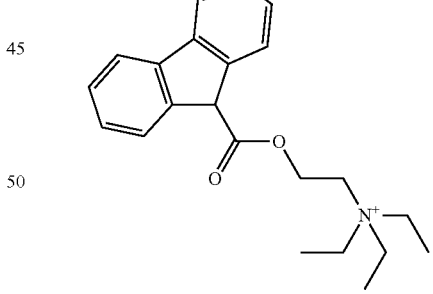
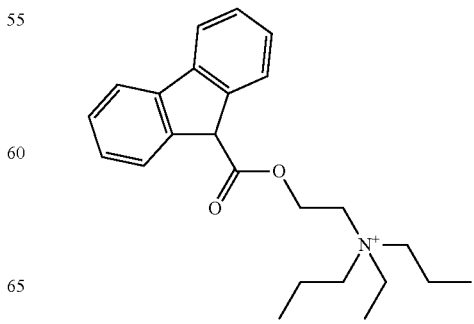

39
-continued
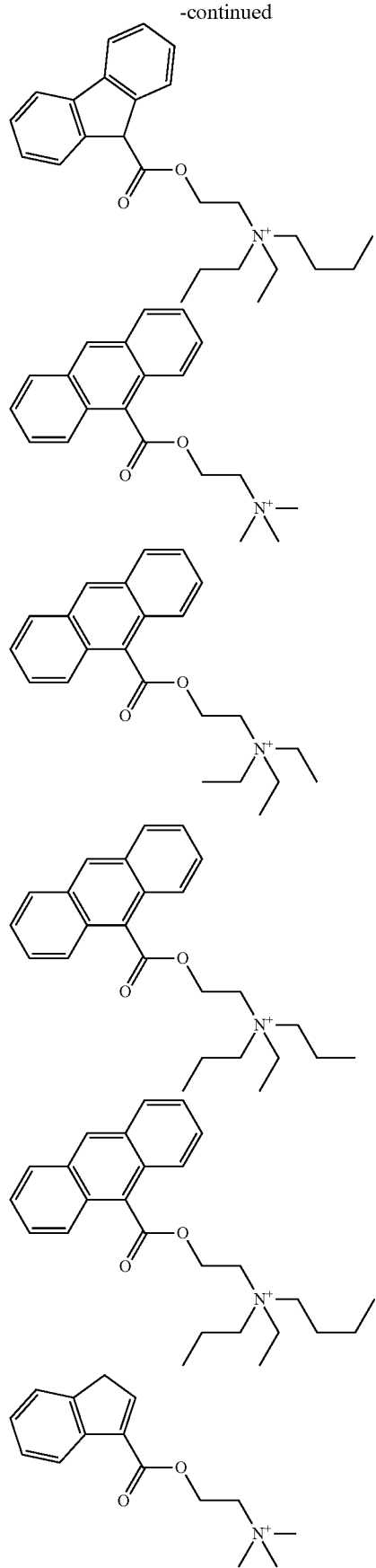
40
-continued
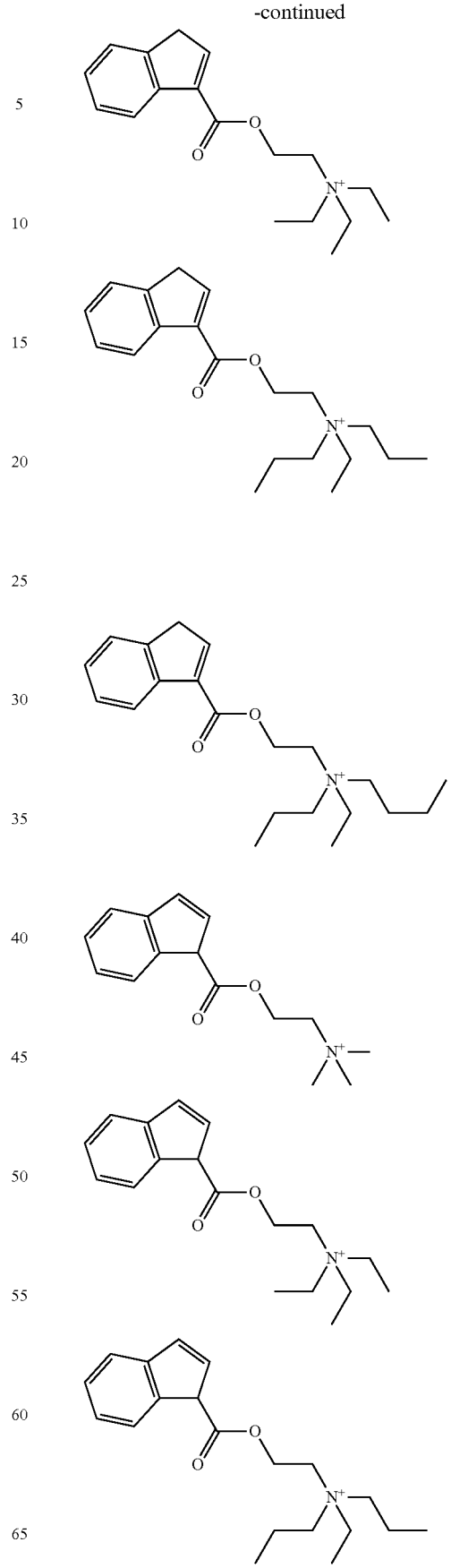

41
-continued
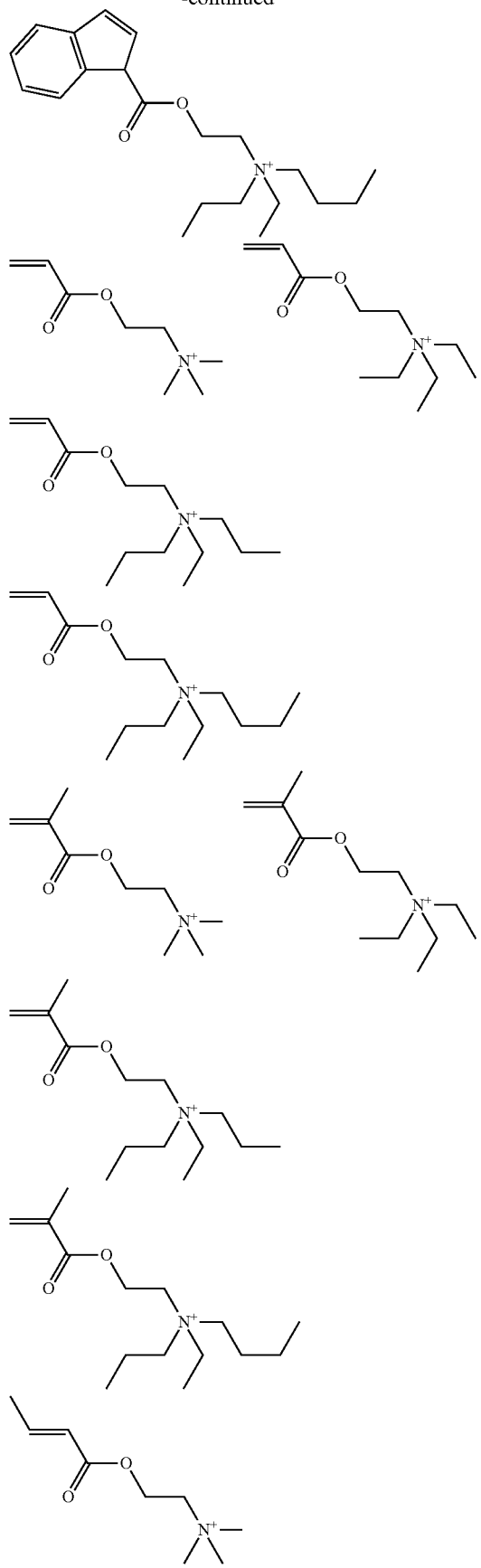
42
-continued
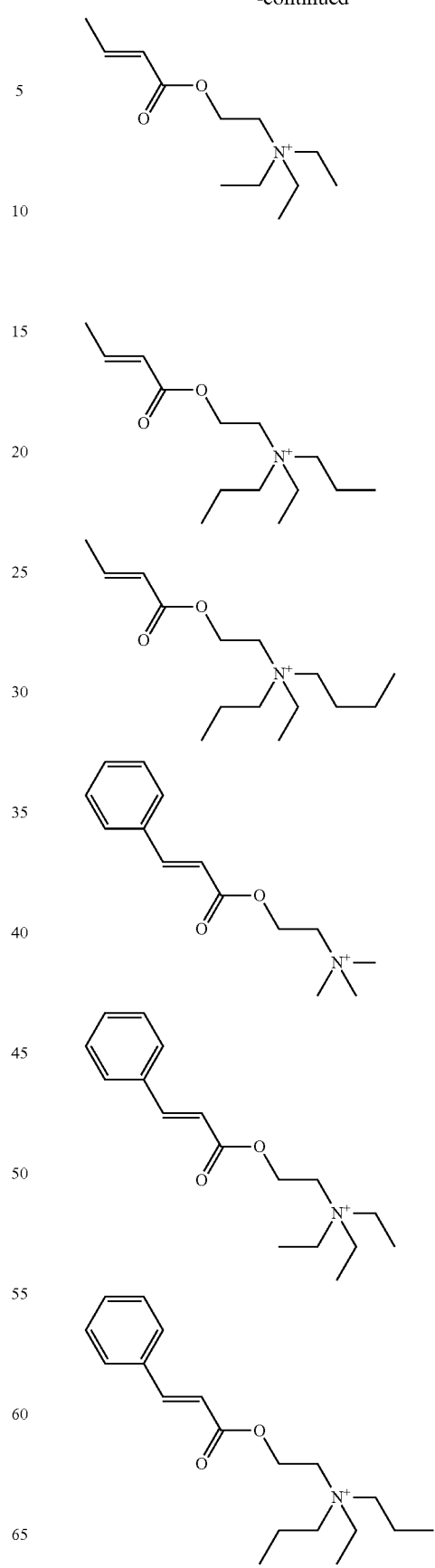

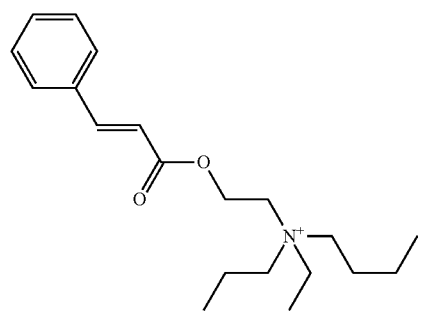
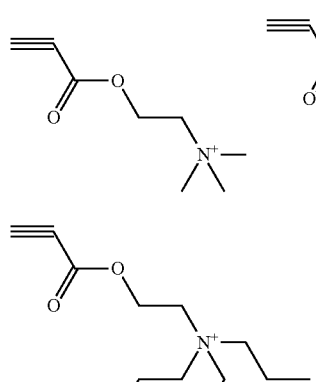
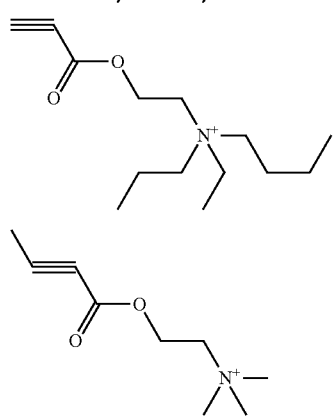
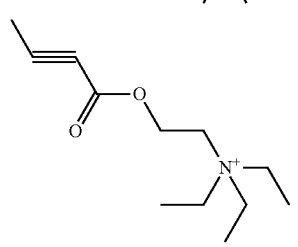
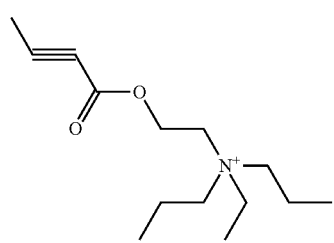
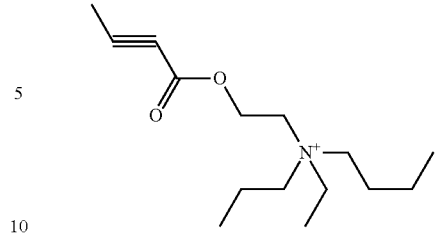
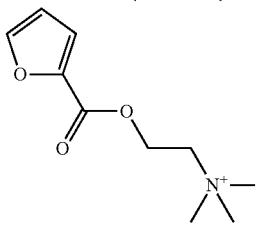
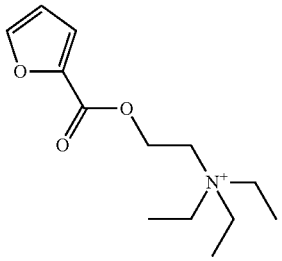
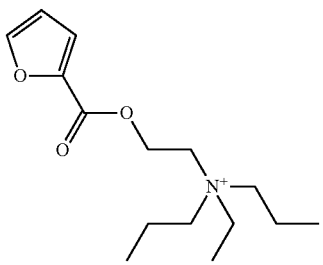
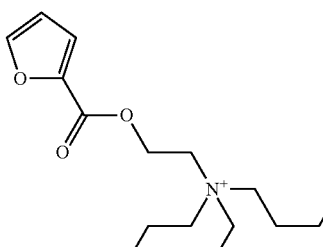
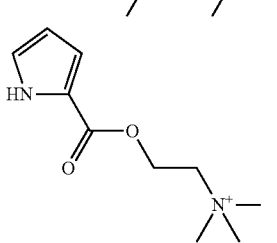
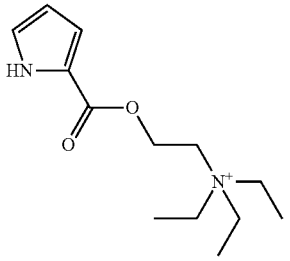

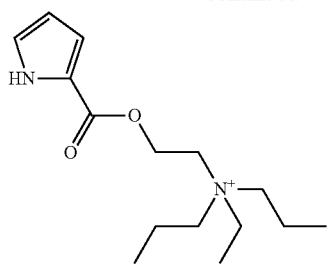
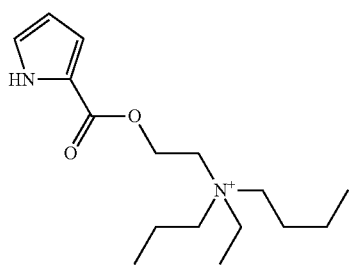
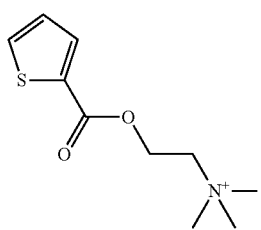
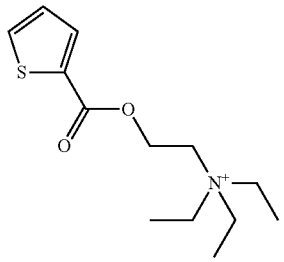
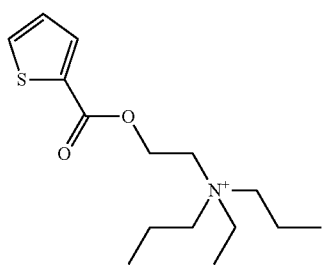
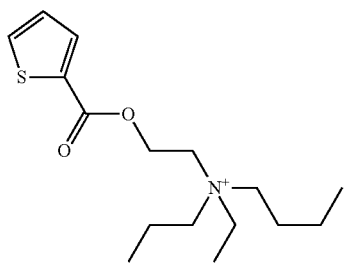
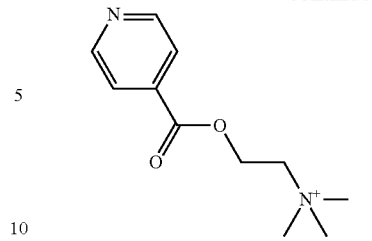
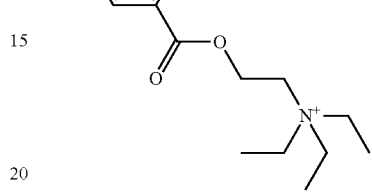
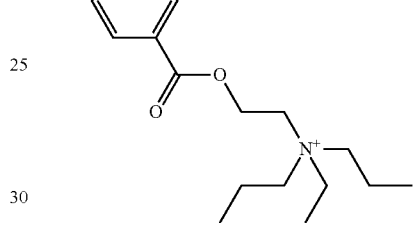
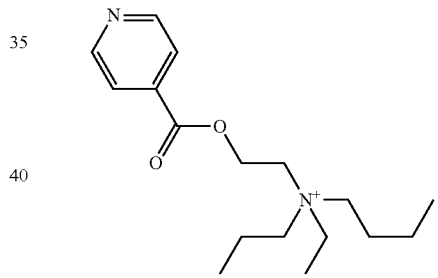
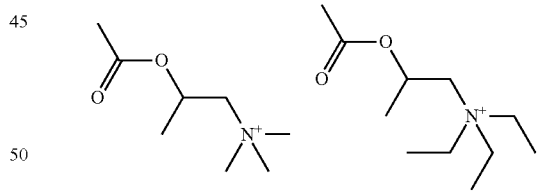
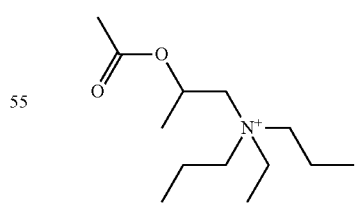
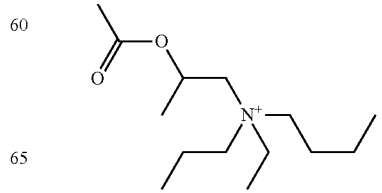

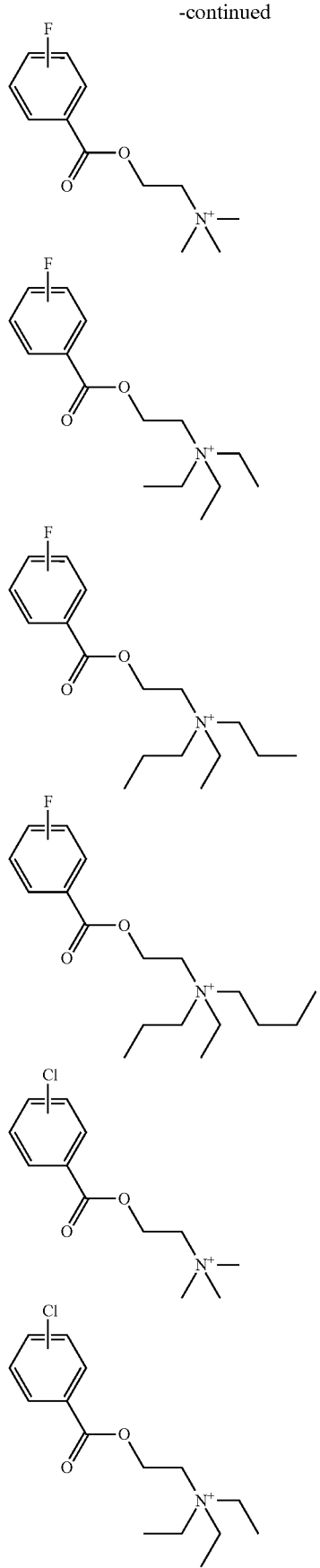
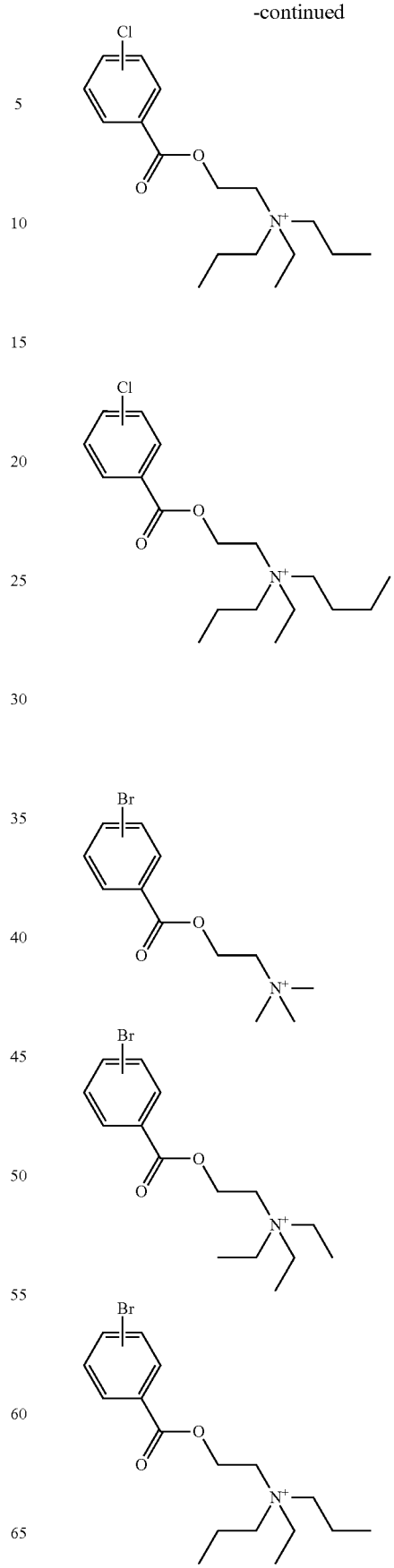

49
-continued
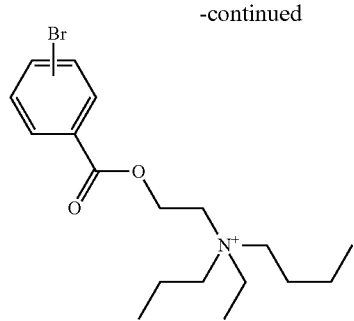
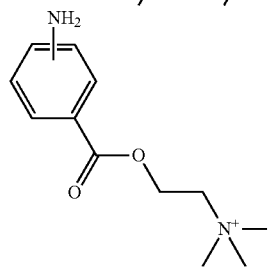
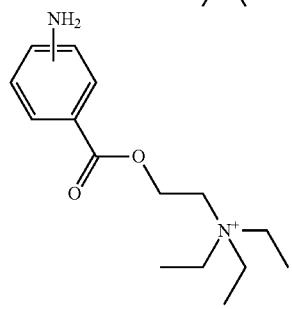
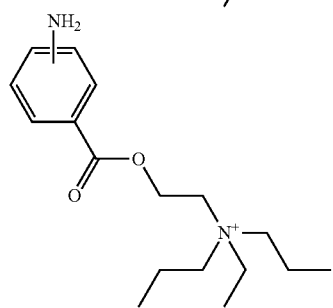
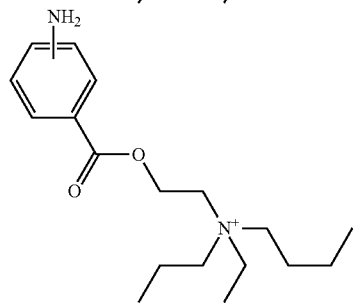
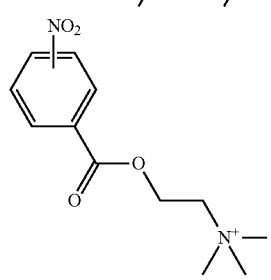
50
-continued
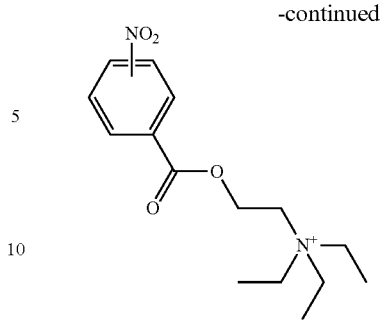
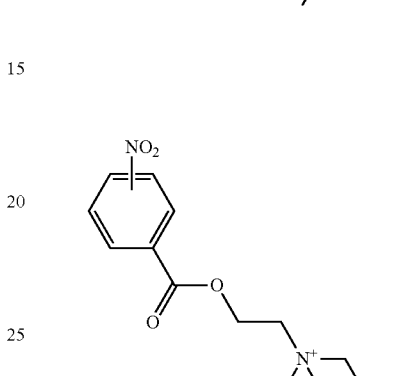
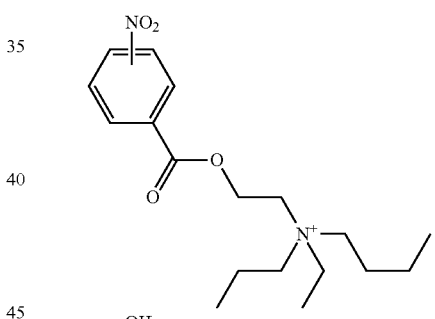
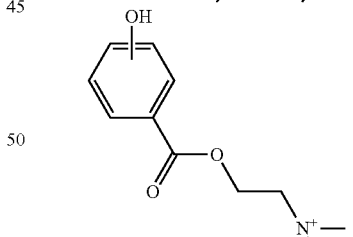
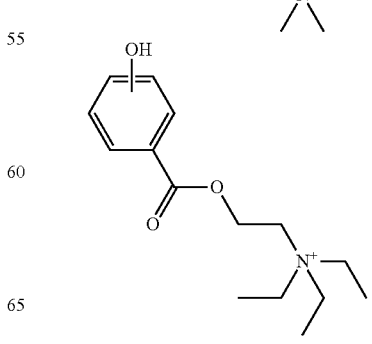

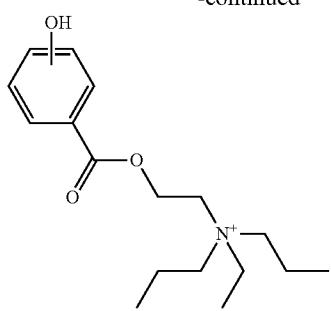
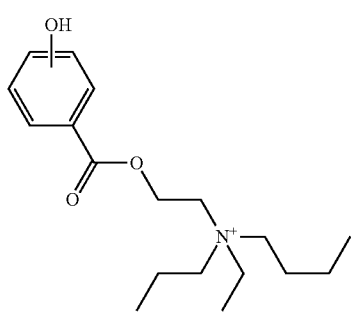
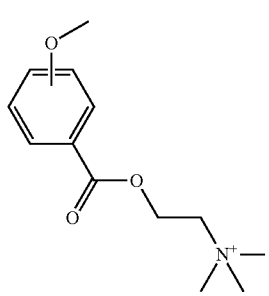
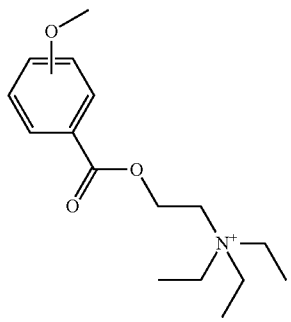
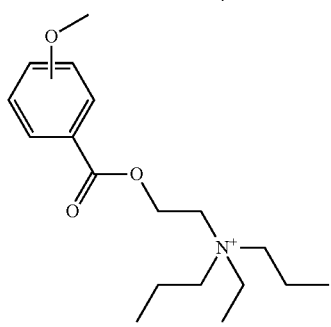
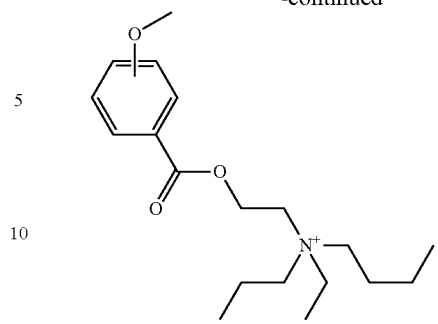
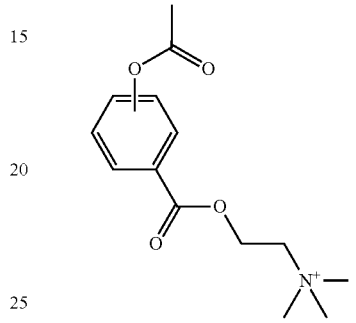
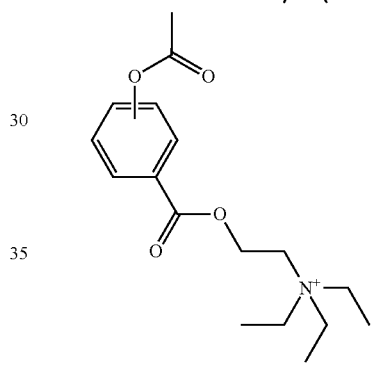
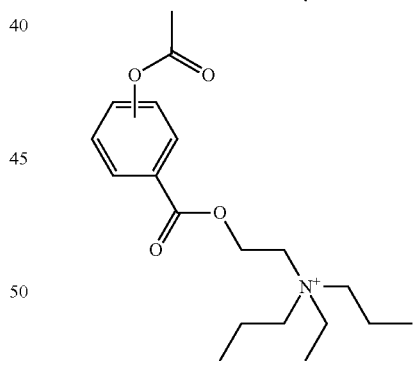
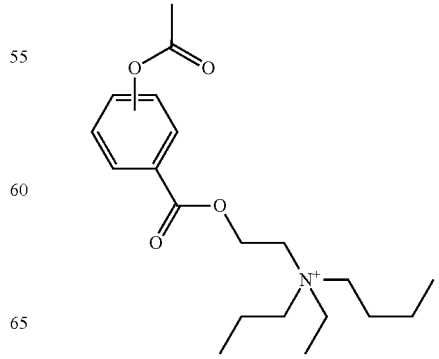

53
-continued
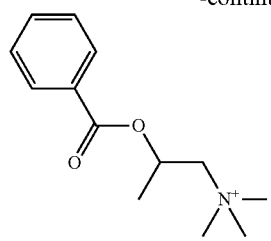
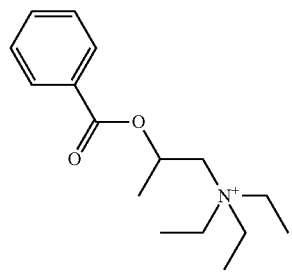
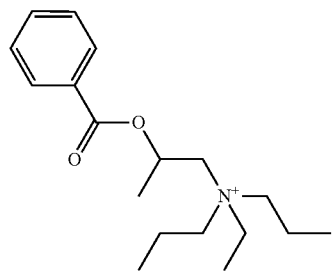
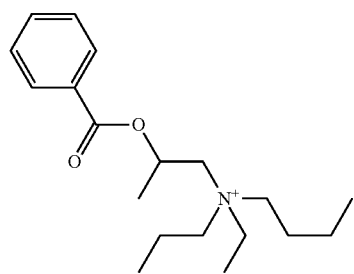
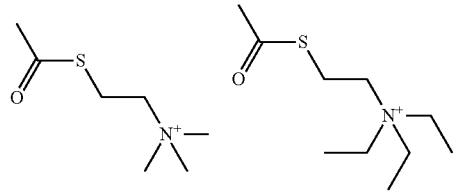
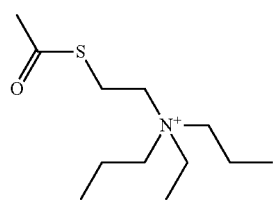
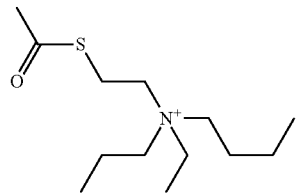
54
-continued
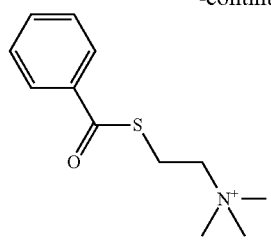
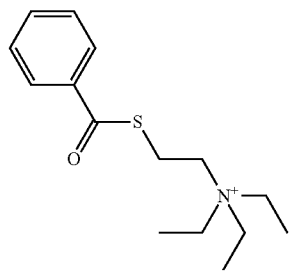
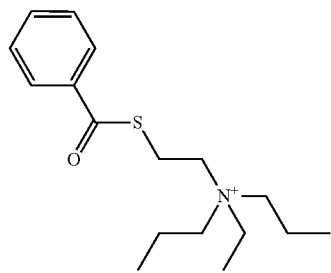
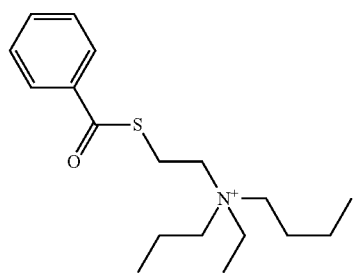
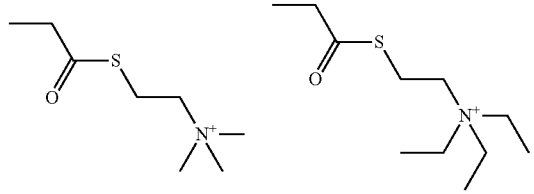
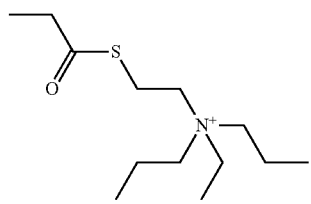
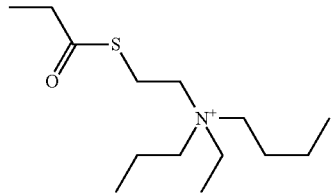

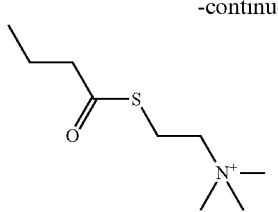
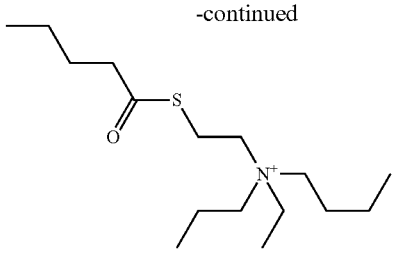
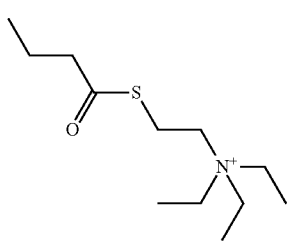
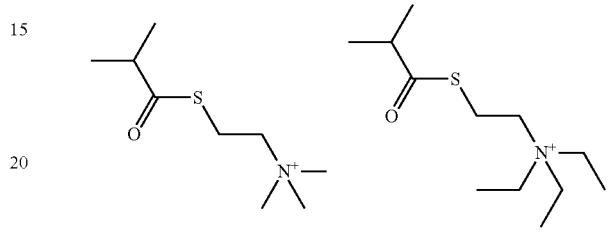
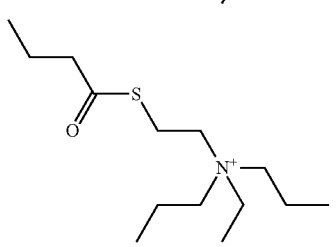
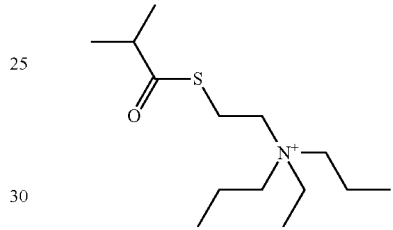
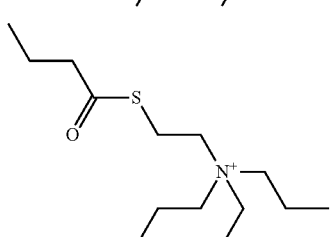
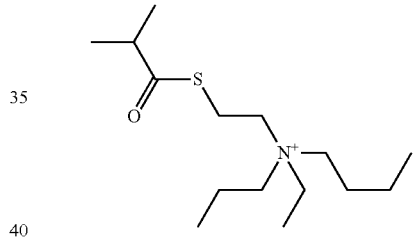
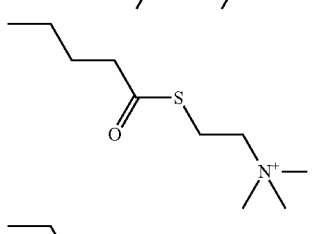
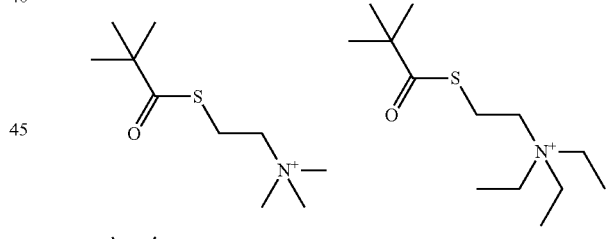
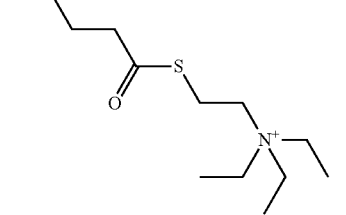
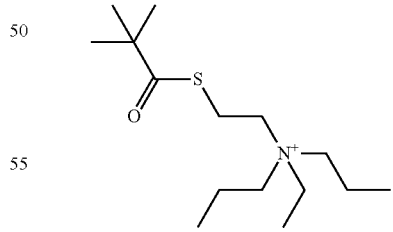
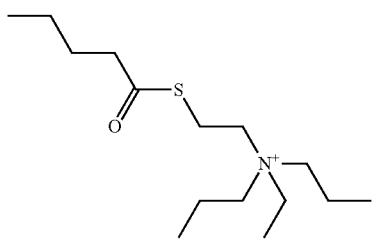
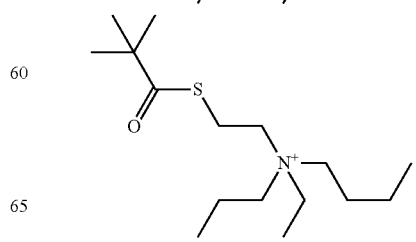

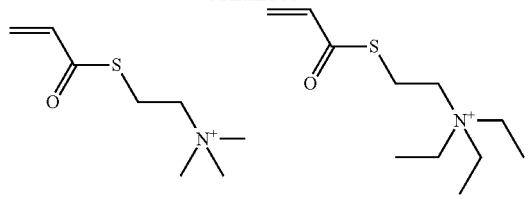
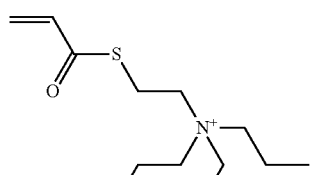
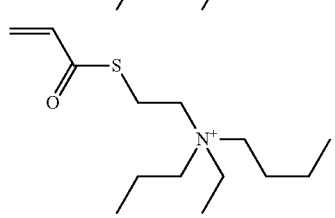
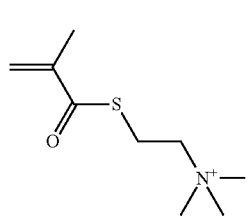
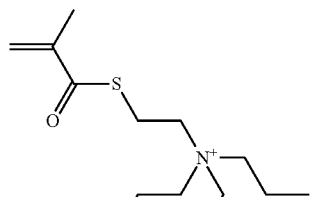
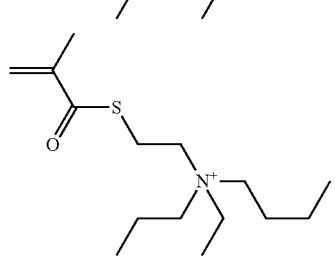
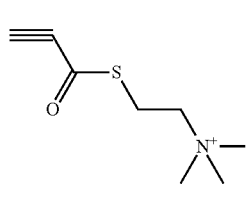
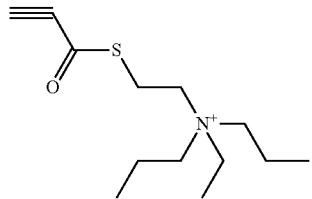
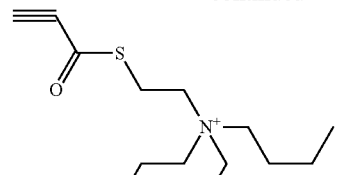
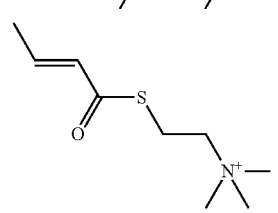
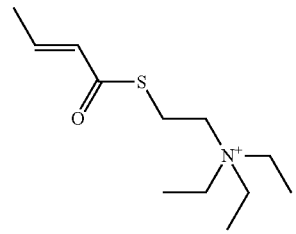
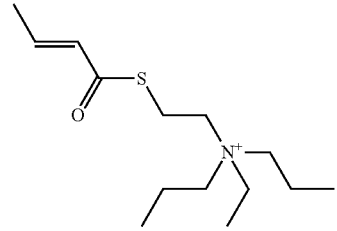
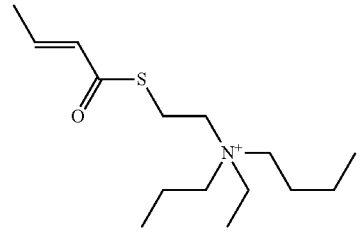
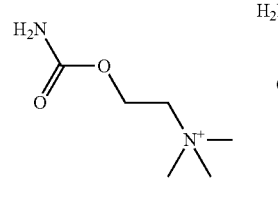
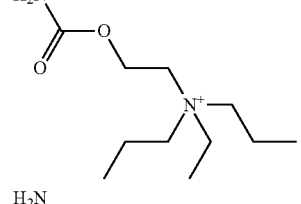
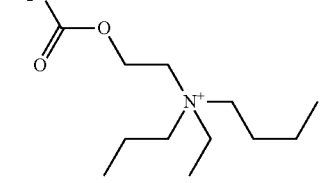

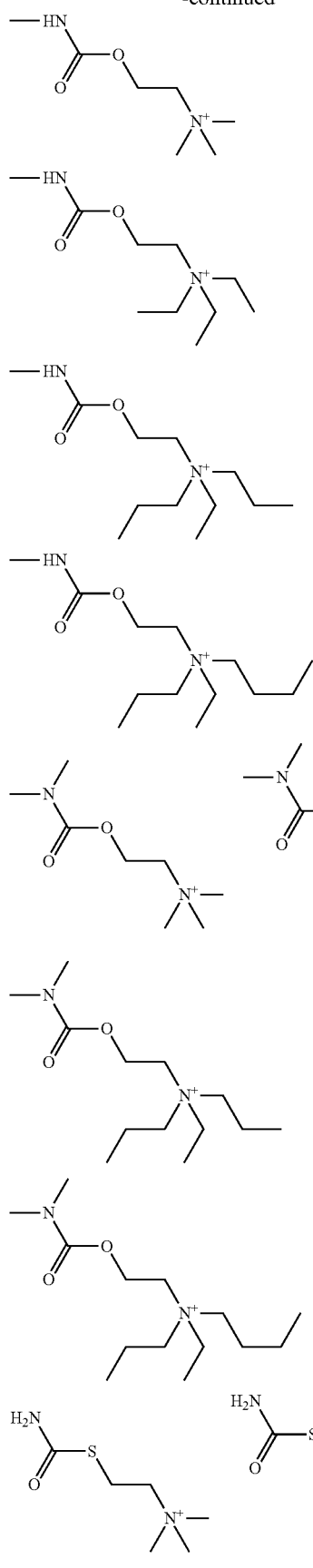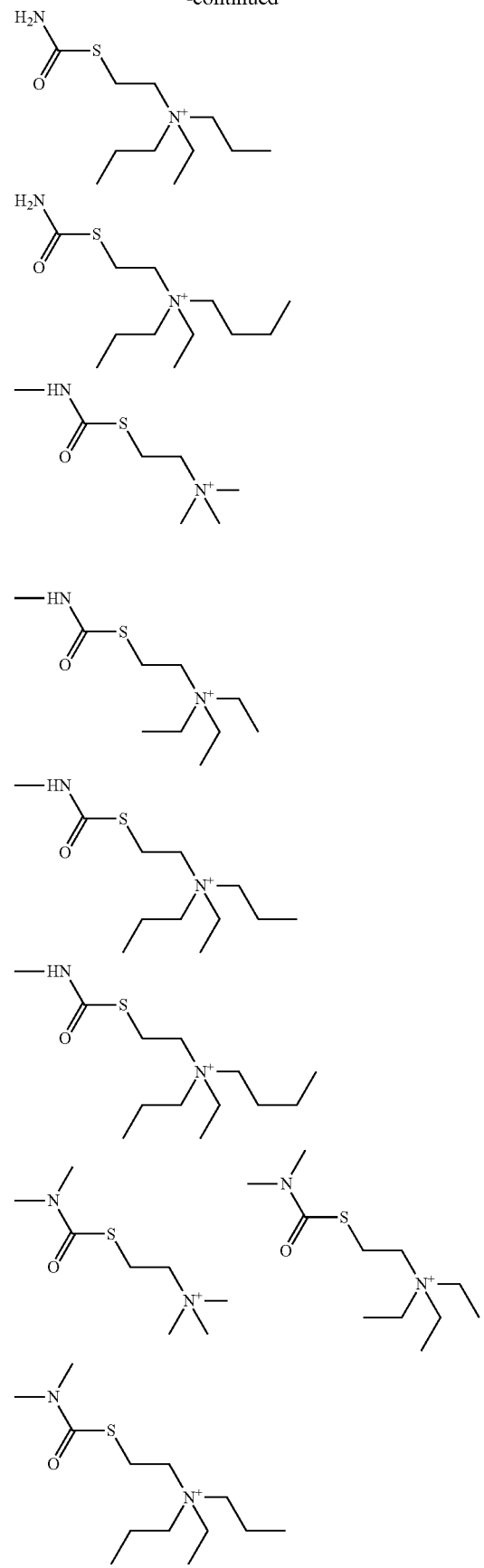

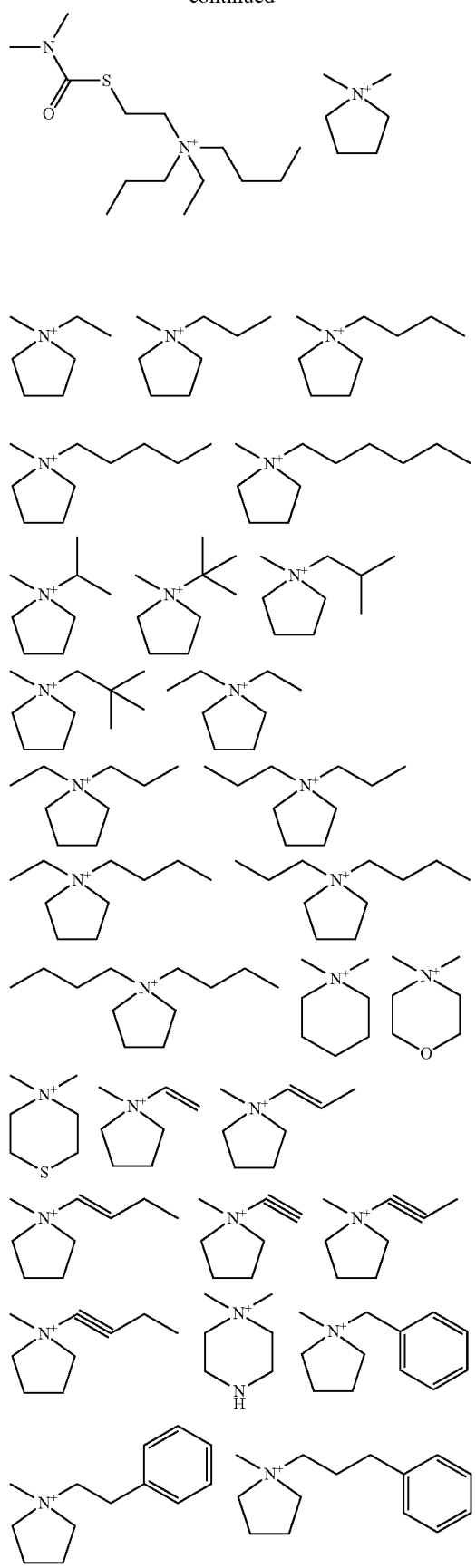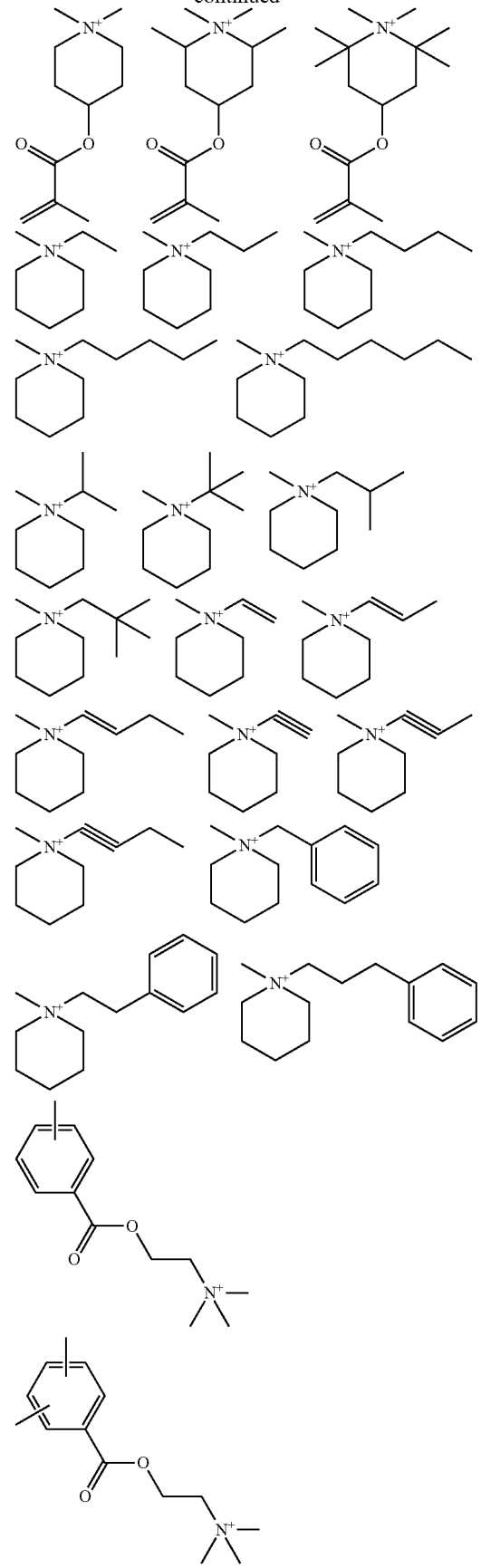

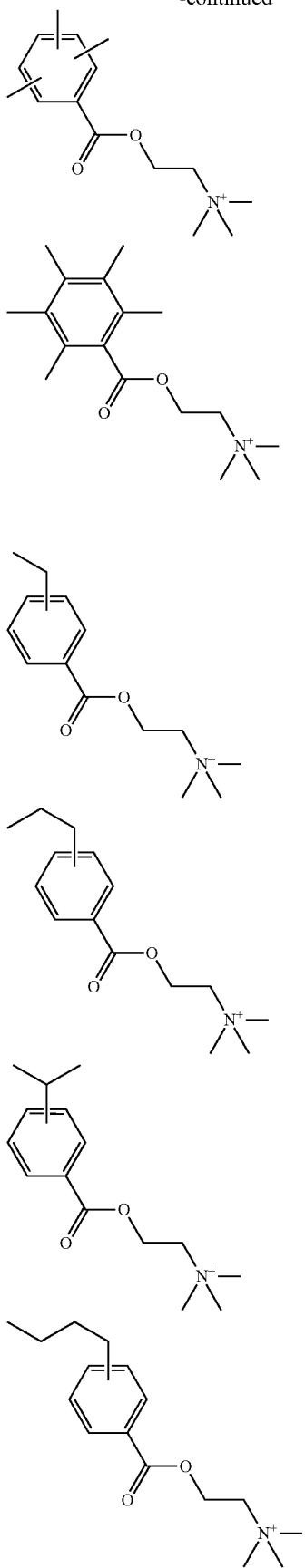
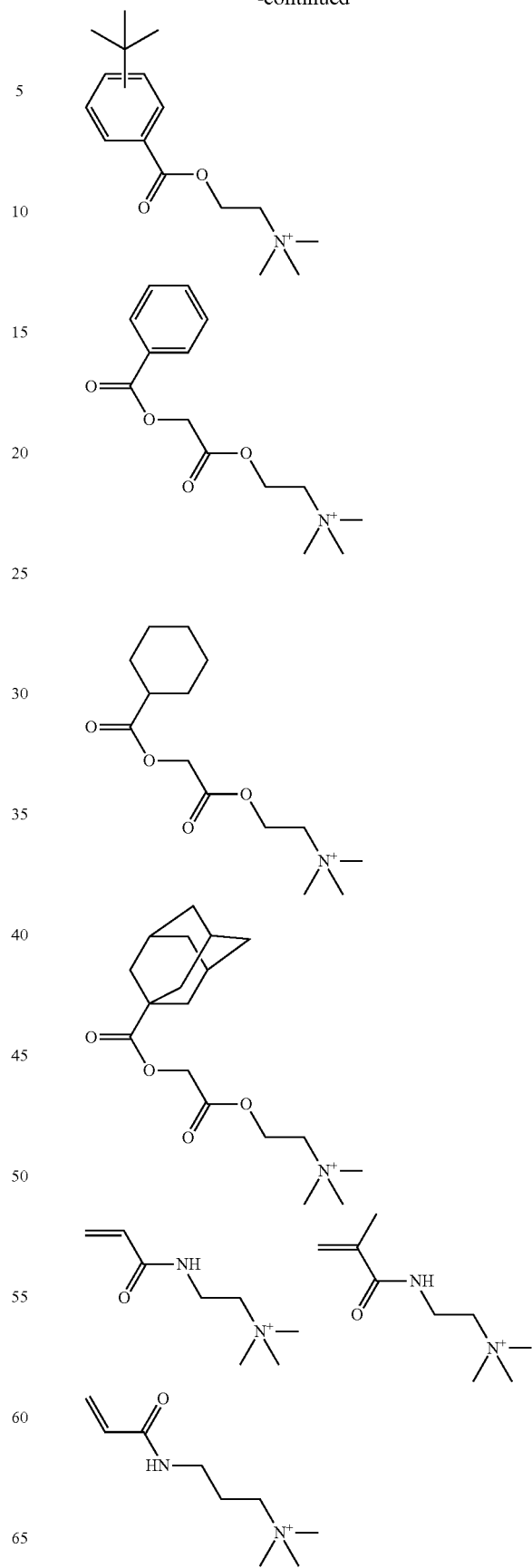

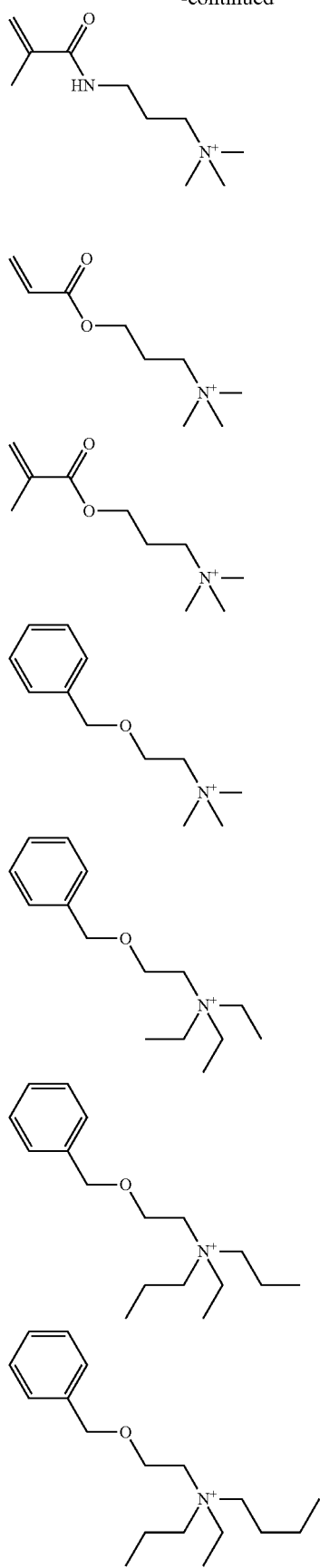
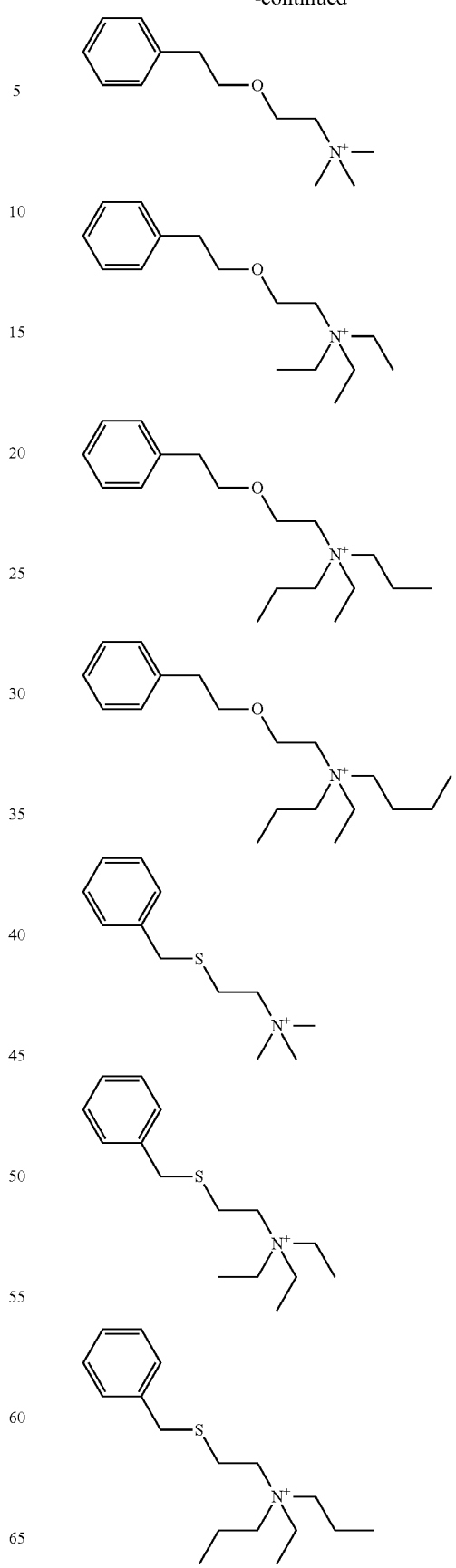

-continued

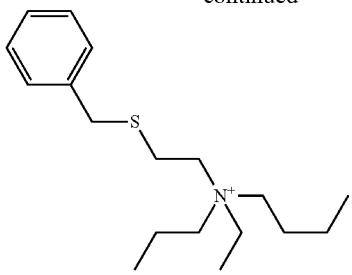

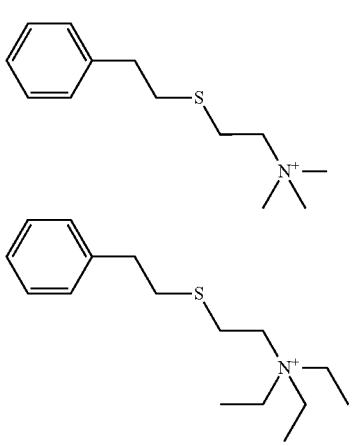

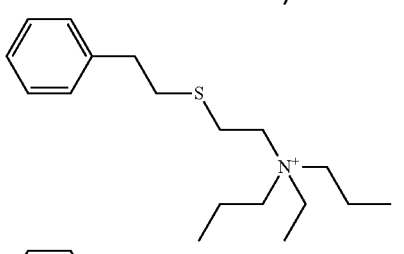

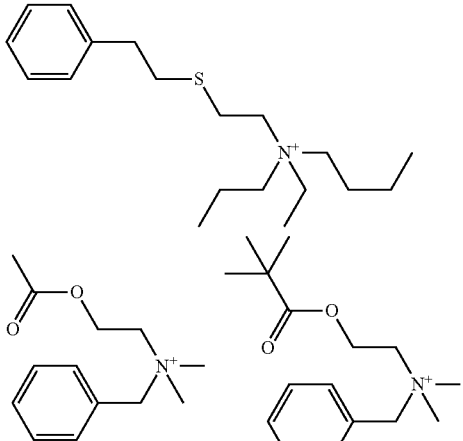

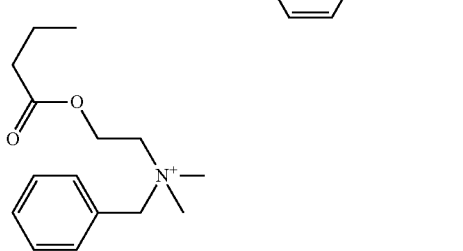

-continued

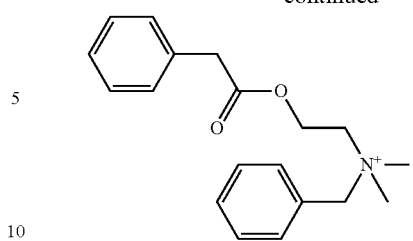

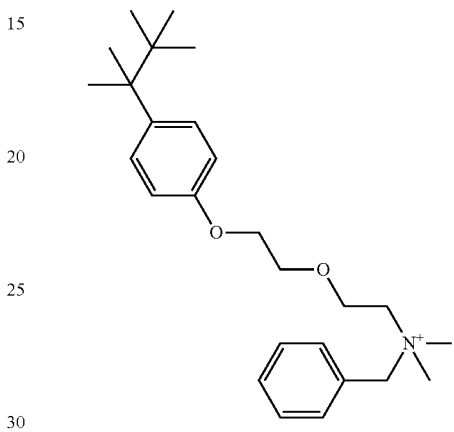

Particularly preferably, the ammonium ion represented by the general formula (3) is a tertiary or a quaternary ammonium ion.

Repeating Unit "b"

The component (A) of the bio-electrode composition of the present invention includes, in addition to the above repeating unit "a", a repeating unit "b" having a silicon atom. The repeating unit "b" is preferably a repeating unit "b1" in the general formula (2).

The monomer for obtaining the repeating unit "b1" in the general formula (2) is represented by the following general formula (5),

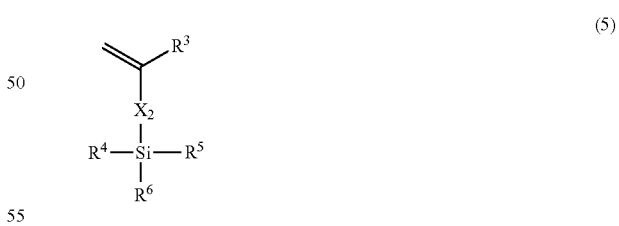

(5)

wherein, $R^3$ to $R^6$, and $X_2$ represent the same meanings as before.

Illustrative example of the monomer represented by the general formula (5) includes the following monomers,

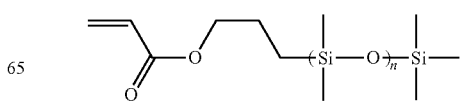

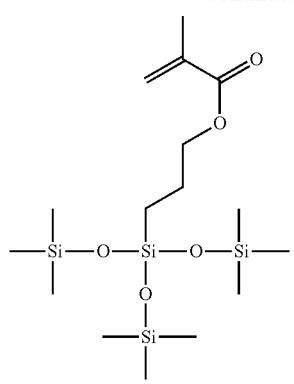
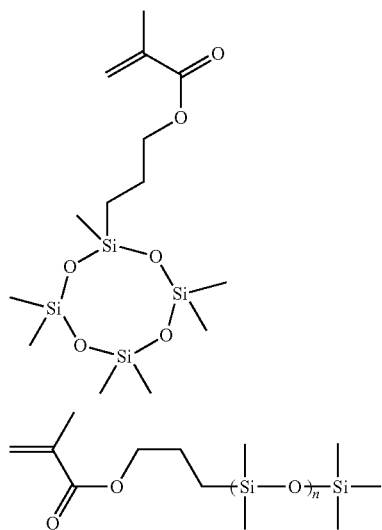
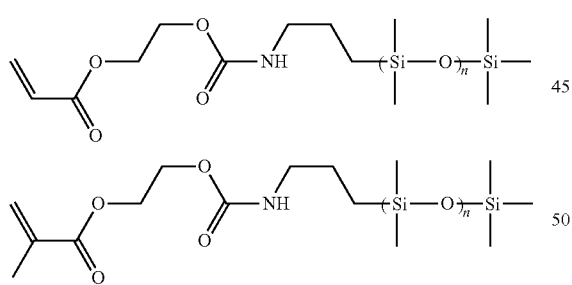
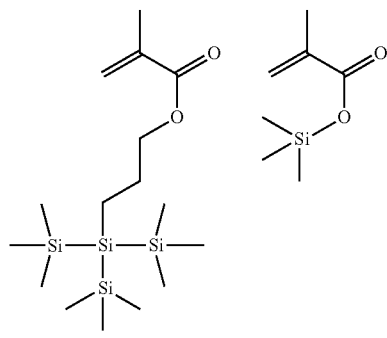
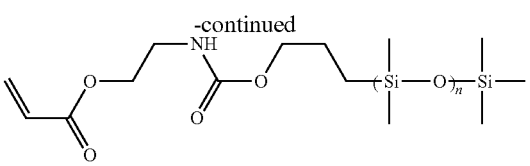
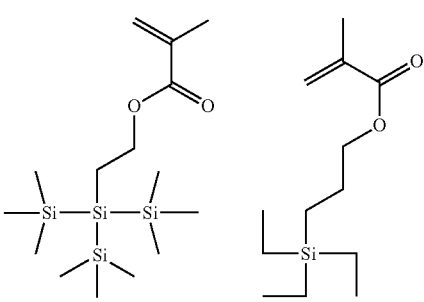
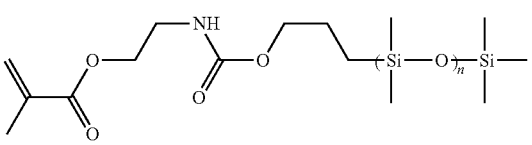
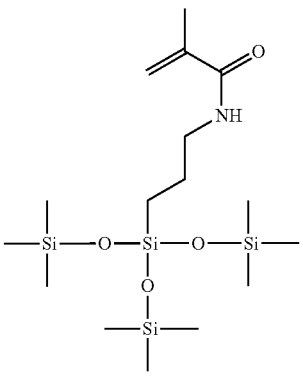
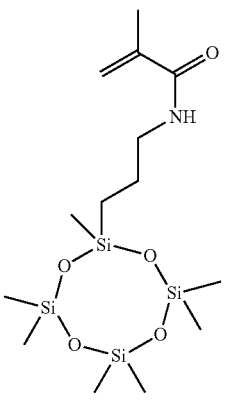

-continued

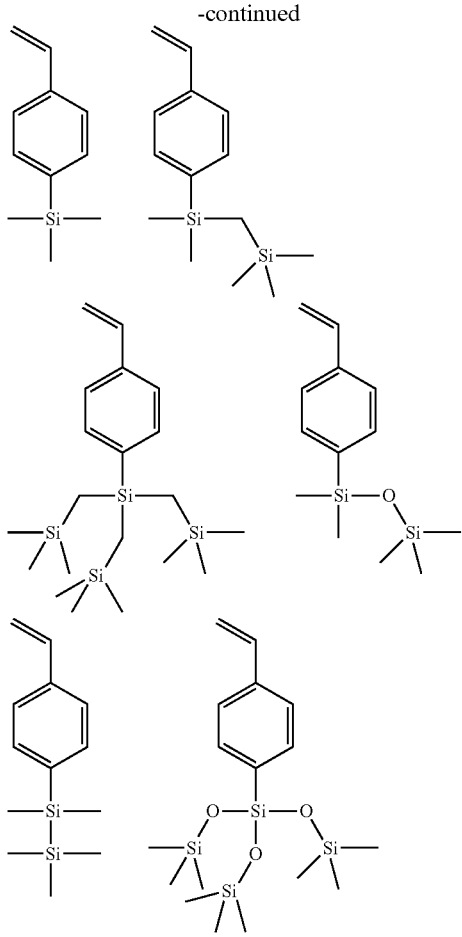

wherein, "n" is an integer of 0 to 100.

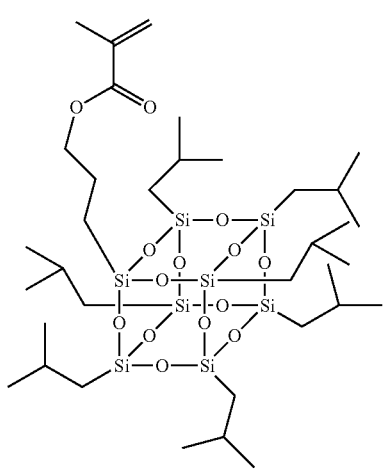

-continued

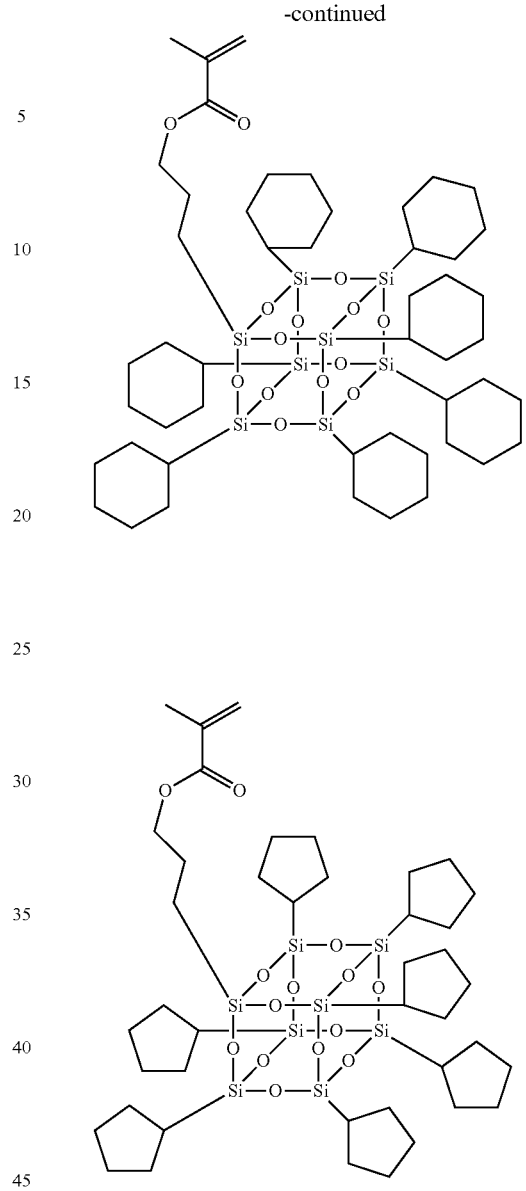

Repeating Unit "c"

The component (A) of the bio-electrode composition of the present invention can be copolymerized with a monomer having two polymerizable double bonds in one molecule (repeating unit "c"), in addition to the repeating units "a" and "b". The use of such a repeating unit "c" can improve the crosslinking property of the component (A).

Illustrative example of the monomer for obtaining a repeating unit "c" includes the following monomers,

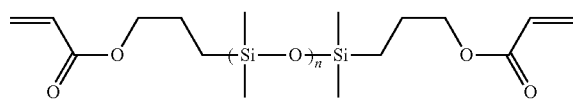

-continued

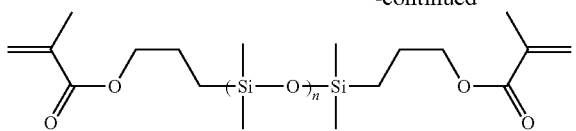

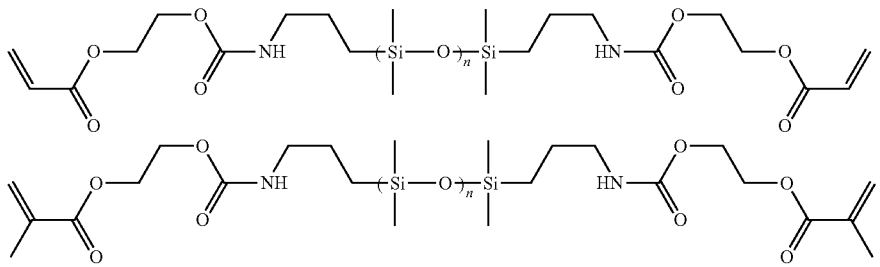

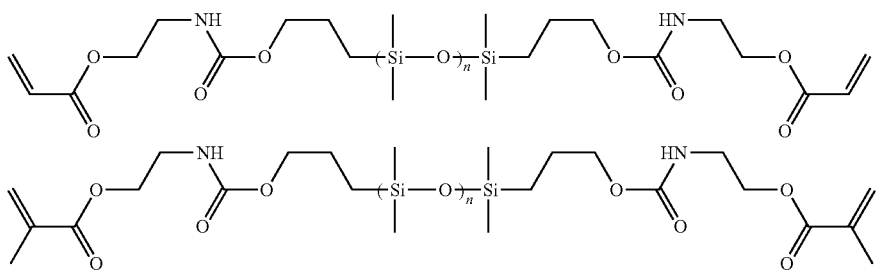

wherein, "n" is an integer of 0 to 100.

Repeating Unit "d"

The component (A) of the bio-electrode composition of the present invention can be copolymerized with a monomer having an oxymethylene structure, an oxyethylene structure (glyme chain), or an oxypropylene structure (repeating unit "d"), in addition to the repeating units "a" and "b". The use of such a repeating unit "d" can improve the conductivity of the component (A).

Illustrative example of the monomer for obtaining a repeating unit "d" includes the one represented by the following general formula (2)",

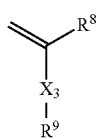

(2)"

wherein, $R^8$ represents a hydrogen atom or a methyl group; $X_3$ represents any of a single bond, a phenylene group, a naphthylene group, ether group, an ester group, a phenylene group having an ester group, or an amide group, $R^9$ represents a linear, or a branched alkylene group having 1 to 80 carbon atoms, having at least one ether group, and may include an aromatic group.

Illustrative example of the monomer for obtaining a repeating unit "d" includes the following monomers,

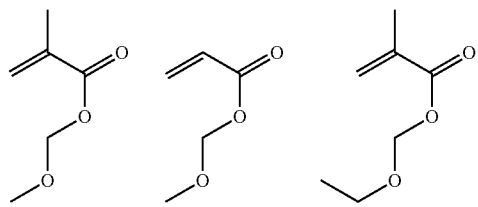

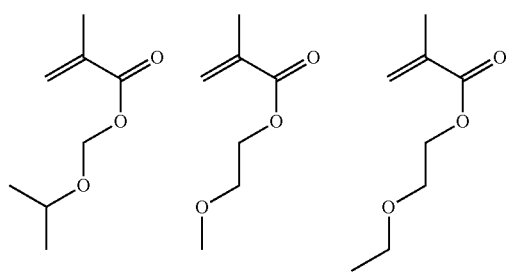

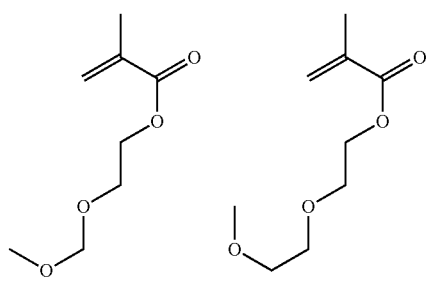

75
-continued
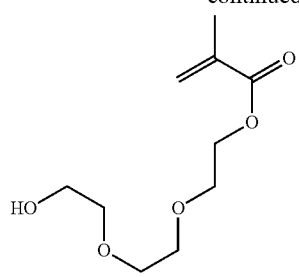
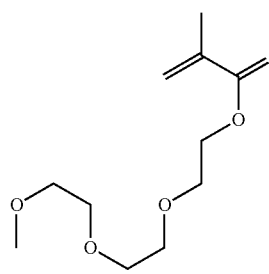
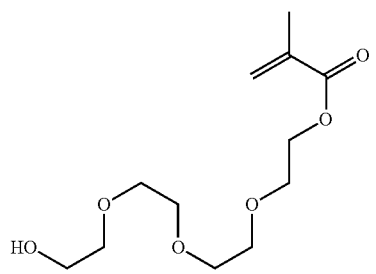
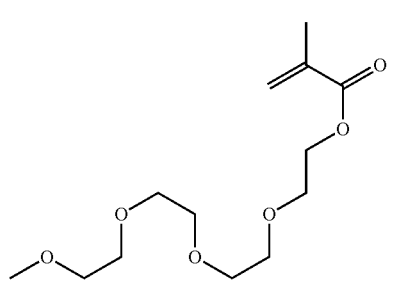
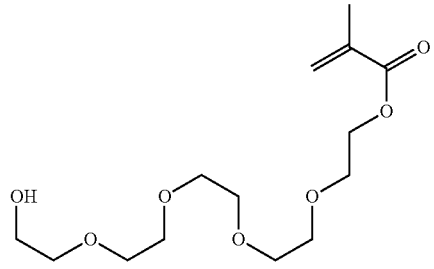
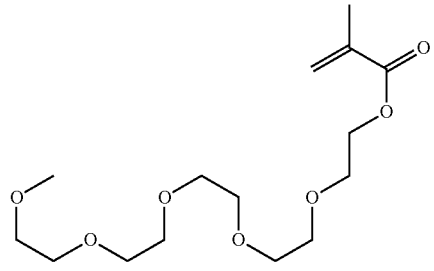
76
-continued
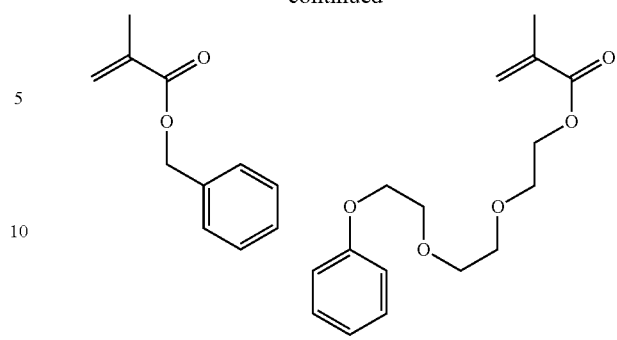
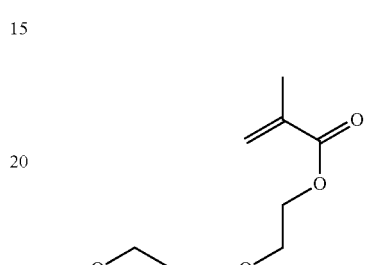
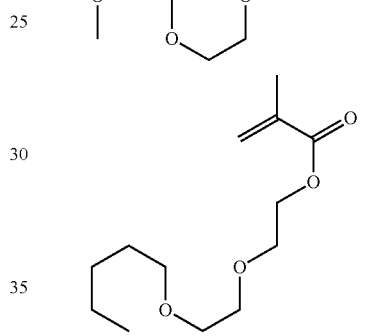
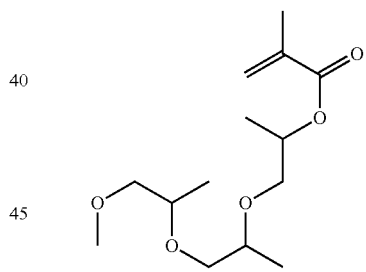
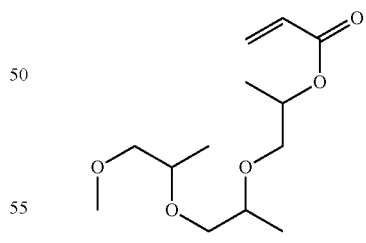
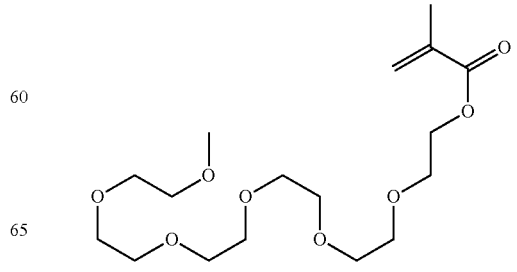

77
-continued
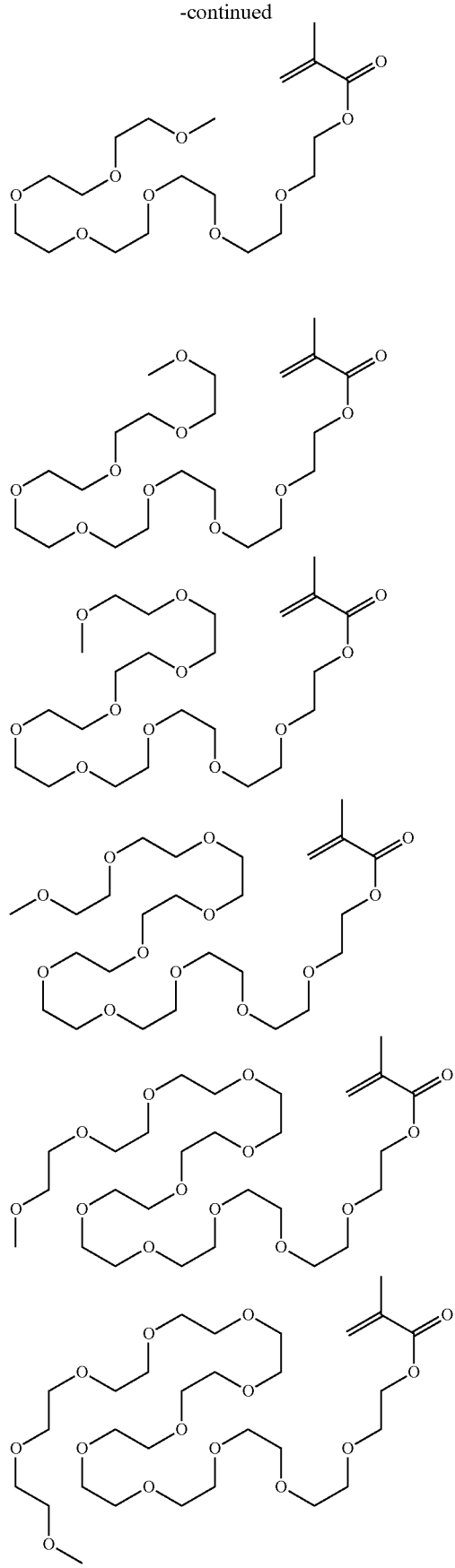
78
-continued
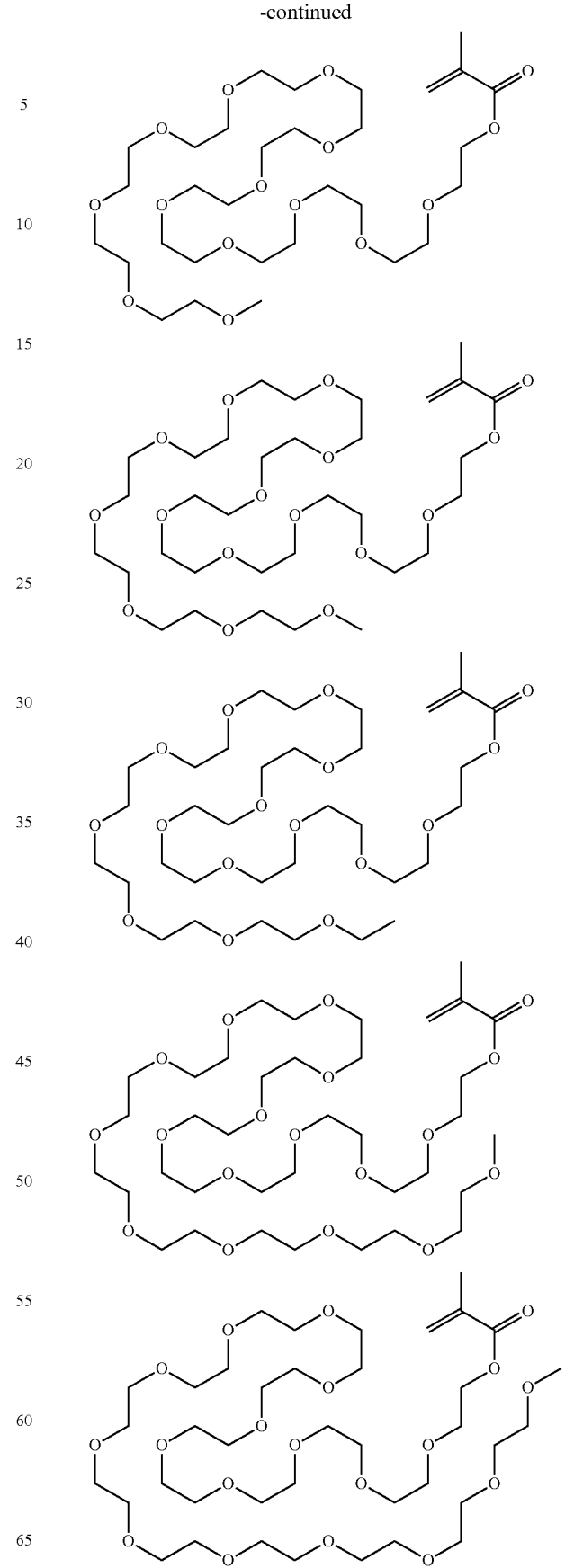

79
-continued
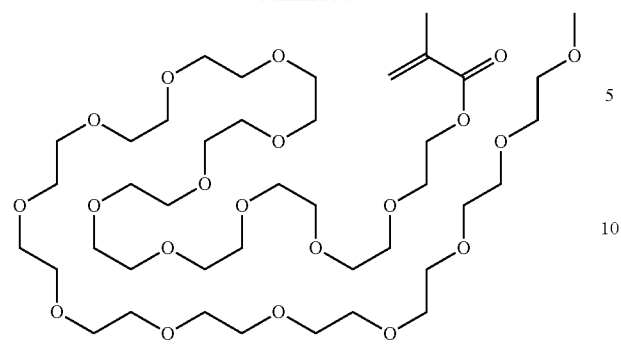
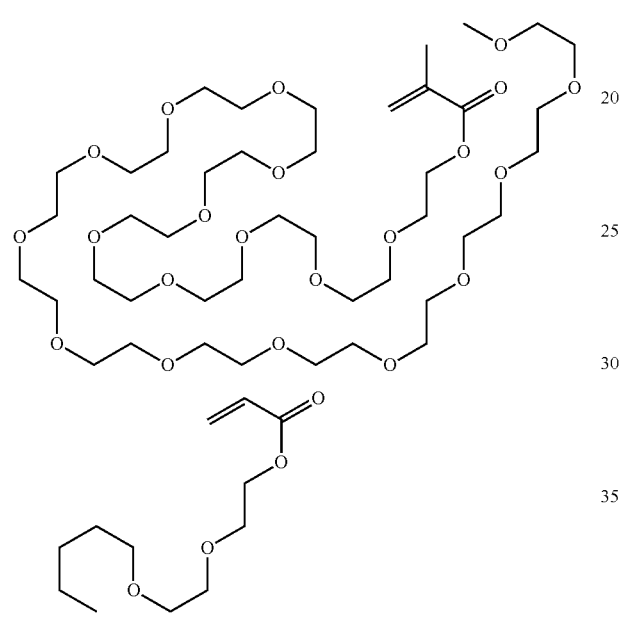
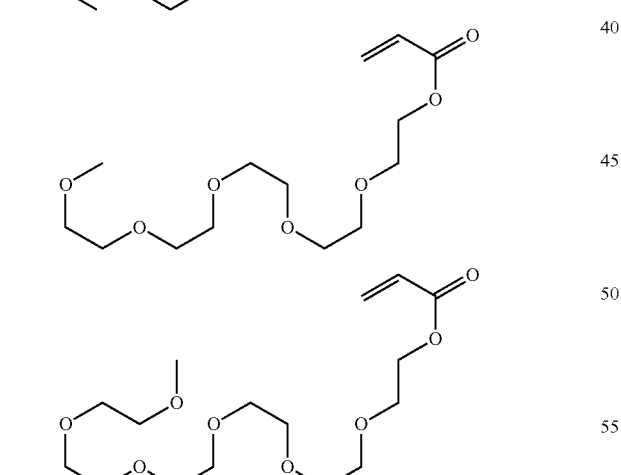
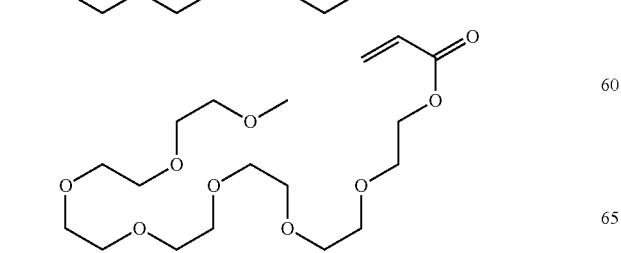
80
-continued
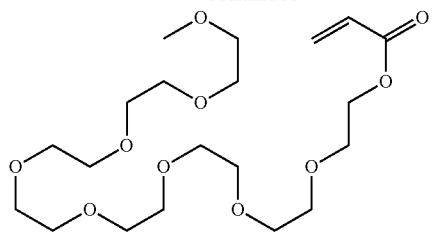
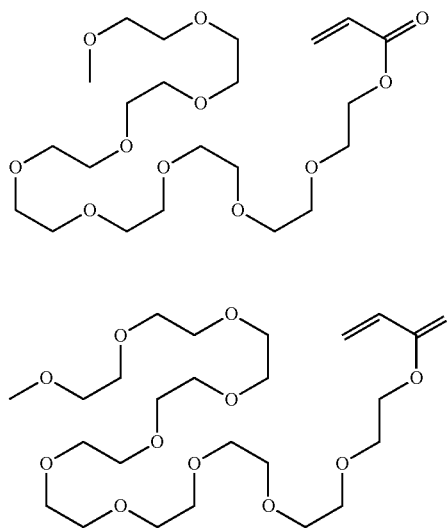
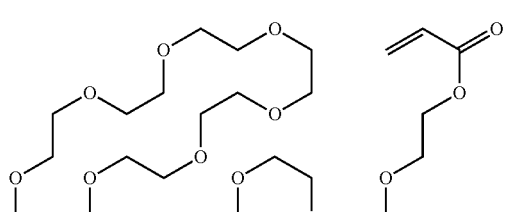
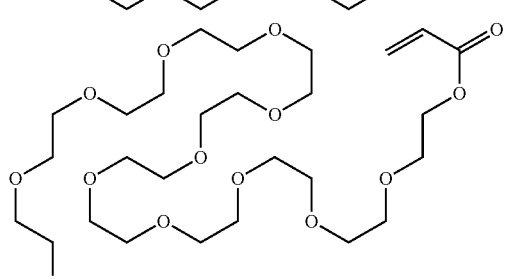
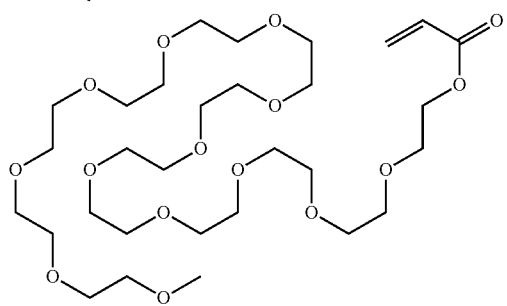

81

82

83
-continued
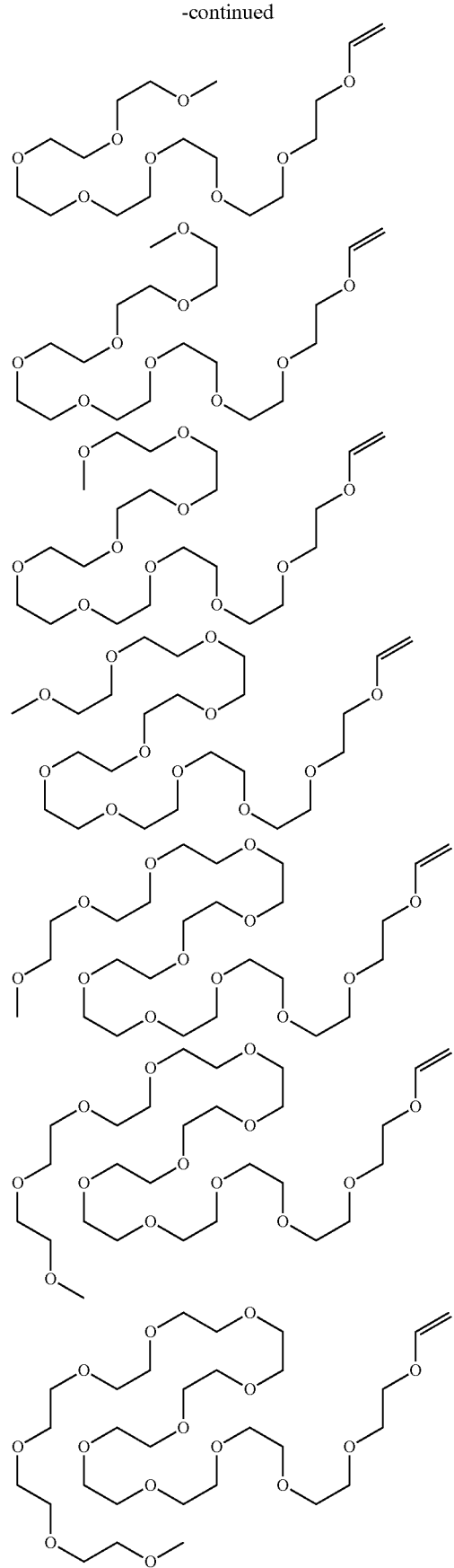
84
-continued
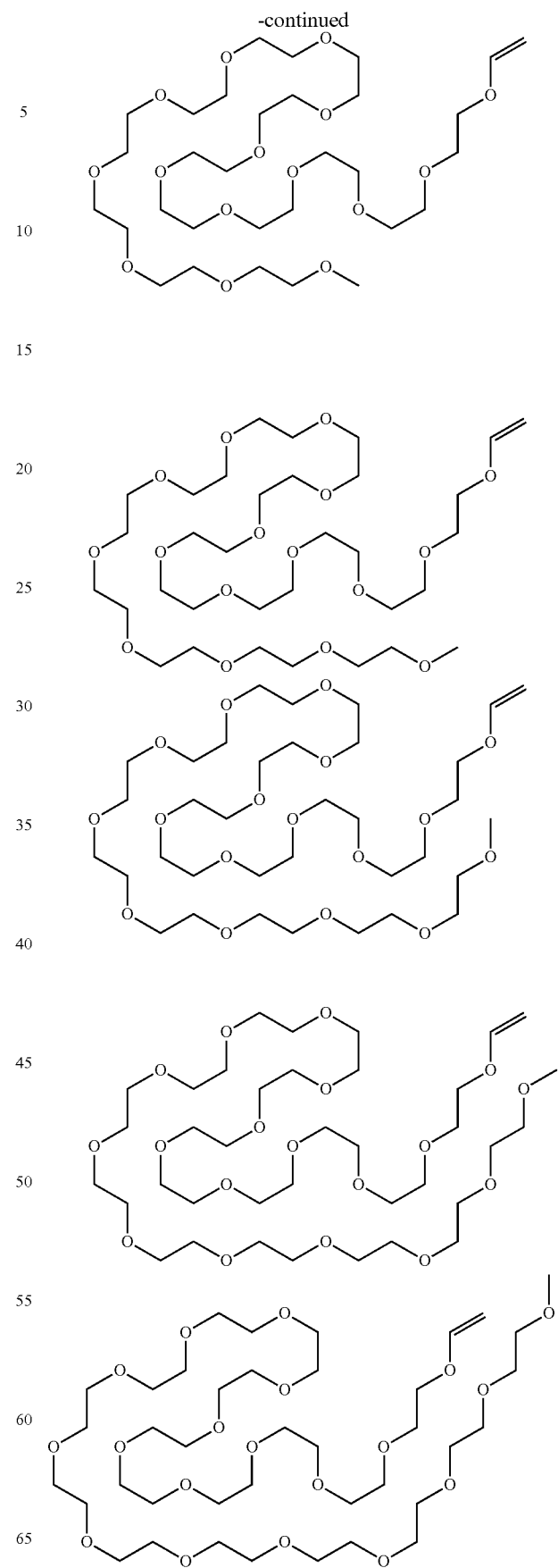

85
-continued
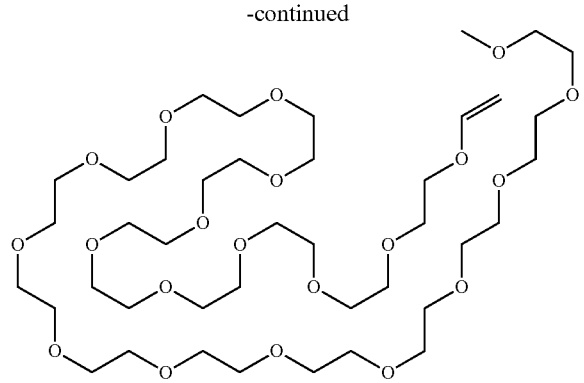
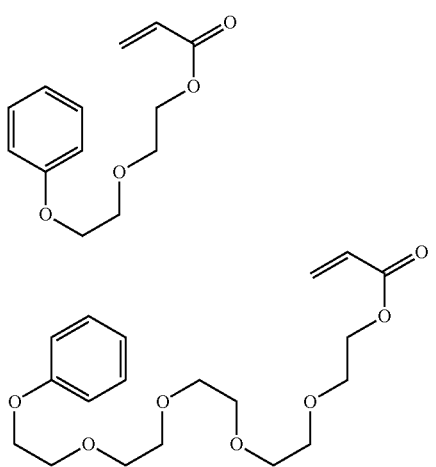
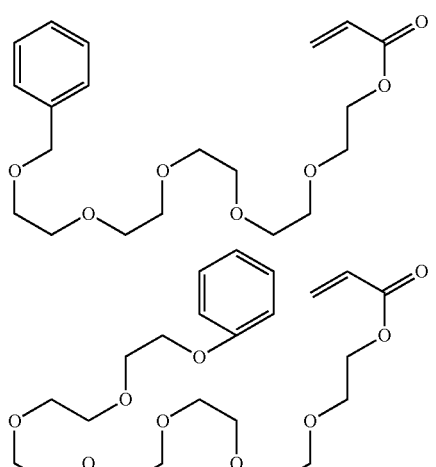
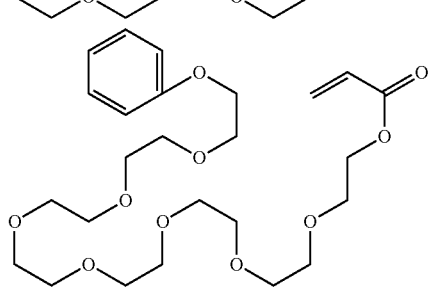
86
-continued
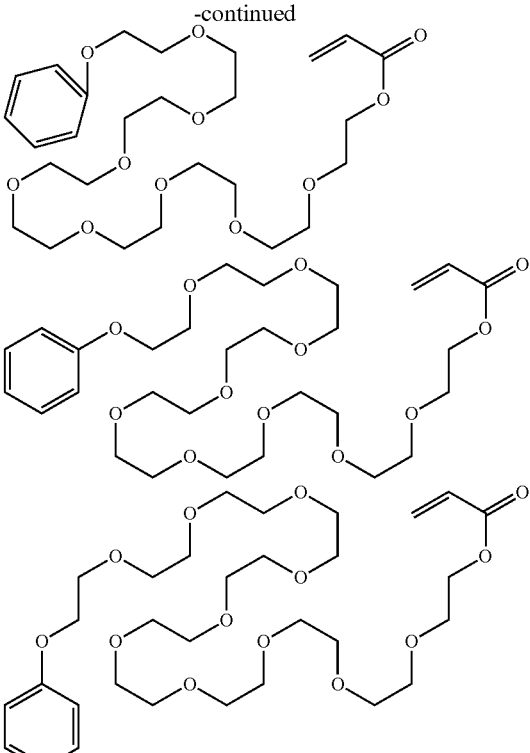
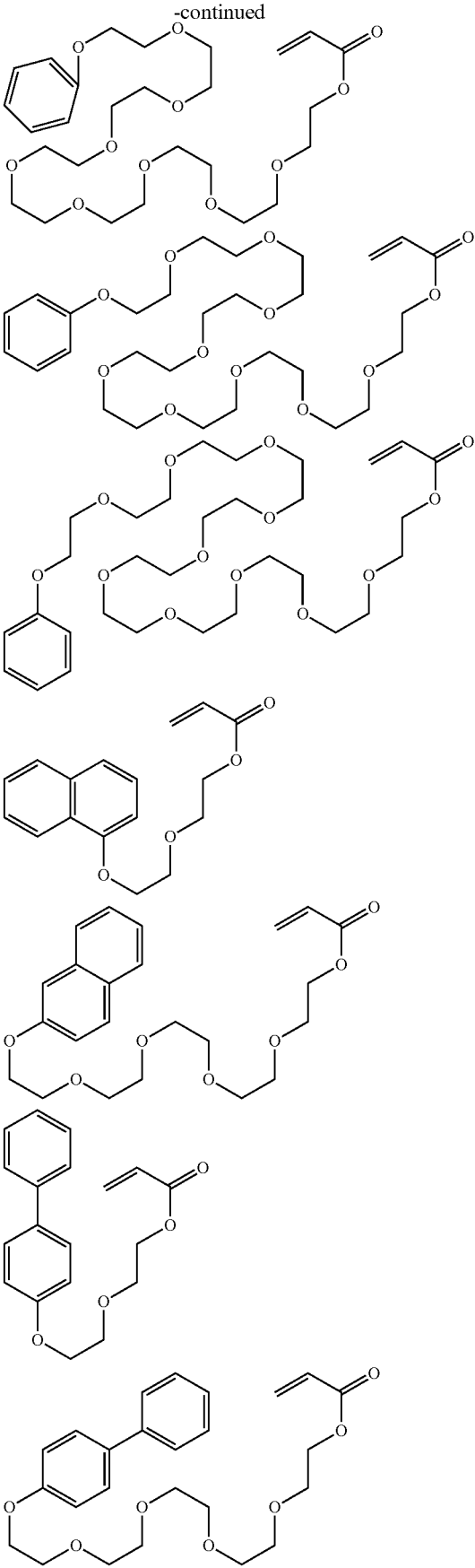

87
-continued
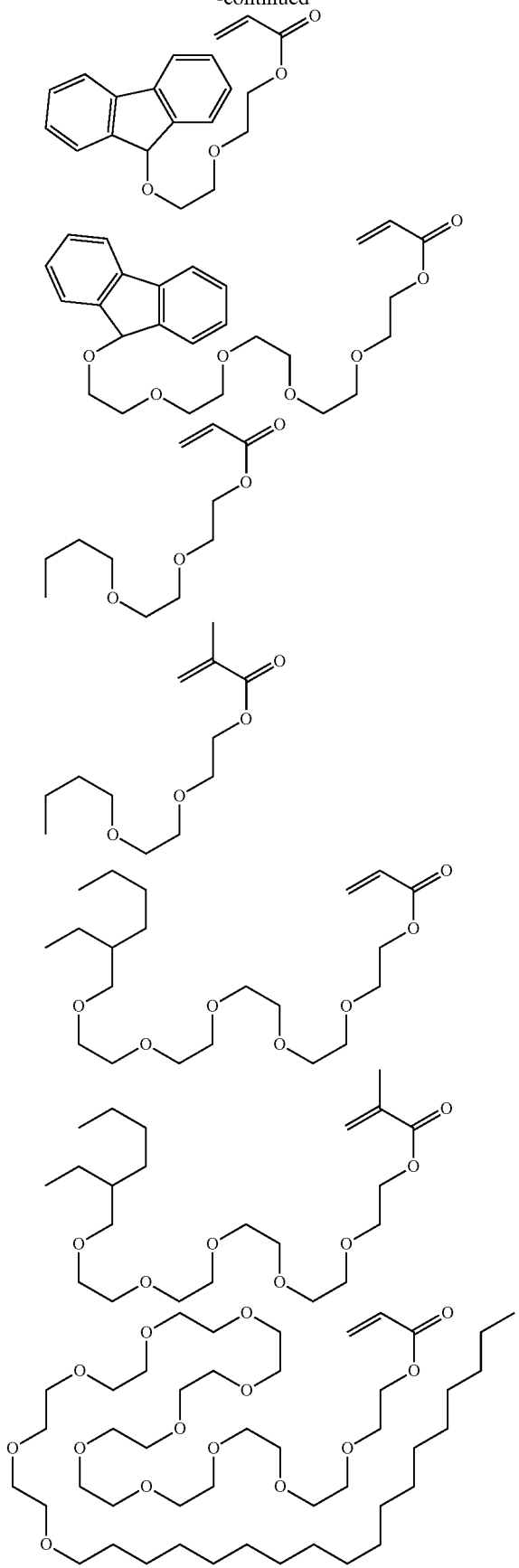
88
-continued
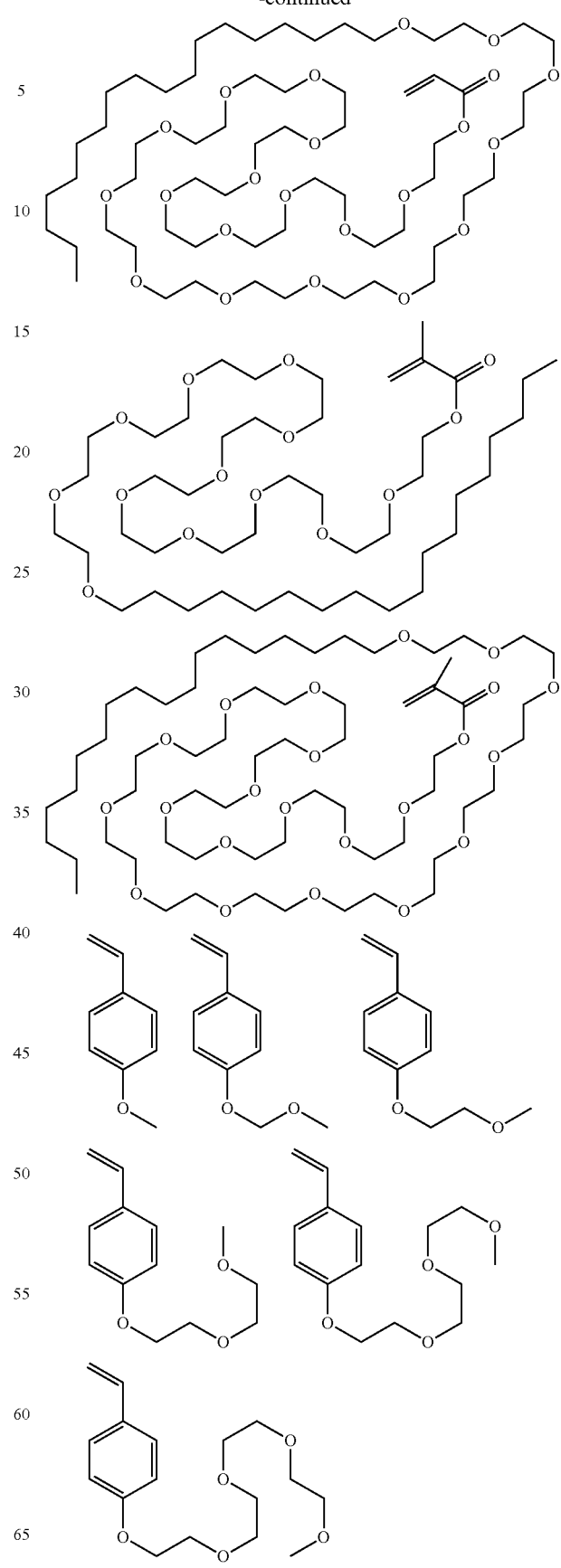

-continued

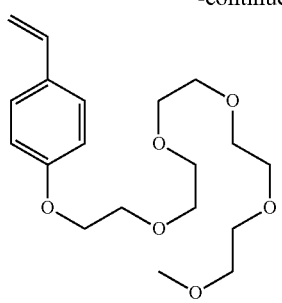

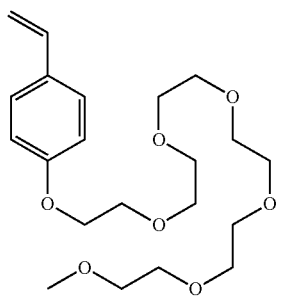

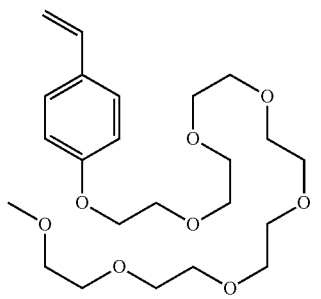

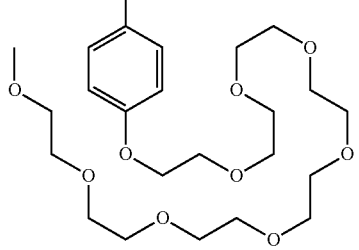

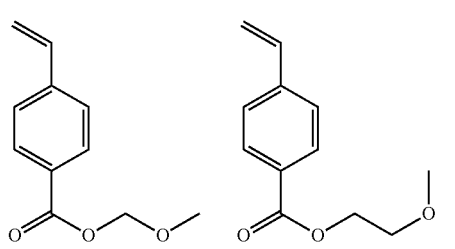

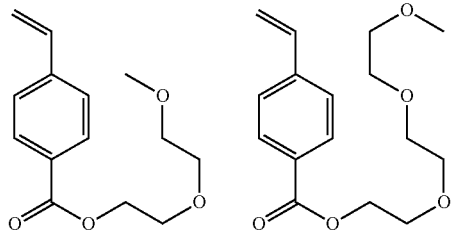

-continued

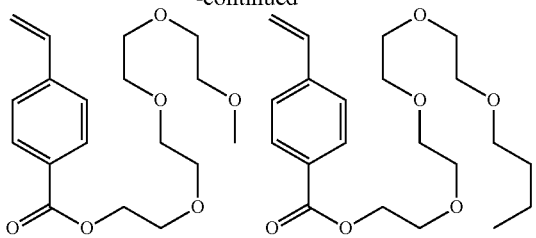

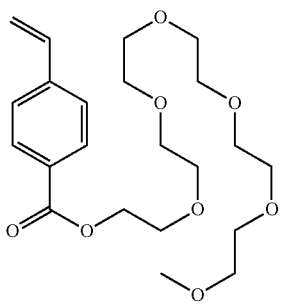

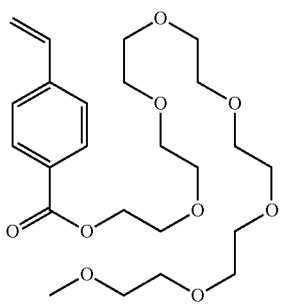

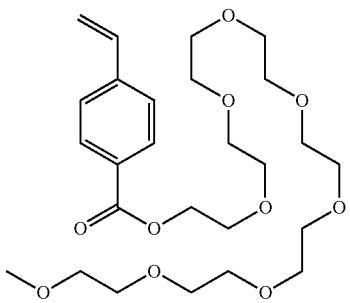

Repeating Unit "e"

The component (A) of the bio-electrode composition of the present invention can be copolymerized with a monomer containing a glyme chain having two polymerizable double bonds in one molecule (repeating unit "e"), in addition to the repeating units "a", "b", "c", and "d". The use of such a repeating unit "e" can improve the crosslinking property and ion conductivity of the component (A).

Illustrative example of the monomer for obtaining a repeating unit "e" includes the following monomers,

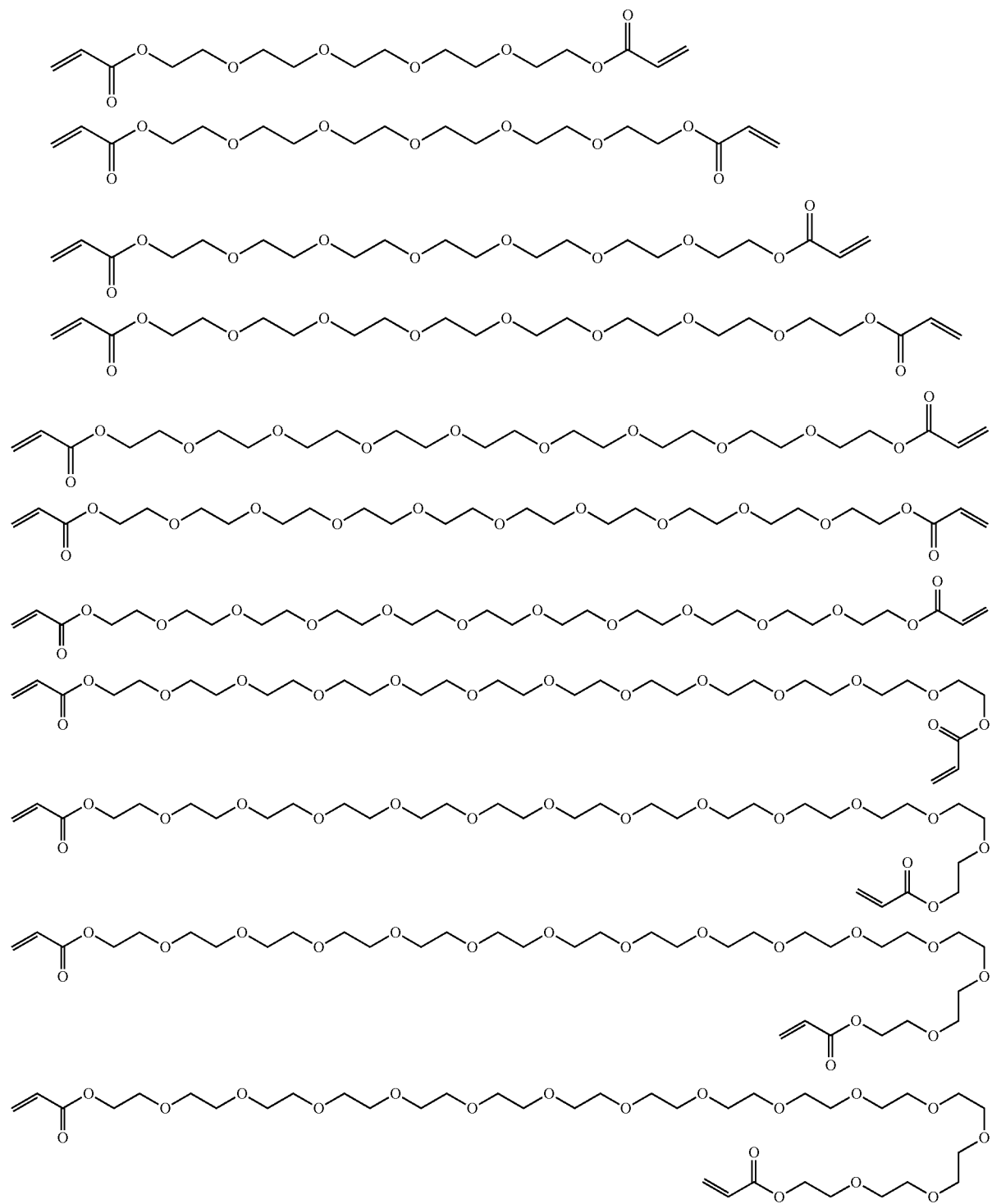

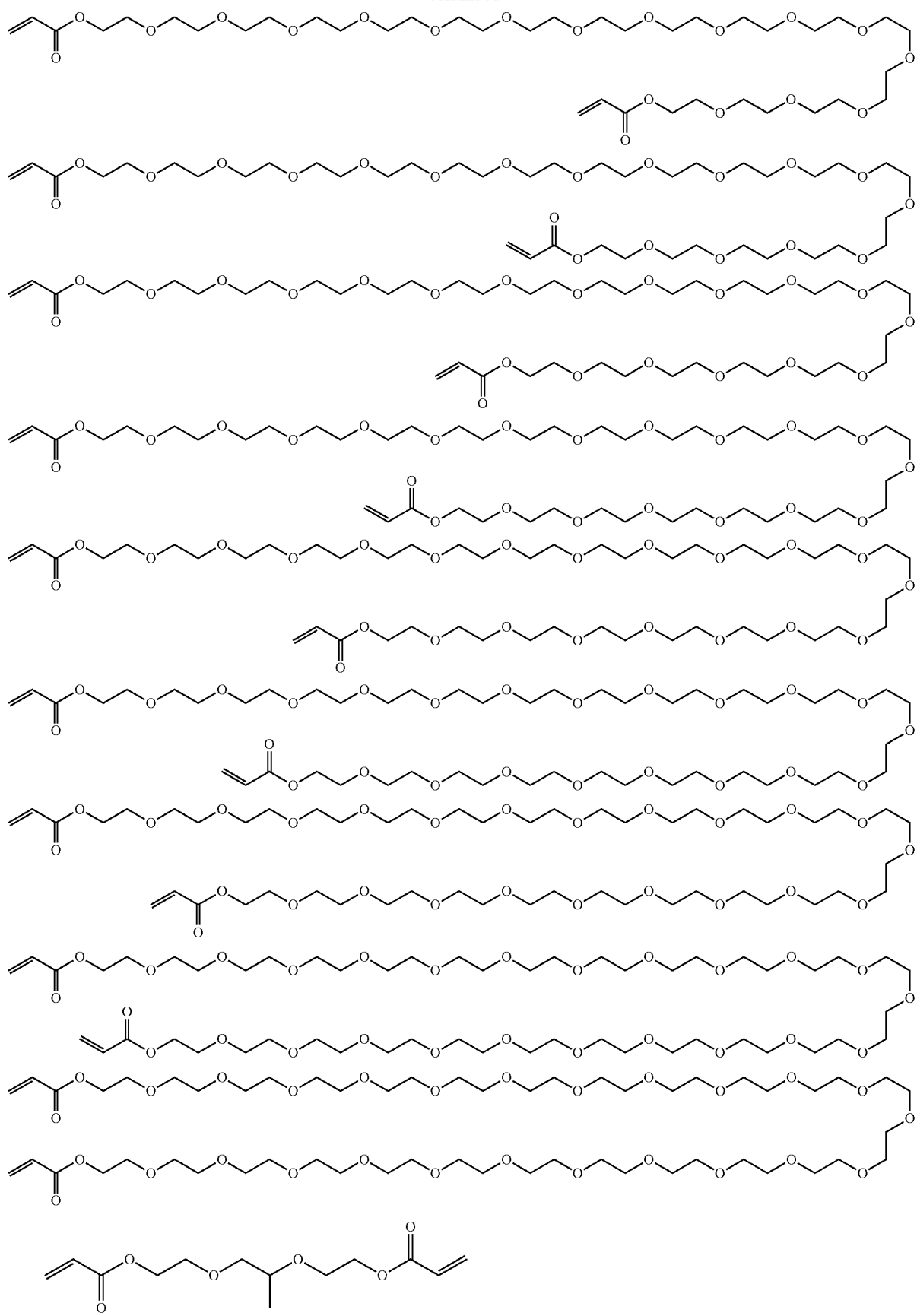

-continued
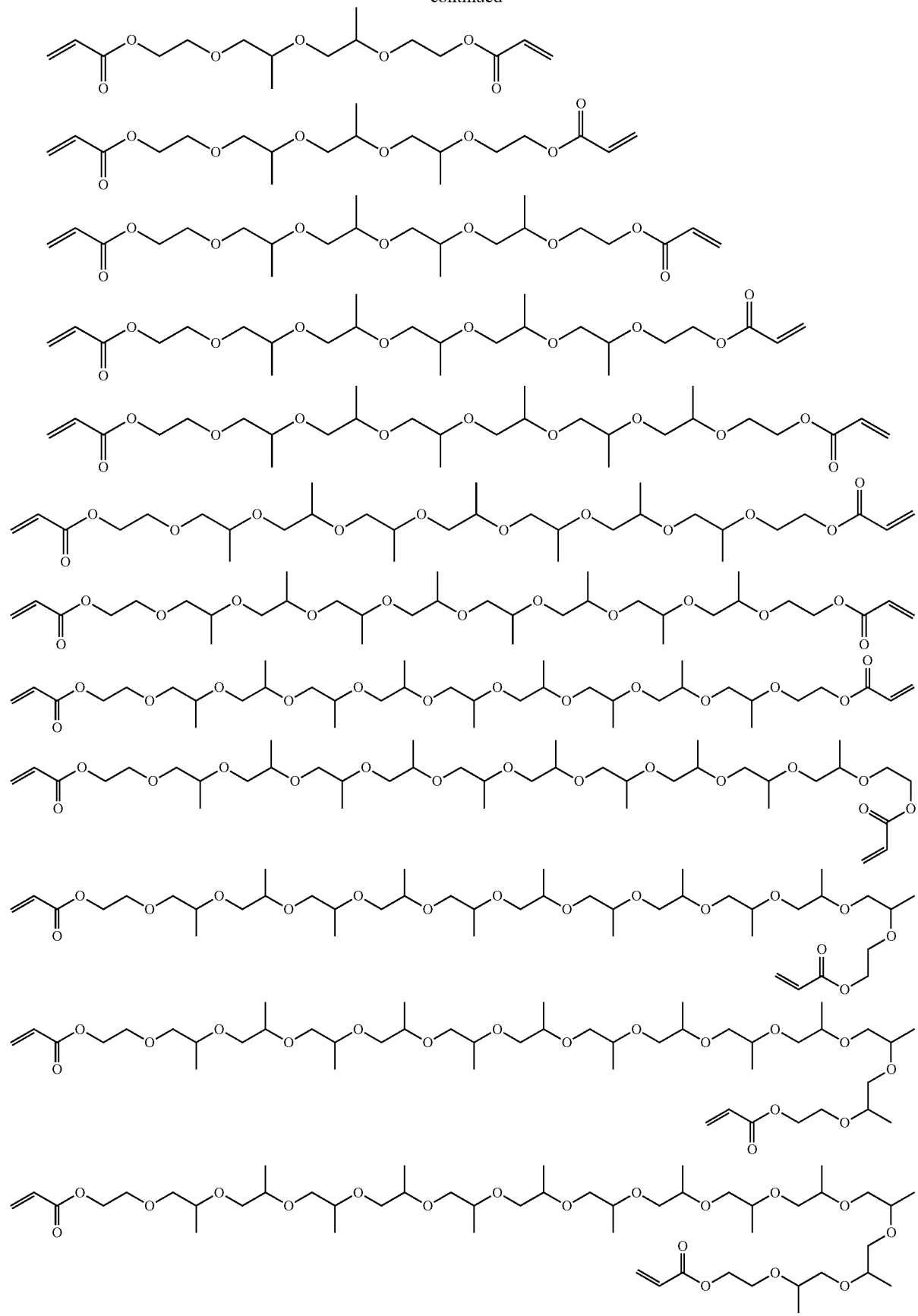

-continued
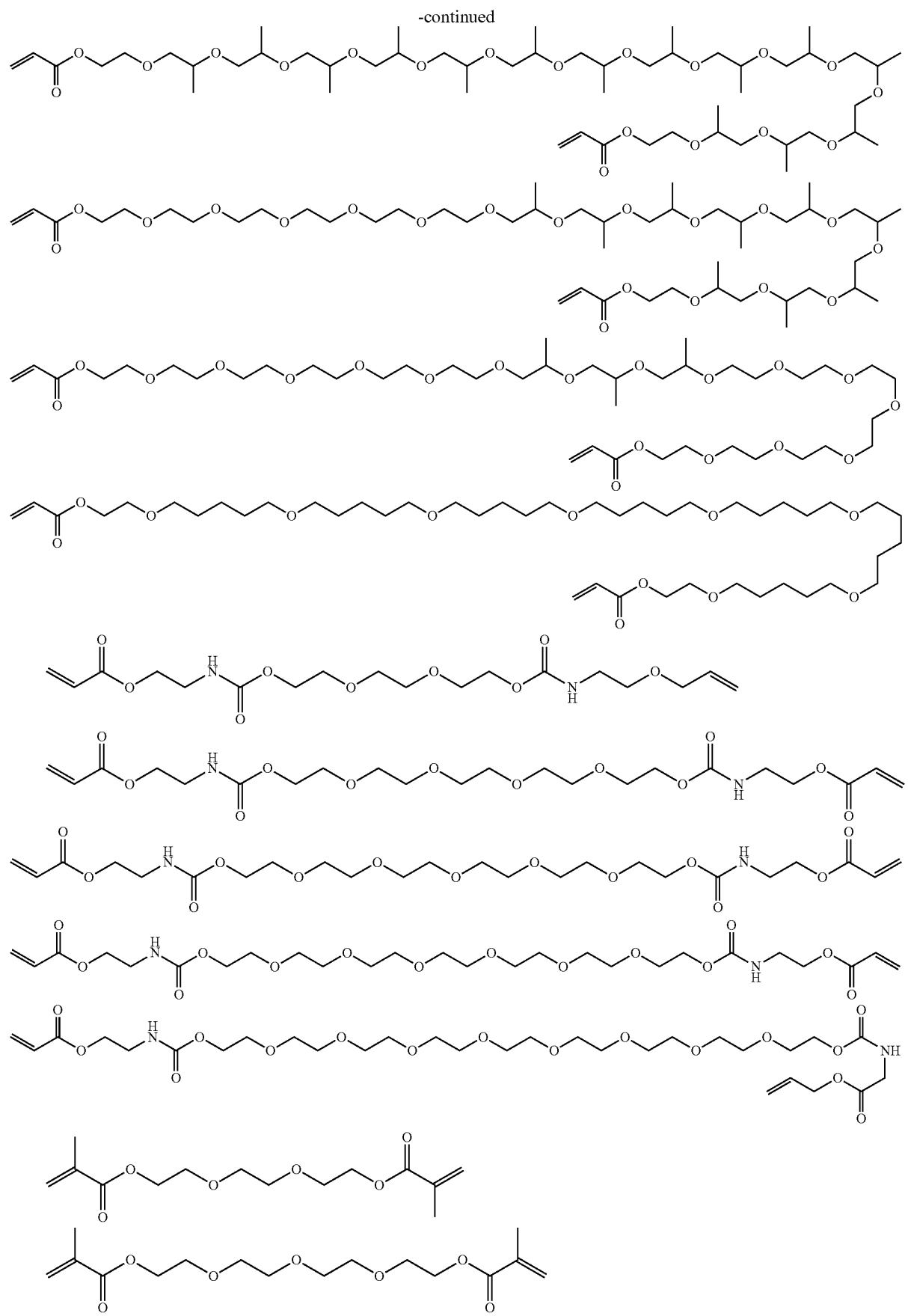

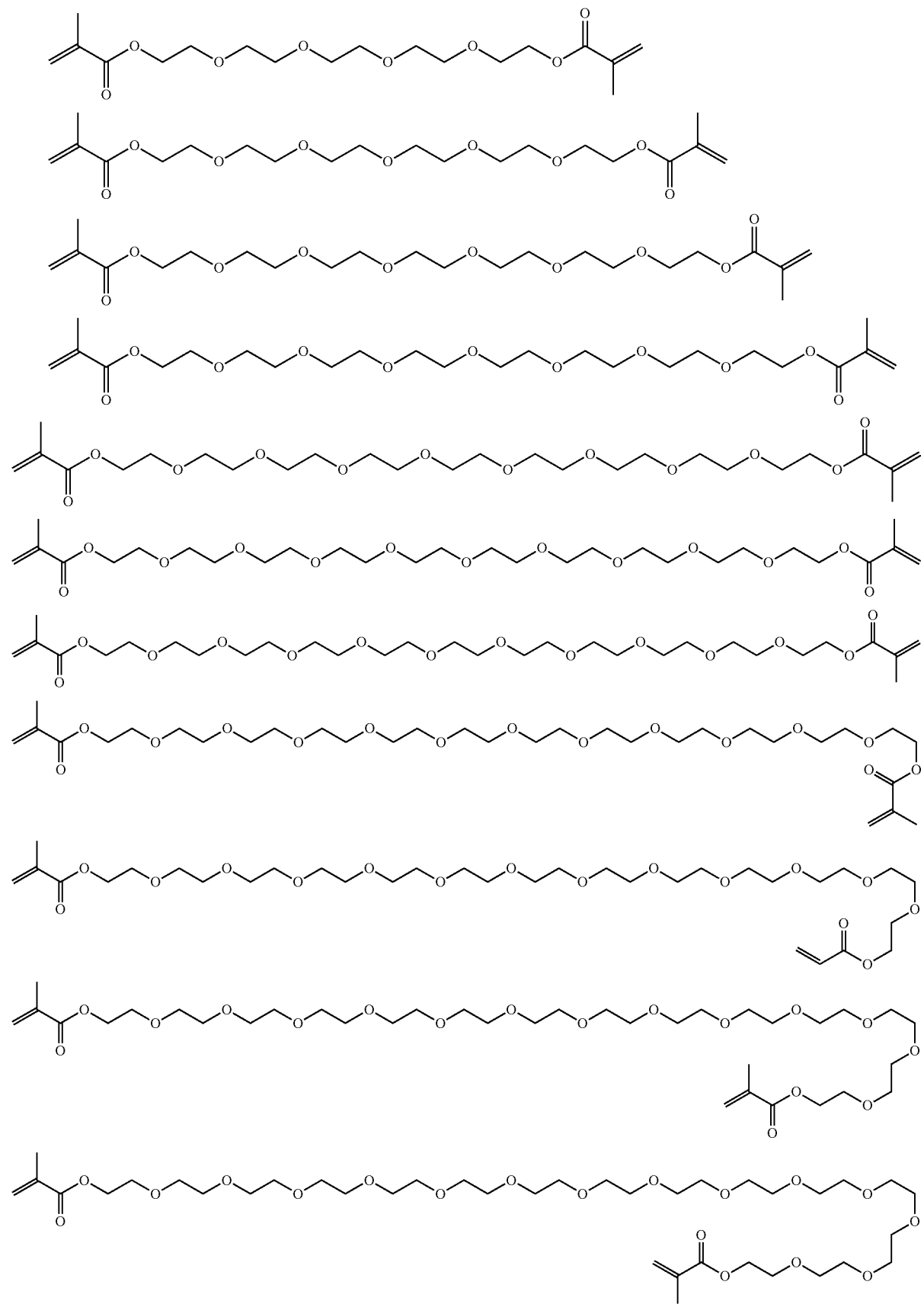

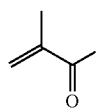 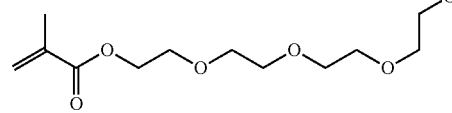

One typical method for synthesizing a polymer of the component (A) may be a method for obtaining a copolymer by adding an initiator of radical polymerization and subjecting a desired monomer out of monomers for providing repeating units "a", "b", "c", "d", and "e" to heat polymerization in an organic solvent.

Illustrative example of the organic solvent used in polymerization includes toluene, benzene, tetrahydrofuran, diethyl ether, and dioxane. Illustrative example of the polymerization initiator includes 2,2'-azobisisobutyronitrile (AIBN), 2,2'-azobis(2,4-dimethylvaleronitrile), dimethyl2,2-azobis (2-methyl propionate), benzoyl peroxide, and lauroyl peroxide. The heating temperature is preferably 50 to 80° C., and the reaction time is preferably 2 to 100 hours, and more preferably 5 to 20 hours.

Herein, each of the repeating units "a", "b", "c", "d", and "e" independently satisfies the equations in ratio; $0<a<1.0$, $0<b<1.0$, $0 \leq c<1.0$, $0 \leq d<1.0$, and $0 \leq e<1.0$, preferably $0.1 \leq a \leq 0.9$, $0.1 \leq b \leq 0.9$, $0 \leq c \leq 0.6$, $0 \leq d \leq 0.6$, and $0 \leq e \leq 0.6$, and more preferably $0.2 \leq a \leq 0.8$, $0.2 \leq b \leq 0.8$, $0 \leq c \leq 0.5$, $0 \leq d \leq 0.5$, and $0 \leq e \leq 0.5$. Also, they satisfy the equation $0<a+b+c+d+e \leq 1$. The ratios of the repeating units "a" and "b" may be equivalent to those of the repeating units "a1" and "b1".

For example, "$a+b+c+d+e=1$" means that in a polymer including repeating units "a", "b", "c", "d", and "e", the total amount of the repeating units "a", "b", "c", "d", and "e" is 100 mole % relative to the total amount of all the repeating units, and "$a+b+c+d+e<1$" means that the total amount of the repeating units "a", "b", "c", "d", and "e" is under 100 mole % relative to all the repeating units, showing the use of other repeating units other than the units "a", "b", "c", "d", and "e".

The molecular weight of the component (A) is preferably 500 or more as weight average molecular weight, more preferably 1,000 or more and 1,000,000 or less, and much more preferably 2,000 or more and 500,000 or less. When the amount of ionic monomer that is not incorporated into a component (A) after polymerization (residual monomer) is small, the resulting skin immersion is small enough to control skin allergy in a biocompatibility test. Preferably, the residual monomer is reduced to 10 parts by mass or less relative to 100 parts by mass of the component (A).

The amount of the component (A) to be blended into the bio-electrode composition of the present invention is preferably 0.1 to 300 parts by mass, and more preferably 1 to 200 parts by mass relative to 100 parts by mass of the component (B). The component (A) may be used singularly or mixed in combination with two or more components.

(B) Resin

The (B) resin blended into the bio-electrode composition of the present invention is a component for preventing salt elution by compatibility with the (A) ionic material (salt) and providing a conductive improver such as carbon to express the adhesion. The resin may be a resin other than the component (A), preferably a thermosetting resin and/or a photocurable resin, particularly one or more resins selected from silicone-based, acrylic-based, and urethane-based resins.

The adhesive silicone-based resin is an addition reaction curable resin or a radical crosslinking reaction curable resin. Illustrative example of the addition reaction curable resin includes diorganosiloxane having an alkenyl group disclosed in Japanese Unexamined Patent publication (Kokai) No. 2015-193803, an MQ resin having $R_3SiO_{0.5}$ and $SiO_2$ units, organohydrogen polysiloxane having a plurality of SiH groups, and a resin containing a platinum catalyst, an addition inhibitor, and an organic solvent. Illustrative example of the radical crosslinking reaction curable resin includes e.g., as disclosed in Japanese Unexamined Patent publication (Kokai) No. 2015-193803, diorganopolysiloxane having an alkenyl group or not, an MQ resin having $R_3SiO_{0.5}$ and $SiO_2$ units, and a resin containing organic peroxide and an organic solvent. Herein, R represents a hydrocarbon group of a substituted or an unsubstituted monovalent having 1 to 10 carbon atoms.

A compound including a combination of polysiloxane and a resin formed by condensation reaction of polysiloxane having silanol at a polymer terminal or on a side chain and an MQ resin can be used. An MQ resin, containing silanol in large quantities, can be added to improve the adhesive strength, and its non-crosslinking structure leads to no intermolecular bonding with polysiloxane. As described above, integration of polysiloxane and a resin can enhance the adhesive strength.

Also, modified siloxane having a group selected from an amino group, an oxirane group, an oxetane group, a polyether group, a hydroxy group, a carboxyl group, a mercapto group, a methacryl group, an acrylic group, a phenol group, a silanol group, a carboxylic acid anhydride group, an aryl group, an aralkyl group, an amide group, an ester group, and a lactone ring can be added to the silicone-based resin. The addition of modified siloxane improves the dispersion in a silicone resin of the component (A). In any modified siloxane, either or both terminals, or a side chain of siloxane may be modified.

The adhesive acrylic-based resin may include hydrophilic ester (meth)acrylate disclosed in Japanese Unexamined Patent publication (Kokai) No. 2016-011338, and long-chain hydrophobic ester (meth)acrylate as a repeating unit. In some cases, ester (meth)acrylate having a functional group or ester (meth)acrylate having a siloxane bond may be copolymerized.

The adhesive urethane-based resin may have e.g., a urethane bond disclosed in Japanese Unexamined Patent publication (Kokai) No. 2016-065238, a polyether bond, a polyester bond, a polycarbonate bond, or a siloxane bond.

To prevent declines in conductivity due to elution of the component (A) from a living body contact layer, in the bio-electrode composition of the present invention, a (B) resin preferably has higher compatibility with the component (A). To prevent peeling of a living body contact layer from a conductive substrate, in the bio-electrode composition of the present invention, a (B) resin preferably has high adhesion to a conductive substrate. To provide the resin with a higher compatibility with a conductive substrate and a salt, the use of highly polar resin is effective. Illustrative example of the resin includes a resin containing one or more selected from an ether bond, an ester bond, an amide bond, an imide bond, a urethane bond, thiourethane bond, and a thiol group, a polyacrylic resin, a polyamide resin, a polyimide resin, a polyurethane resin, and a polythiourethane resin. On the other hand, a living body contact layer is in contact with a living body to be readily affected by sweating from the living body. Accordingly, in the bio-electrode composition of the present invention, the (B) resin preferably has high water repellency and less hydrolysis. To provide the resin with high water repellency and less hydrolysis, use of a resin containing a silicon atom is effective.

The polyacrylic resin containing a silicon atom may desirably be a polymer having silicone on a main chain and a polymer having a silicon atom on a side chain. The polymer having silicone on a main chain may be siloxane having a (meth)acrylicpropyl group or silsesquioxane. In this case, a photo radical generator can be added to polymerize a (meth)acrylic portion to be cured.

The polyamide resins containing a silicon atom may desirably be polyamide silicone resins in e.g., Japanese Unexamined Patent publication (Kokai) No. 2011-079946 and U.S. Pat. No. 5,981,680. These polyamide silicone resins can be synthesized by combining a silicone compound having an amino group at both terminals and a non-silicone compound having an amino group at both terminals, and a non-silicone compound having a carboxyl group at both terminals and a silicone compound having a carboxyl group at both terminals.

Also, polyamic acid before cyclization obtained by reaction of carboxylic acid anhydride and amine may be used. A carboxyl group of polyamic acid may be crosslinked, using an epoxy-based or an oxetane-based crosslinking agent, and a (meth)acrylate portion may be subjected to photo radical crosslinking by esterification reaction of a carboxyl group and hydroxyethyl(meth)acrylate.

The polyimide resin containing a silicon atom may desirably be e.g., a polyimide silicone resin disclosed in Japanese Unexamined Patent publication (Kokai) No. 2002-332305. The polyimide resin is significantly viscous, but a (meth) acrylic-based monomer can be blended as a solvent and a crosslinking agent to reduce the viscosity of the resin.

The polyurethane resin containing a silicon atom may be a polyurethane silicone resin. Such a polyurethane silicone resin can be crosslinked by a urethane bond by blending and heating a compound having an isocyanate group at both terminals and a compound having a hydroxy group at one terminal. In this case, however, a compound having an isocyanate group at both terminals and/or a compound having a hydroxy group at one terminal must contain a silicon atom (siloxane bond). As disclosed in Japanese Unexamined Patent publication (Kokai) No. 2005-320418, a urethane (meth)acrylate monomer can be blended into polysiloxane for photo crosslinking. In addition, a polymer both having a siloxane bond and a urethane bond and having a (meth)acrylate group at one terminal can be photo-crosslinked.

The polythiourethane resin containing a silicon atom can be obtained by reaction of a compound having a thiol group and a compound having an isocyanate group, and either of the compounds may contain a silicon atom. So long as one terminal includes a (meth)acrylate group, the resin can be photo cured.

In addition to diorganosiloxane having the alkenyl group, an MQ resin having $R_3SiO_{0.5}$ and $SiO_2$ units, and organohydrogen polysiloxane having a plurality of SiH groups, modified siloxane having a group selected from an amino group, an oxirane group, an oxetane group, a polyether group, a hydroxy group, a carboxyl group, a mercapto group, a methacryl group, an acrylic group, a phenol group, a silanol group, a carboxylic acid an anhydride group, an aryl group, an aralkyl group, an amide group, an ester group, and a lactone ring is added to the silicone-based resin to enhance the compatibility with the salt.

As later described, a living body contact layer is a cured product of a bio-electrode composition. The curing process can achieve favorable adhesion of a living body contact layer both to the skin and a conductive substrate. The curing step is not particularly restricted, and may be a commonly known one, e.g., by heating and/or light exposure, or by crosslinking reaction using an acid or a base catalyst. The crosslinking reaction may be selected according to Crosslinking Reaction Handbook, Yasuharu Nakayama, MARUZEN-YUSHODO Company, Limited. (2013) Chap. 2, pp. 51 to 371.

Diorganosiloxane having an alkenyl group and organohydrogen polysiloxane having a plurality of SiH groups can be crosslinked by addition reaction using a platinum catalyst.

Illustrative example of the platinum catalyst includes chloroplatinic acid, an alcohol solution of chloroplatinic acid, a reactant of chloroplatinic acid and alcohol, a reactant of chloroplatinic acid and a olefin compound, a reactant of chloroplatinic acid and siloxane containing a vinyl group, a platinum-based catalyst such as a platinum-olefin complex and a siloxane complex containing a platinum-vinyl group, and a platinum group metal-based catalyst such as a rhodium complex and a ruthenium complex. These catalysts may be dissolved or dispersed into an alcohol-based, a hydrocarbon-based, or a siloxane-based solvent.

The amount of the platinum catalyst to be added is preferably 5 to 2,000 ppm, and particularly 10 to 500 ppm relative to 100 parts by mass of a resin.

When an addition curable silicone resin is used, an addition inhibitor may be added. The addition inhibitor is added as a quencher for generating no action of platinum catalyst in a solution and in low-temperature environment before heat curing after forming a coated film. Illustrative example thereof includes 3-methyl-1-butyne-3-ol, 3-methyl-1-pentyne-3-ol, 3,5-dimethyl-1-hexyne-3-ol, 1-ethynyl cyclohexanol, 3-methyl-3-trimethylsiloxy-1-butyne, 3-methyl-3-trimethylsiloxy-1-pentyne, 3,5-dimethyl-3-trimethylsiloxy-1-hexyne, 1-ethynyl-1-trimethylsiloxy cyclohexane, bis(2,2-dimethyl-3-butynoxy)dimethylsilane, 1,3,5,7-tetramethyl-1,3,5,7-tetravinyl cyclotetrasiloxane, and 1,1,3,3-tetramethyl-1,3-divinyldisiloxane.

The amount of the addition inhibitor to be added is preferably 0 to 10 parts by mass, and particularly 0.05 to 3 parts by mass relative to 100 parts by mass of a resin.

Illustrative example of the photo curing method includes a method for using a resin having a (meth)acrylate terminal or an olefin terminal, adding a crosslinking agent whose terminal is (meth)acrylate, olefin, or a thiol group, and adding a photo radical generator, and a method for adding a photo acid generator by using a resin having an oxirane group, an oxetane group, and a vinylether group or a crosslinking agent.

Illustrative example of the photo radical generator includes acetophenone, 4,4'-dimethoxybenzyl, benzyl, benzoin, benzophenone, 2-benzoylbenzoic acid, 4,4'-bis(dimethylamino)benzophenone, 4,4'-bis(diethylamino)benzophenone, benzoinmethyl ether, benzoinethyl ether, benzoinisopropyl ether, benzoinbutyl ether, benzoinisobutyl ether, 4-benzoylbenzoic acid, 2,2'-bis(2-chlorophenyl)-4,4',5,5'-tetraphenyl-1,2'-biimidazole, 2-benzoylbenzoic acid methyl, 2-(1,3-benzodioxole-5-yl)-4,6-bis(trichloromethyl)-1,3,5-triazine, 2-benzyl-2-(dimethylamino)-4'-morpholinobutyrophenone, 4,4'-dichlorobenzophenone, 2,2-diethoxyacetophenone, 2,2-dimethoxy-2-phenylacetophenone, 2,4-diethylthioxanthen-9-one, diphenyl(2,4,6-trimethylbenzoyl)phosphine oxide (BAPO), 1,4-dibenzoylbenzene, 2-ethylanthraquinone, 1-hydroxy cyclohexylphenyl ketone, 2-hydroxy-2-methylpropiophenone, 2-hydroxy-4'-(2-hydroxyethoxy)-2-methylpropiophenone, 2-isonitrosopropiophenone, and 2-phenyl-2-(p-toluenesulfonyloxy)acetophenone.

The addition of a thermal decomposition radical generator can achieve curing. Illustrative example of the heat radical generator includes 2,2'-azobis(isobutyronitrile), 2,2'-azobis(2,4-dimethylvaleronitrile), 2,2'-azobis(2-methylbutyronitrile), 4,4'-azobis(4-cyano laballenic acid), 2,2'-azobis(methylpropionamidine)hydrochloric acid, 2,2'-azobis[2-(2-imidazoline-2-yl)propane]hydrochloric acid, 2,2'-azobis(4-methoxy-2,4-dimethylvaleronitrile), 2,2'-azobis(cyclohexane-1-carbonitrile), 1[(1-cyano-1-methylethyl)azo]formamide, 2,2'-azobis[2-methyl-N-(2-hydroxyethyl)propionamide], 2,2'-azobis[N-(2-propenyl)-2-methylpropionamide], 2,2'-azobis(N-butyl-2-methylpropionamide), dimethyl-2,2'-azobis(isobutyrate), 4,4'-azobis(4-cyano pentanoic acid), dimethyl-2,2'-azobis(2-methyl propionate), benzoyl peroxide, tert-butylhydro peroxide, cumenehydro peroxide, di-tert-butyl peroxide, di-tert-amyl peroxide, di-n-butyl peroxide, dimethyl-2,2'-azobis(2-methylpropronate), and dicumyl peroxide.

Illustrative example of the photo acid generator includes a sulfonium salt, an iodonium salt, sulfonyl diazomethane, N-sulfonyl oximide, and oxime-O-sulfonate acid generator. Illustrative example of the photo acid generator includes those disclosed in Japanese Unexamined Patent publication (Kokai) No. 2008-111103 (paras. [0122] to [0142]) and Japanese Unexamined Patent publication (Kokai) No. 2009-080474.

The amount of the radical generator or the photo acid generator to be added is preferably 0.1 to 50 parts by mass relative to 100 parts by mass of a resin.

Particularly, among these, the resin of the component (B) may preferably be a silicone resin having a $R_xSiO_{(4-x)/2}$ unit, wherein R represents a substituted or an unsubstituted monovalent hydrocarbon group having 1 to 10 carbon atoms; and x represents a number of 2.5 to 3.5, and a $SiO_2$ unit, diorganosiloxane having an alkenyl group, and organohydrogen polysiloxane having a SiH group.

Tackiness Imparting Agent

Also, to provide adhesion to a living body for the bio-electrode composition of the present invention, a tackiness imparting agent may be added. Illustrative example of the tackiness imparting agent includes a silicone resin, non-crosslinking siloxane, non-crosslinking poly(meth)acrylate, and non-crosslinking polyether.

Organic Solvent

Also, an organic solvent can be added to the bio-electrode composition of the present invention. Illustrative example of the organic solvent includes an aromatic hydrocarbon solvent such as toluene, xylene, cumene, 1,2,3-trimethyl benzene, 1,2,4-trimethyl benzene, 1,3,5-trimethyl benzene, styrene, αmethyl styrene, butyl benzene, sec-butyl benzene, isobutyl benzene, cymene, diethyl benzene, 2-ethyl-p-xylene, 2-propyl toluene, 3-propyl toluene, 4-propyl toluene, 1,2,4,5-tetramethyl toluene, 1,2,4,5-tetramethyl toluene, tetrahydro naphthalene, 4-phenyl-1-butene, tert-amyl benzene, amyl benzene, 2-tert-butyl toluene, 3-tert-butyl toluene, 4-tert-butyl toluene, 5-isopropyl-m-xylene, 3-methylethyl benzene, tert-butyl-3-ethyl benzene, 4-tert-butyl-o-xylene, 5-tert-butyl-m-xylene, tert-butyl-p-xylene, 1,2-diisopropyl benzene, 1,3-diisopropyl benzene, 1,4-diisopropyl benzene, dipropyl benzene, 3,9-dodecadiyne, pentamethyl benzene, hexamethyl benzene, hexyl benzene, 1,3,5-triethyl benzene; an aliphatic hydrocarbon-based solvent such as n-heptane, isoheptane, 3-methyl hexane, 2,3-dimethyl pentane, 3-ethyl pentane, 1,6-heptadiene, 5-methyl-1-hexyne, norbornane, norbornene, dichloropentadiene, 1-methyl-1,4-cyclohexadiene, 1-heptine, 2-heptine, cycloheptane, cycloheptene, 1,3-dimethyl cyclopentane, ethyl cyclopentane, methyl cyclohexane, 1-methyl-1-cyclohexene, 3-methyl-1-cyclohexene, methylene cyclohexane, 4-methyl-1-cyclohexene, 2-methyl-1-hexene, 2-methyl-2-hexene, 1-heptene, 2-heptene, 3-heptene, n-octane, 2,2-dimethyl hexane, 2,3-dimethyl hexane, 2,4-dimethyl hexane, 2,5-dimethyl hexane, 3,3-dimethyl hexane, 3,4-dimethyl hexane, 3-ethyl-2-methyl pentane, 3-ethyl-3-methyl pentane, 2-methyl heptane, 3-methyl heptane, 4-methyl heptane, 2,2,3-trimethyl pentane, 2,2,4-trimethyl pentane, cyclooctane, cyclooctene, 1,2-dimethyl cyclohexane, 1,3-dimethyl cyclohexane, 1,4-dimethyl cyclohexane, ethyl cyclohexane, vinyl cyclohexane, isopropyl cyclopentane, 2,2-dimethyl-3-hexene, 2,4-dimethyl-1-hexene, 2,5-dimethyl-1-hexene, 2,5-dimethyl-2-hexene, 3,3-dimethyl-1-hexene, 3,4-dimethyl-1-hexene, 4,4-dimethyl-1-hexene, 2-ethyl-1-hexene, 2-methyl-1-heptene, 1-octene, 2-octene, 3-octene, 4-octene, 1,7-octadiene, 1-octyne, 2-octyne, 3-octyne, 4-octyne, n-nonane, 2,3-dimethyl heptane, 2,4-dimethyl heptane, 2,5-dimethyl heptane, 3,3-dimethyl heptane, 3,4-dimethyl heptane, 3,5-dimethyl heptane, 4-ethyl heptane, 2-methyl octane, 3-methyl octane, 4-methyl octane, 2,2,4,4-tetramethyl pentane, 2,2,4-trimethyl hexane, 2,2,5-trimethyl hexane, 2,2-dimethyl-3-heptene, 2,3-dimethyl-3-heptene, 2,4-dimethyl-1-heptene, 2,6-dimethyl-1-heptene, 2,6-dimethyl-3-heptene, 3,5-dimethyl-3-heptene, 2,4,4-trimethyl-1-hexene, 3,5,5-trimethyl-1-hexene, 1-ethyl-2-methyl cyclohexane, 1-ethyl-3-methyl cyclohexane, 1-ethyl-4-methyl cyclohexane, propyl cyclohexane, isopropyl cyclohexane, 1,1,3-trimethyl cyclohexane, 1,1,4-trimethyl cyclohexane, 1,2,3-trimethyl cyclohexane, 1,2,4-trimethyl cyclohexane, 1,3,5-trimethyl cyclohexane, allyl cyclohexane, hydrindane, 1,8-nonadiene, 1-nonyne, 2-nonyne, 3-nonyne, 4-nonyne, 1-nonene, 2-nonene, 3-nonene, 4-nonene, n-decane, 3,3-dimethyl octane, 3,5-dimethyl octane, 4,4-dimethyl octane, 3-ethyl-3-methyl heptane, 2-methyl nonane, 3-methyl nonane, 4-methyl nonane, tert-butyl cyclohexane, butyl cyclohexane, isobutyl cyclohexane, 4-isopropyl-1-methyl cyclohexane, pentyl cyclopentane, 1,1,3,5-tetramethyl cyclohexane, cyclododecane, 1-decene, 2-decene, 3-decene, 4-decene, 5-decene, 1,9-decadiene, decahydronaphthalene, 1-decyne, 2-decyne, 3-decyne, 4-decyne, 5-decyne, 1,5,9-decatriene, 2,6-dimethyl-2,4,6-octatriene, limonene, myrcene, 1,2,3,4,5-pentamethyl cyclopentadiene, α-phellandrene, pinene, terpinene, tetrahydrodicyclopentadiene, 5,6-dihydrodicyclopentadiene, dichloropentadiene, 1,4-decadiyne, 1,5-decadiyne, 1,9-decadiyne, 2,8-decadiyne, 4,6-decadiyne, n-undecane, amyl cyclohexane, 1-undecene, 1,10-undecadiene, 1-undecyne, 3-undecyne, 5-undecyne, tricyclo[6.2.1.0$^{2,7}$]undeca-4-en, n-dodecane, 2-methyl undecane, 3-methyl undecane, 4-methyl undecane, 5-methyl undecane, 2,2,4,6,6-pentamethyl heptane, 1,3-dimethyladamantane, 1-ethyladamantane, 1,5,9-cyclododecatriene, 1,2,4-trivinyl cyclohexane, isoparaffin; a ketone-based solvent such as cyclohexanone, cyclopentanone, 2-octanone, 2-nonanone, 2-heptanone, 3-heptanone, 4-heptanone, 2-hexanone, 3-hexanone, diisobutyl ketone, methyl cyclohexanone, and methyln-pentyl ketone; an alcohol-based solvent such as 3-methoxy butanol, 3-methyl-3-methoxy butanol, 1-methoxy-2-propanol, and 1-ethoxy-2-propanol; an ether-based solvent such as propylene glycol monomethyl ether, ethylene glycol monomethyl ether, propylene glycol monoethyl ether, ethylene glycol monoethyl ether, propylene glycol dimethyl ether, diethylene glycol dimethyl ether, diisopropyl ether, diisobutyl ether, diisopentyl ether, di-n-pentyl ether, methyl cyclopentyl ether, methyl cyclohexyl ether, di-n-butyl ether, di-secbutyl ether, disec-pentyl ether, di-tert-amyl ether, di-n-hexyl ether, and anisole; an ester-based solvent such as propylene glycol monomethyl ether acetate, propylene glycol monoethyl ether acetate, ethyl lactate, ethyl pyruvate, butyl acetate, methyl 3-methoxy propionate, ethyl 3-ethoxy propionate, tert-butyl acetate, tert-butyl propionate, propylene glycol monotert-butyl ether acetate; and a lactone-based solvent such as γ-butyrolactone.

The amount of the organic solvent to be added is preferably 10 to 50,000 parts by mass relative to 100 parts by mass of a polymer.

Carbon Material

A carbon material can be added to the bio-electrode composition of the present invention as a conductive improver to further enhance the conductivity. Illustrative example of the carbon material includes carbon black and carbon nanotube, and carbon fibers. The carbon nanotube may be either single-layer or multi-layer, and the surface may be modified with an organic group. The amount of the carbon material to be added is preferably in the range of 1 to 50 parts by mass relative to 100 parts by mass of a polymer.

Conductive Improver Other than Carbon Material

A conductive improver other than a carbon material can be added to the bio-electrode composition of the present invention. Illustrative example thereof includes a particle, a fiber and a nanowire for coating a resin with a precious metal such as gold, silver, and platinum, a nanoparticle such as gold, silver, and platinum, and a particle of metal oxide such as indium tin oxide (ITO), indium zinc oxide (IZO), tin oxide, and zinc oxide.

As described above, the bio-electrode composition of the present invention can form a living body contact layer that is capable of efficiently converting changes in ion concentration from the skin into electric signals and efficiently transmitting such electric signals to a device (or that is excellent in conductivity), generating no allergy despite its long-time attachment to the skin (or that is excellent in biocompatibility), is light-weight, can be manufactured at low cost, and can control significant reduction in conductivity even though the bio-electrode is soaked in water or dried. Also, the addition of a carbon material can further improve the conductivity, and a combined use of adhesive and elastic polymers can manufacture particularly adhesive and elastic bio-electrodes. Furthermore, the use of additives can improve the elasticity and adhesion to the skin. The resin constituent and the thickness of a living body contact layer can be adjusted as required to control the elasticity and adhesion.

Bio-Electrode

The present invention provides a bio-electrode including a conductive substrate and a living body contact layer formed on the conductive substrate, wherein the living body contact layer is a cured product of the bio-electrode composition of the present invention.

The bio-electrode of the present invention will be described in detail with reference to the drawings, but the present invention is not restricted thereto.

FIG. 1 is a schematic cross-sectional view showing one example of a bio-electrode of the present invention. In FIG. 1, a bio-electrode 1 includes a conductive substrate 2 and a living body contact layer 3 formed on the conductive substrate 2. The living body contact layer 3 is a layer in which an ionic polymer (ionic material) 4 and a carbon material 5 are dispersed in a resin 6.

Figure 2:
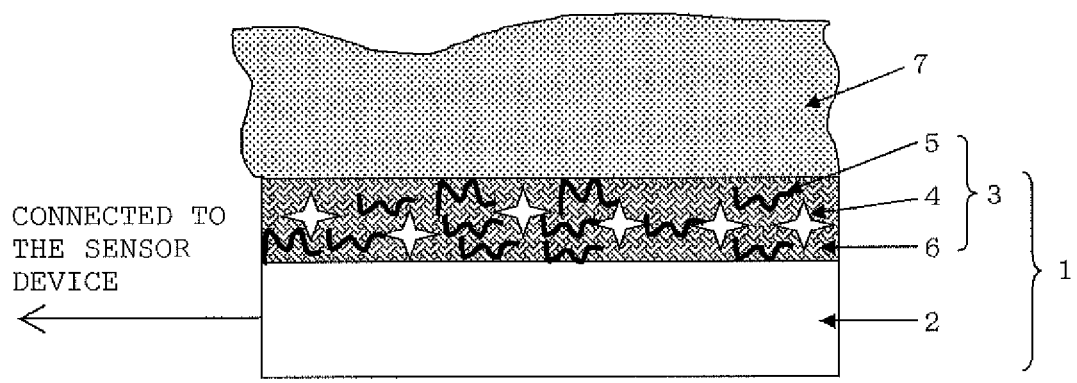
FIG. 2 is a schematic cross-sectional view showing one example of a bio-electrode of the present invention that is attached to a living body.

When such a bio-electrode 1 illustrated in FIG. 1 is used, as illustrated in FIG. 2, a living body contact layer 3 (or, a layer in which an ionic polymer 4 and a carbon material 5 are dispersed in a resin 6) is brought in contact with a living body 7 to take electric signals out of the living body 7 by the ionic polymer 4 and the carbon material 5, and the electric signals are transmitted via the conductive substrate 2 to a sensor device (not shown). Accordingly, the bio-electrode of the present invention can satisfy both conductivity and biocompatibility by the ionic polymer (ionic material). As required, a conductive improver such as carbon material can be added to further improve the conductivity, and its adhesion can keep constant the contact area with the skin and stably obtain electric signals from the skin with high sensitivity.

Each component of the bio-electrode of the present invention will be described in more detail.

Conductive Substrate

The bio-electrode of the present invention includes a conductive substrate. The conductive substrate is normally electrically connected to a sensor device unit to transmit electric signals taken out of a living body via a living body contact layer to the sensor device unit.

The conductive substrate is not particularly restricted so long as it is conductive, but preferably includes one or more substances selected from gold, silver, silver chloride, platinum, aluminum, magnesium, tin, tungsten, iron, copper, nickel, stainless, chromium, titanium, and carbon.

The conductive substrate is not particularly restricted, but may be a hard conductive substrate, a flexible conductive film, a fabric coated with a conductive paste on the surface, or a fabric weaved with a conductive polymer. The conductive substrate may be selected according to use of a bio-electrode e.g., flat, irregular or mesh weaved with metal wire.

Living Body Contact Layer

The bio-electrode of the present invention includes a living body contact layer formed on the conductive substrate. The living body contact layer is in contact with a living body when the bio-electrode is used, having conductivity and adhesion. The living body contact layer is a cured product of the bio-electrode composition of the present invention, or an adhesive resin layer including the (A) ionic material (salt) and the (B) resin, and as required, an additive such as carbon material.

The adhesive strength of a living body contact layer is preferably 0.5N/25 mm or more and 20N/25 mm or less. The method for measuring an adhesive strength is commonly stipulated according to JUS Z 0237 standards. The substrate may be a metal substrate such as SUS (stainless steel) or a PET (polyethylene terephthalate) substrate, but human skin can be used for measurement. The human skin has lower surface energy than metals and plastics, and it is as low as Teflon (registered trademark), and the skin is less likely to adhere.

The thickness of the living body contact layer of the bio-electrode is preferably 1 μm or more and 5 mm or less, and more preferably 2 μm or more and 3 mm or less. A thinner living body contact layer demonstrates lower adhesive strength, but improved flexibility, and light-weight and then favorable compatibility with the skin. The thickness of a living body contact layer can be selected in view of adhesion and touch feeling to the skin.

In the bio-electrode of the present invention, as in a conventional bio-electrode (e.g., a bio-electrode disclosed in Japanese Unexamined Patent publication (Kokai) No. 2004-033468), an additional adhesive film may be provided on a living body contact layer to prevent the bio-electrode from peeling from the living body when in use. In this case, an adhesive film may be formed of an acrylic, a urethane, or a silicone adhesive film material. In particular, a silicone adhesive film material has high oxygen permeability, allowing for dermal respiration with the same attached to the skin. Its higher water repellency can also control reduction in adhesion by sweating, and the stimulation to the skin is advantageously low. In the bio-electrode of the present invention, as described above, the addition of a tackiness imparting agent to a bio-electrode composition or use of a resin favorably adhesive to a living body can prevent peeling from the living body, thereby saving the above additional adhesive film.

When the bio-electrode of the present invention is used as a wearable device, wires for connecting a bio-electrode and a sensor device and other members are not particularly restricted, but those disclosed in e.g., Japanese Unexamined Patent publication (Kokai) No. 2004-033468 can be employed.

As described above, the bio-electrode of the present invention can form a living body contact layer formed of a cured product of the bio-electrode composition of the present invention that is capable of efficiently transmitting electric signals from the skin to a device (or, that is excellent in conductivity), generating no allergy despite its long-time attachment to the skin (or, that is excellent in biocompatibility), is light-weight, can be manufactured at low cost, and can control significant reduction in conductivity even though the bio-electrode is soaked in water or dried. The addition of a carbon material can further improve the conductivity, and a combination of adhesive and elastic polymers can manufacture a particularly highly adhesive, elastic bio-electrode. Furthermore, the use of additives can improve the elasticity and adhesion to the skin. The resin constituent and the thickness of a living body contact layer can be adjusted as required to control the elasticity and adhesion. Accordingly, such a bio-electrode of the present invention is particularly desirable as a bio-electrode used in medical wearable devices.

A Method for Manufacturing a Bio-Electrode

The present invention provides a method for manufacturing a bio-electrode including a conductive substrate and a living body contact layer formed on the conductive substrate, including: applying the bio-electrode composition of the present invention to the conductive substrate to be cured to form the living body contact layer.

A conductive substrate, a bio-electrode composition and others used in the method for manufacturing a bio-electrode of the present invention may represent the same meanings as before.

The method for applying a bio-electrode composition to a conductive substrate is not particularly restricted, but such methods as dipping coat, spraying coat, spin coat, roll coat, flow coat, doctor coat, screen printing, flexographic printing, gravure printing, and ink-jet printing are desirable.

The method for curing a resin is not particularly restricted and may be selected according to the type of (B) resin used in the bio-electrode composition, preferably e.g., by heating and/or light exposure. Also, a catalyst for generating an acid or a base can be added to the bio-electrode composition, thereby generating a crosslinking reaction to cure a resin.

The heating temperature is not particularly restricted and may be selected according to the type of (B) resin used in the bio-electrode composition, preferably e.g., 50 to 250° C.

The resin may be cured by heating and light exposure at the same time, or first light exposure and then heating, or vice versa. The resin may be air-dried to evaporate a solvent prior to heating after film application.

As described above, the method for manufacturing a bio-electrode of the present invention can readily manufacture the bio-electrode of the present invention that is excellent in conductivity and biocompatibility, is light-weight, can be manufactured at low cost, and can control significant reduction in conductivity even though the bio-electrode is soaked in water or dried.

EXAMPLE

The present invention will be described in detail with reference to the Examples and Comparative Examples, but the present invention is not restricted thereto. "Me" refers to a methyl group, while "Vi" refers to a vinyl group.

Ionic polymers 1 to 13 blended into a bio-electrode composition solution as an ionic material (conductive material) were synthesized as follows. A PGMEA solution including 30% by mass of each monomer was mixed in a reaction vessel, and the reaction vessel was cooled down to −70° C. in nitrogen atmosphere, subjected to reduced pressure for deaeration and nitrogen blow three times. After the product was heated at elevated temperatures up to room temperature, AIBN (azobisisobutyronitrile) was added by 0.01 mole relative to 1 mole of the total monomer as a polymerization initiator, heated at elevated temperatures up to 60° C., and was reacted for 15 hours to obtain polymers. The constituent of the polymers obtained was confirmed by $^1$H-NMR after drying the solvent, and the molecular weight (Mw) and the degree of dispersion (Mw/Mn) of the polymers obtained were confirmed by gel permeation chromatography (GPC), using THF (tetrahydrofuran) as a solvent. The ionic polymers 1 to 13 thus synthesized are shown as follows:

Ionic polymer 1
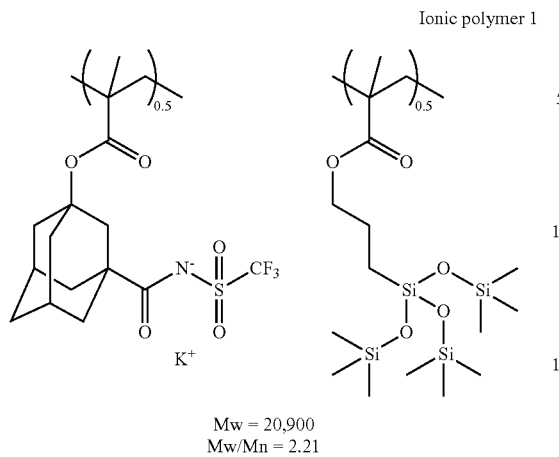
Mw = 20,900
Mw/Mn = 2.21
Ionic polymer 2
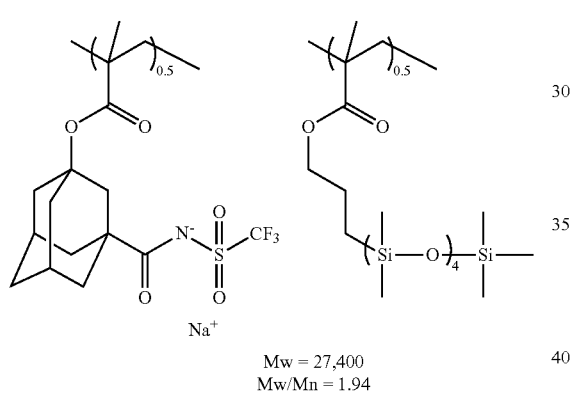
Mw = 27,400
Mw/Mn = 1.94
wherein, the repeating unit represents the average.
Ionic polymer 3
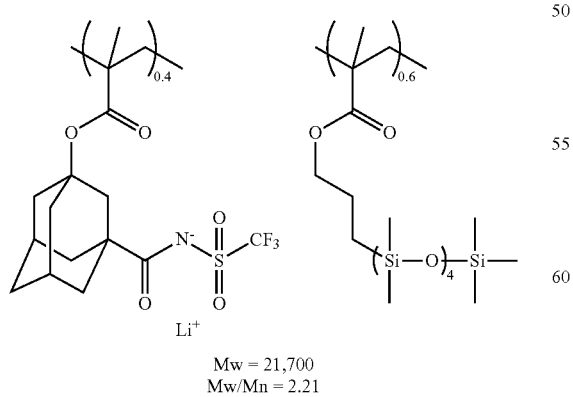
Mw = 21,700
Mw/Mn = 2.21
wherein, the repeating unit represents the average.
Ionic polymer 4
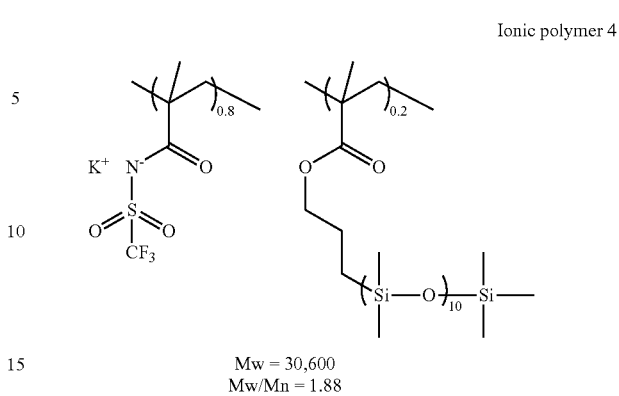
Mw = 30,600
Mw/Mn = 1.88
wherein, the repeating unit represents the average.
Ionic polymer 5
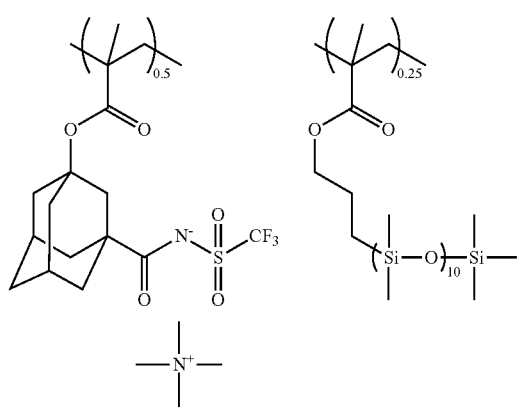
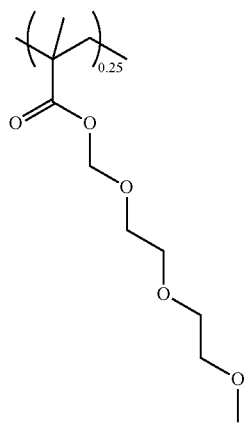
Mw = 26,600
Mw/Mn = 1.86
wherein, the repeating unit represents the average.

Ionic polymer 6
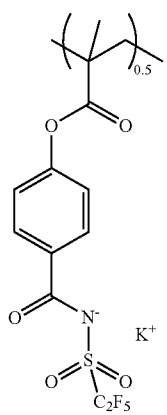 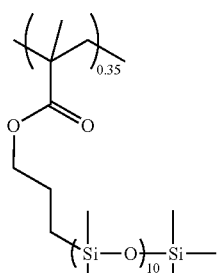 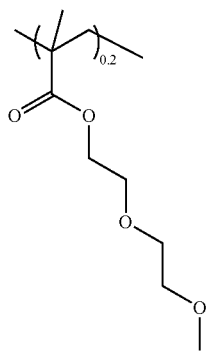
Mw = 35,700
Mw/Mn = 2.33
wherein, the repeating unit represents the average.
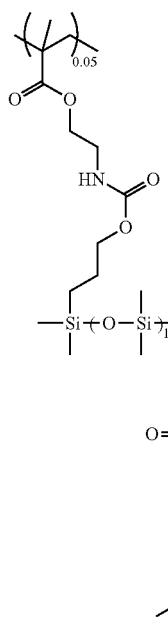 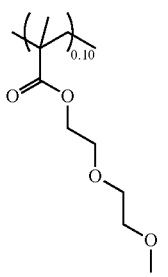
Mw = 88,300
Mw/Mn = 5.3
wherein, the repeating unit represents the average.
Ionic polymer 7
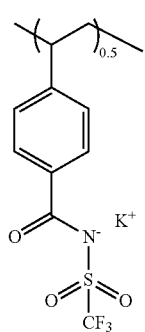 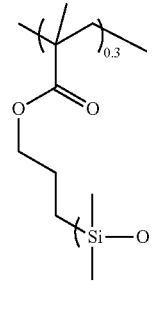
Ionic polymer 8
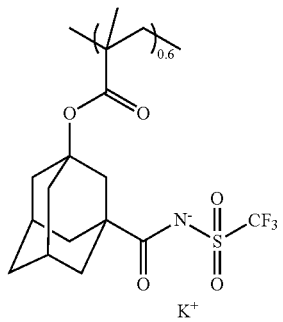
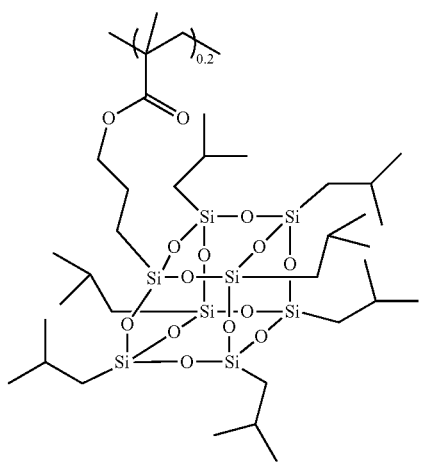

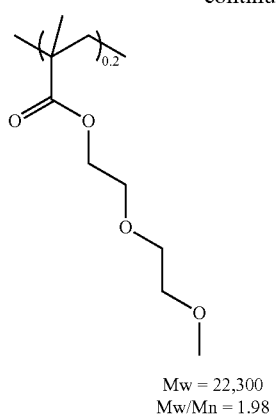
Mw = 22,300
Mw/Mn = 1.98
Ionic polymer 9
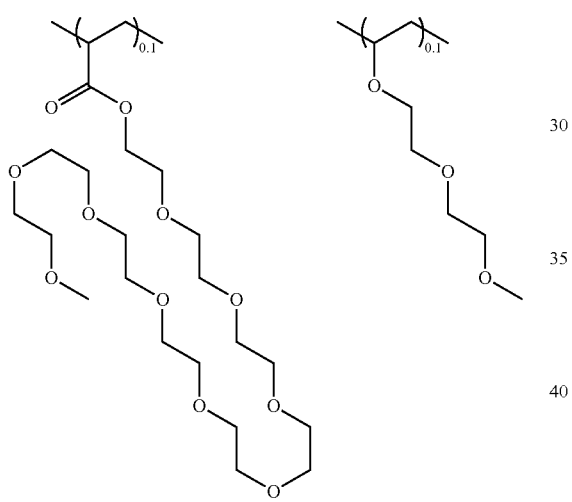
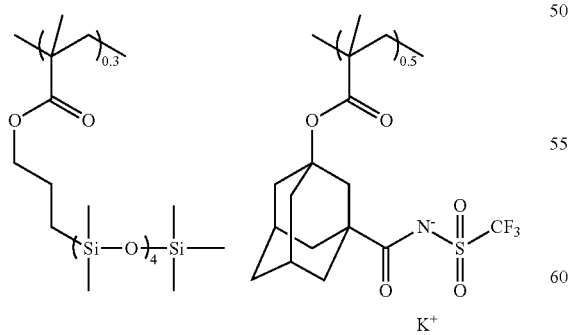
Mw = 32,100
Mw/Mn = 2.03
wherein, the repeating unit represents the average.
Ionic polymer 10
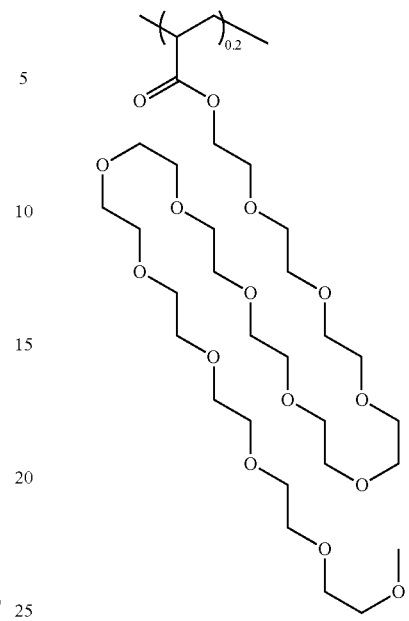
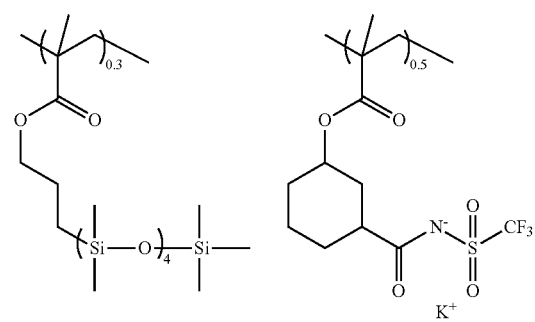
Mw = 48,300
Mw/Mn = 1.93
wherein, the repeating unit represents the average.
Ionic polymer 11
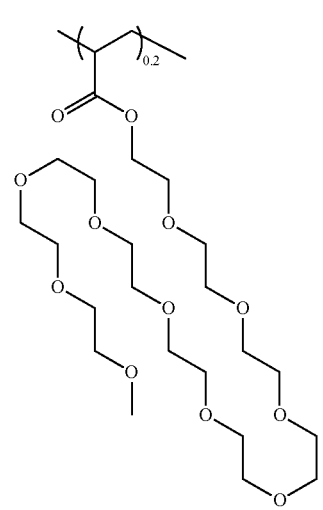

-continued

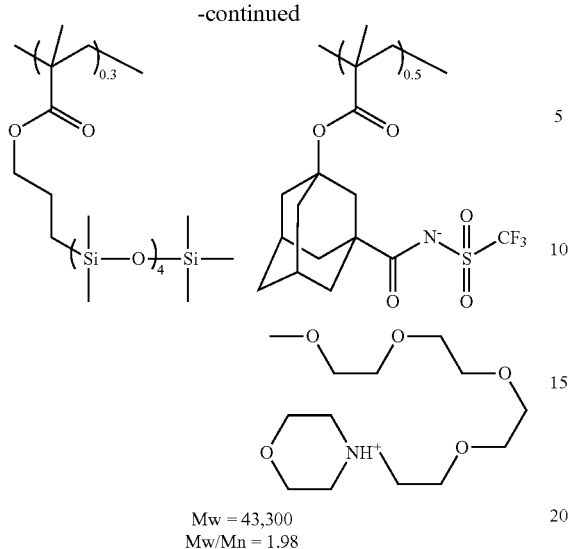

Mw = 43,300
Mw/Mn = 1.98 wherein, the repeating unit represents the average.

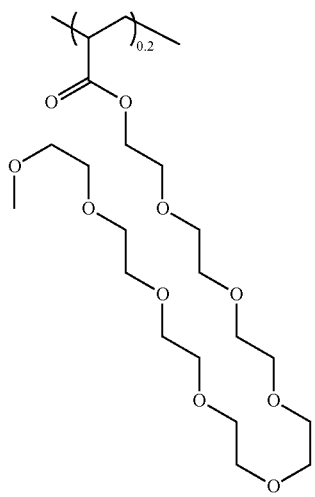

Ionic polymer 12

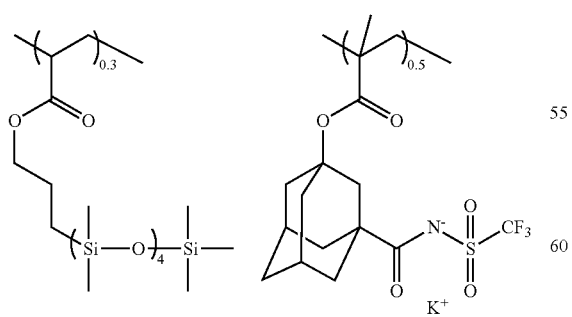

Mw = 51,800
Mw/Mn = 1.79 wherein, the repeating unit represents the average.

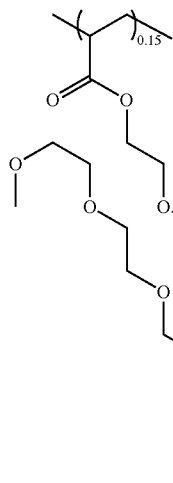

Ionic polymer 13

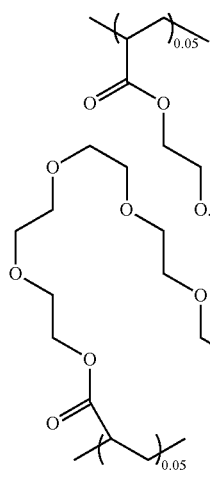

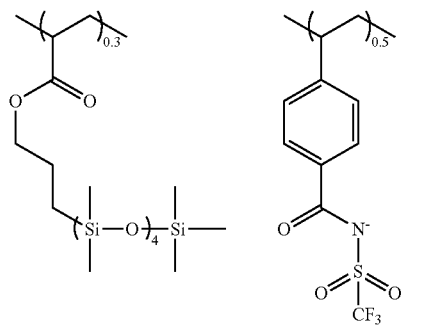

Mw = 85,800
Mw/Mn = 2.88 wherein, the repeating unit represents the average.

The structures of comparative salts 1 to 3 blended into bio-electrode composition solutions of Comparative Examples as ionic materials are shown as follows,

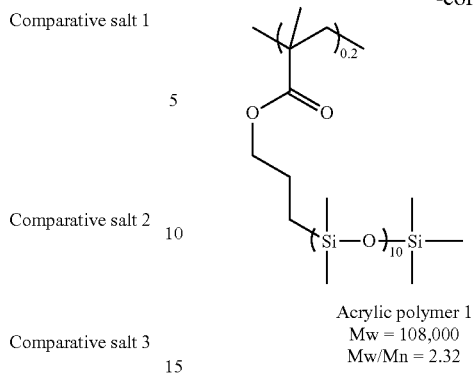

Comparative salt 1

Comparative salt 2

Comparative salt 3

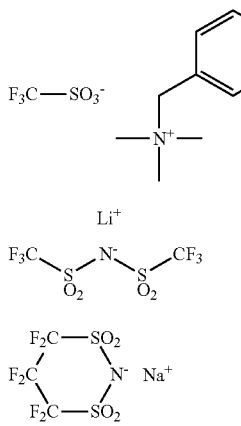

Siloxane compounds 1 to 4 blended into the bio-electrode composition solution as a silicone-based resin are shown as follows.

Siloxane Compound 1

Polydimethylsiloxane containing a vinyl group whose viscosity in a 30% toluene solution is 27,000 mPa·s, whose alkenyl group content is 0.007 mole/100 g, and whose molecular chain terminal is encapsulated by a $SiMe_2Vi$ group, was defined as a siloxane compound 1.

Siloxane Compound 2

Polysiloxane of an MQ resin composed of a $Me_3SiO_{0.5}$ unit and a $SiO_2$ unit ($Me_3SiO_{0.5}$ unit/$SiO_2$ unit=0.8) in a 60% toluene solution was defined as a siloxane compound 2.

Siloxane Compound 3

40 parts by mass of vinyl group-containing polydimethylsiloxane whose viscosity is 42,000 mPa·s in a 30% toluene solution, whose alkenyl group content is 0.007 mole/100 g, and whose molecular chain terminal is encapsulated by an OH group, 100 parts by mass of polysiloxane of an MQ resin composed of a $Me_3SiO_{0.5}$ unit and a $SiO_2$ unit ($Me_3SiO_{0.5}$ unit/$SiO_2$ unit=0.8) in a 60% toluene solution, and a solution composed of 26.7 parts by mass of toluene were subjected to dry distillation, heated for 4 hours and cooled, and the product was bonded to polydimethylsiloxane at the MQ resin to be defined as a siloxane compound 3.

Siloxane Compound 4

KF-99 (Product from Shin-Etsu Chemical Co., Ltd.) was used as methylhydrodiene silicone oil.

Also, a side chain polyether-modified KF-353 (Product from Shin-Etsu Chemical Co., Ltd.) was used as polyether silicone oil composed of a silicone-based resin.

An acrylic polymer 1 blended into a bio-electrode composition solution as an acrylic-based resin is shown as follows:

Acrylic polymer 1

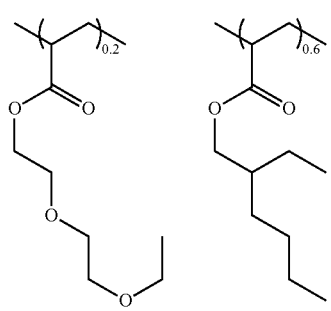

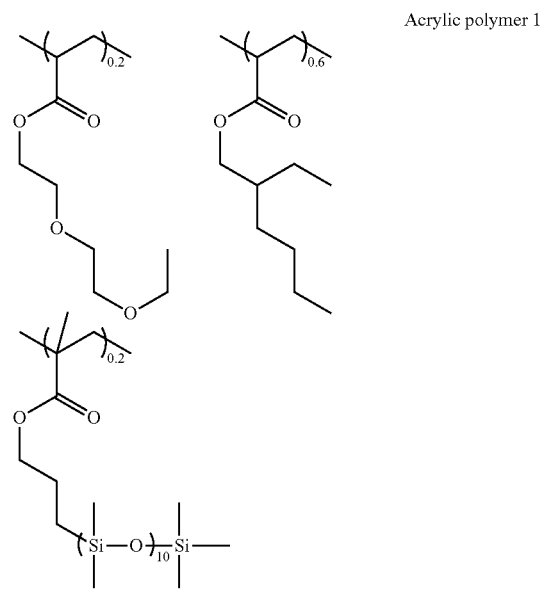

Acrylic polymer 1
Mw = 108,000
Mw/Mn = 2.32 wherein, the repeating unit represents the average.

Silicone urethane acrylates 1 and 2 blended into a bio-electrode composition solution as a silicone-based, an acrylic-based, or a urethane-based resin are shown as follows, Acrylic polymer 1 wherein, the repeating unit represents the average.

Organic solvents blended into bio-electrode composition solutions are shown as follows.

PGMEA: propylene glycol-1-monomethyl ether-2-acetate

PGME: propylene glycol-1-monomethyl ether

A radical generator, a platinum catalyst, and a conductive improver (carbon black, carbon nanotube, gold-coated particle, silver-coated particle, ITO particle) blended into bio-electrode composition solutions as an additive are shown as follows.

Radical generator: V-601, Product from Wako Pure Chemical Industries, Ltd.

Platinum catalyst: CAT-PL-50T, Product from Shin-Etsu Chemical Co., Ltd.

Carbon black: Denka Black HS-100, Product from Denka Company Limited.

Multi-layer carbon nanotube: Product from Sigma-Aldrich Co. LLC. 110 to 170 nm in diameter, 5 to 9 μm in length Gold-coated particle: Micropearl AU (100 μm in diameter), Product from SEKISUI CHEMICAL CO., LTD.

Silver-coated particle: silver-coated powder (30 μm in diameter), Product from MITSUBISHI MATERIALS Corporation ITO particle: ITO powder (0.03 μm in diameter), Product from MITSUBISHI MATERIALS Corporation Examples 1 to 17, Comparative Examples 1 to 5

Ionic materials (salts), resins, organic solvents, and additives (radical generator, platinum catalyst, and conductive improver) were blended with the constituents described in Tables 1 and 2 to prepare bio-electrode composition solutions (bio-electrode composition solutions 1 to 17 and Comparative bio-electrode composition solutions 1 to 5).

TABLE 1

| Bio-electrode composition solution | Ionic material (parts by mass) | Resin (parts by mass) | Organic solvent (parts by mass) | Additive (parts by mass) |
|---|---|---|---|---|
| Bio-electrode composition solution 1 | Ionic polymer 1 (20) | Siloxane compound 1 (40) Siloxane compound 2 (100) Siloxane compound 4 (3) | Toluene (30) | Platinum catalyst (1.5) Carbon black (10) |
| Bio-electrode composition solution 2 | Ionic polymer 2 (20) | Siloxane compound 3 (126) Siloxane compound 4 (3) | Heptane (30) PGMEA (14) | Platinum catalyst (0.7) Carbon black (10) |
| Bio-electrode composition solution 3 | Ionic polymer 3 (22.5) | Siloxane compound 1 (40) Siloxane compound 2 (100) Siloxane compound 4 (3) | Toluene (30) PGMEA (14) | Platinum catalyst (0.7) Carbon black (10) |
| Bio-electrode composition solution 4 | Ionic polymer 4 (20) | Siloxane compound 1 (40) Siloxane compound 2 (100) Siloxane compound 4 (3) | Toluene (30) PGMEA (14) | Platinum catalyst (0.7) Carbon black (10) |
| Bio-electrode composition solution 5 | Ionic polymer 5 (20) | Siloxane compound 3 (126) Siloxane compound 4 (3) KF-353 (2.5) | Toluene (44) | Platinum catalyst (1.0) Carbon black (10) |
| Bio-electrode composition solution 6 | Ionic polymer 6 (20) | Siloxane compound 3 (126) Siloxane compound 4 (3) KF-353 (26) | Toluene (30) 2-heptanone (14) | Platinum catalyst (2.0) Carbon black (10) |
| Bio-electrode composition solution 7 | Ionic polymer 7 (25) | Siloxane compound 3 (126) Siloxane compound 4 (3) | Toluene (30) PGME (14) | Platinum catalyst (1.0) Carbon black (10) |
| Bio-electrode composition solution 8 | Ionic polymer 8 (24) | Siloxane compound 3 (126) Siloxane compound 4 (3) | Toluene (30) PGME (14) | Platinum catalyst (1.5) Carbon black (10) |
| Bio-electrode composition solution 9 | Ionic polymer 8 (24) | Siloxane compound 3 (126) Siloxane compound 4 (3) | Toluene (30) PGME (14) | Platinum catalyst (1.5) Multi-layered carbon nanotube (6) |
| Bio-electrode composition solution 10 | Ionic polymer 1 (20) | Acrylic polymer 1 (60) Silicone urethane acrylate 1 (20) | PGMEA (100) | Radical generator (4) Silver-coated particle (40) |
| Bio-electrode composition solution 11 | Ionic polymer 1 (20) | Acrylic polymer 1 (55) Silicone urethane acrylate 1 (25) | PGMEA (100) | Radical generator (4) Gold-coated particle (40) |
| Bio-electrode composition solution 12 | Ionic polymer 1 (20) | Acrylic polymer 1 (60) Silicone urethane acrylate 2 (20) | PGMEA (100) | Radical generator (4) ITO particle (40) |
| Bio-electrode composition solution 13 | Ionic polymer 9 (20) | Siloxane compound 1 (40) Siloxane compound 2 (100) Siloxane compound 4 (3) | Toluene (30) | Platinum catalyst (1.5) Carbon black (10) |
| Bio-electrode composition solution 14 | Ionic polymer 10 (20) | Siloxane compound 3 (126) Siloxane compound 4 (3) | Heptane (30) PGMEA (14) | Platinum catalyst (1.7) Carbon black (10) |
| Bio-electrode composition solution 15 | Ionic polymer 11 (22.5) | Siloxane compound 1 (40) Siloxane compound 2 (100) Siloxane compound 4 (3) | Toluene (30) PGMEA (14) | Platinum catalyst (1.7) Carbon black (10) |
| Bio-electrode composition solution 16 | Ionic polymer 12 (20) | Siloxane compound 1 (40) Siloxane compound 2 (100) Siloxane compound 4 (3) | Toluene (30) PGMEA (14) | Platinum catalyst (1.7) Carbon black (10) |
| Bio-electrode composition solution 17 | Ionic polymer 13 (20) | Siloxane compound 1 (40) Siloxane compound 2 (100) Siloxane compound 4 (3) | Toluene (30) PGMEA (14) | Platinum catalyst (1.7) Carbon black (10) |

TABLE 2

| Bio-electrode composition solution | Ionic material (parts by mass) | Resin (parts by mass) | Organic solvent (parts by mass) | Additive (parts by mass) |
|---|---|---|---|---|
| Comparative bio-electrode composition solution 1 | Comparative salt 1 (4.7) | Siloxane compound 3 (126)<br>Siloxane compound 4 (3) | Toluene (30)<br>PGME (14) | Platinum catalyst (1.0)<br>Carbon black (10) |
| Comparative bio-electrode composition solution 2 | Comparative salt 2 (8.2) | Siloxane compound 3 (126)<br>Siloxane compound 4 (3) | Toluene (30)<br>PGME (14) | Platinum catalyst (1.0)<br>Carbon black (10) |
| Comparative bio-electrode composition solution 3 | Comparative salt 3 (8.4) | Siloxane compound 3 (126)<br>Siloxane compound 4 (3) | Toluene (30)<br>PGME (14) | Platinum catalyst (1.0)<br>Carbon black (10) |
| Comparative bio-electrode composition solution 4 | — | Siloxane compound 3 (126)<br>Siloxane compound 4 (3) | Toluene (30)<br>PGME (14) | Platinum catalyst (1.0)<br>Carbon black (10) |
| Comparative bio-electrode composition solution 5 | Ionic polymer 1 (100) | — | PGMEA (100) | Carbon black (10) |

Evaluation of Conductivity

Figure 3:
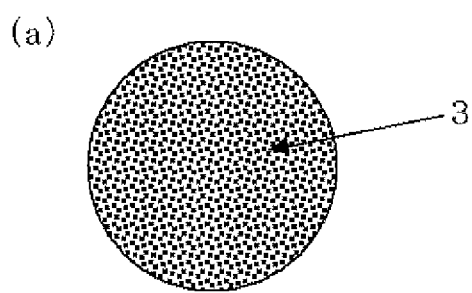
FIG. 3(a) is a schematic illustration of a bio-electrode manufactured with an Example of the present invention viewed from the living body contact layer side.
FIG. 3(b) is a schematic illustration of the bio-electrode manufactured with an Example of the present invention viewed from the conductive substrate side.
Figure 3:
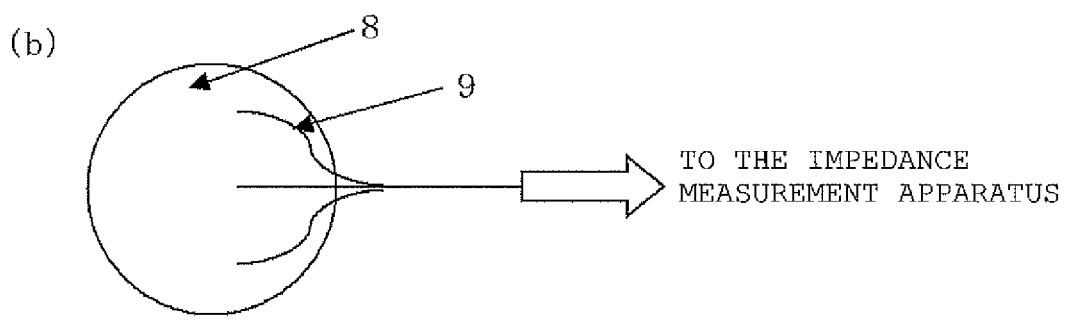
Figure 4:
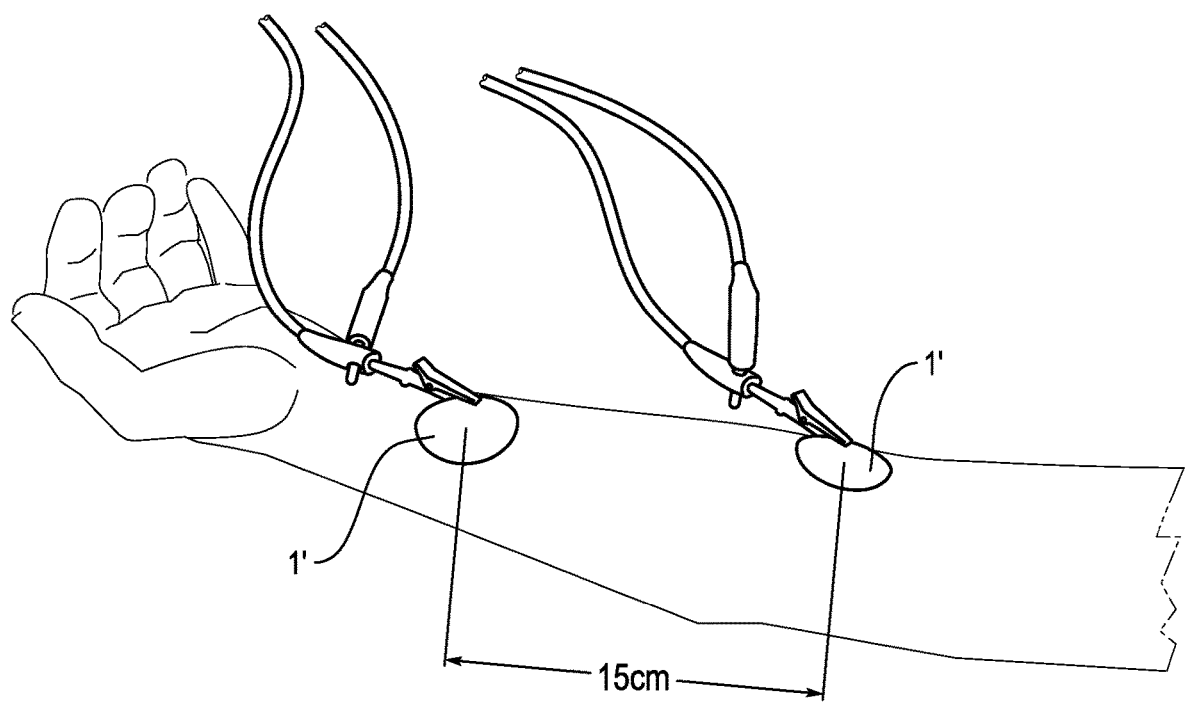
FIG. 4 is a photo showing that the impedance is measured on the skin surface, using a bio-electrode manufactured with an Example of the present invention.

A bio-electrode composition solution was applied to an aluminum disk 3 cm in diameter and 0.2 mm in thickness using an applicator, air-dried at room temperature for 6 hours, and then baked in nitrogen atmosphere at 120° C. for 30 minutes using an oven to be cured to prepare 4 bio-electrodes per one bio-electrode composition solution. Each of the bio-electrodes thus obtained, as illustrated in FIGS. 3(a) and 3(b), includes a living body contact layer 3 on one surface, and an aluminum disk 8 as a conductive substrate on the other surface. Then, as illustrated in FIG. 3(b), a copper wire 9 is attached to the surface of the aluminum disk 8 on a side that is not covered with the living body contact layer with adhesive tape, which was defined as an extraction electrode, and this electrode was connected to an impedance voltage transducer. As illustrated in FIG. 4, 2 bio-electrodes 1' were applied to the arm's skin so that the skin was connected to the living body contact layer side, with an interval of 15 cm. The initial impedance was measured with an alternating current impedance voltage transducer SI 1260 from Solartron Corporation with various frequencies. Then, after the two residual bio-electrodes were immersed in pure water for one hour and the water was dried, the impedance on the skin was measured by the above method. Table 3 shows the impedance with a frequency of 1,000 Hz.

Evaluation of Adhesion

Each of the bio-electrode composition solutions was applied to a PEN (polyethylene naphthalate) substrate 100 μm in thickness using an applicator, and air-dried at room temperature for 6 hours, then using an oven, baked in nitrogen atmosphere at 120° C. for 30 minutes to be cured to prepare an adhesive film. A 25 mm-width tape was cut from the adhesive film, and this was attached to a stainless plate (SUS304) by pressure, and left unattended at room temperature for 20 hours. The force for requiring a tape prepared from the adhesive film to peel from the stainless plate at a speed of 300 mm/min with an angle of 180 degrees (N/25 mm) was measured with a tensile tester. Table 3 shows the results.

Measurement of Thickness of Living Body Contact Layer

In the bio-electrodes prepared in the conductivity evaluation test, the thickness of living body contact layers was measured with a micrometer. Table 3 shows the results.

TABLE 3

| | Bio-electrode composition solution | adhesion (N/25 mm) | Thickness of resin (μm) | Initial impedance (Ω) | Impedance after water immersion (Ω) |
|---|---|---|---|---|---|
| Example 1 | Bio-electrode composition solution 1 | 3.2 | 610 | $2.8E^4$ | $2.3E^4$ |
| Example 2 | Bio-electrode composition solution 2 | 3.2 | 460 | $1.8E^4$ | $1.1E^4$ |
| Example 3 | Bio-electrode composition solution 3 | 3.5 | 510 | $7.2E^3$ | $9.3E^3$ |
| Example 4 | Bio-electrode composition solution 4 | 2.1 | 480 | $4.8E^4$ | $5.1E^4$ |
| Example 5 | Bio-electrode composition solution 5 | 2.4 | 490 | $8.2E^4$ | $8.9E^4$ |
| Example 6 | Bio-electrode composition solution 6 | 4.2 | 560 | $4.0E^3$ | $4.3E^3$ |
| Example 7 | Bio-electrode composition solution 7 | 2.2 | 580 | $6.9E^3$ | $6.0E^3$ |
| Example 8 | Bio-electrode composition solution 8 | 1.9 | 430 | $7.0E^4$ | $7.8E^4$ |
| Example 9 | Bio-electrode composition solution 9 | 2.1 | 520 | $3.2E^4$ | $3.9E^4$ |

TABLE 3-continued

| | Bio-electrode composition solution | adhesion (N/25 mm) | Thickness of resin (μm) | Initial impedance (Ω) | Impedance after water immersion (Ω) |
|---|---|---|---|---|---|
| Example 10 | Bio-electrode composition solution 10 | 2.8 | 650 | $6.2E^4$ | $6.3E^4$ |
| Example 11 | Bio-electrode composition solution 11 | 3.1 | 690 | $8.4E^4$ | $8.8E^4$ |
| Example 12 | Bio-electrode composition solution 12 | 3.1 | 670 | $9.9E^4$ | $9.6E^4$ |
| Example 13 | Bio-electrode composition solution 13 | 2.2 | 570 | $5.6E^3$ | $5.5E^3$ |
| Example 14 | Bio-electrode composition solution 14 | 2.6 | 550 | $5.2E^3$ | $6.0E^3$ |
| Example 15 | Bio-electrode composition solution 15 | 2.9 | 500 | $3.2E^3$ | $3.0E^3$ |
| Example 16 | Bio-electrode composition solution 16 | 2.3 | 520 | $2.8E^3$ | $2.2E^3$ |
| Example 17 | Bio-electrode constituent solution 17 | 2.4 | 550 | $2.4E^3$ | $2.5E^3$ |
| Comparative Example 1 | Comparative bio-electrode composition solution 1 | 2.3 | 520 | $4.2E^4$ | $5.3E^5$ |
| Comparative Example 2 | Comparative bio-electrode composition solution 2 | 2.2 | 530 | $5.2E^4$ | $7.3E^5$ |
| Comparative Example 3 | Comparative bio-electrode composition solution 3 | 2.6 | 520 | $5.1E^4$ | $8.3E^5$ |
| Comparative Example 4 | Comparative bio-electrode composition solution 4 | 4.5 | 540 | $9.9E^6$ | $9.9E^6$ |
| Comparative Example 5 | Comparative bio-electrode composition solution 5 | 0 | 430 | $4.9E^5$ | $4.8E^5$ |

As illustrated in Table 3, Examples 1 to 17 showed the living body contact layers formed of the bio-electrode compositions of the present invention including a salt having a specific structure (ionic material) and a resin. The initial impedance was low, and even after the bio-electrode was immersed in water and dried, no significant change in impedance was found. In the bio-electrodes obtained in Examples 1 to 17, the initial conductivity was high, and there were no significant reductions in conductivity even though the bio-electrode was soaked in water or dried. These bio-electrodes in Examples 1 to 17 demonstrate adhesion as favorable as those in Comparative Examples 1 to 3 where conventional salts and resins were blended, are light-weight, excellent in biocompatibility, and can be manufactured at low cost.

Meanwhile, Comparative Examples 1 to 3 showed the living body contact layers formed of the bio-electrode compositions including conventional salts and resins. Although the initial impedance was low, the impedance significantly increased to a higher-digit number after the bio-electrode was immersed in water and dried. The bio-electrodes in Comparative Examples 1 to 3 demonstrated a high initial conductivity, but when they were soaked in water or dried, all the conductivity values significantly declined.

Comparative Example 4 showed the living body contact layer formed of the bio-electrode composition including a resin, instead of a salt. Non-salt content caused no significant higher-digit increase in impedance even after the bio-electrode was immersed in water and dried, but the initial impedance was high. All the bio-electrodes in Comparative Example 4 showed low initial conductivity.

Comparative Example 5 showed the living body contact layer formed of the bio-electrode composition including a salt, instead of a resin. The content of salt, as in the Example, caused no significant higher-digit increase in impedance even after the bio-electrode was immersed in water and dried, but non-adhesive resin content caused no high adhesive strength, thereby generating high impedance (initial impedance) to the skin. Specifically, all the bio-electrodes in Comparative Example 5 showed low initial conductivity.

The above observations found that the bio-electrode for forming a living body contact layer, using the bio-electrode composition of the present invention, is excellent in conductivity, biocompatibility, adhesion to a conductive substrate, and holding force of an ionic material. Such a bio-electrode doesn't significantly decline the conductivity even though the bio-electrode is soaked in water or dried, is light-weight, and can be manufactured at low cost.

While this invention has been described with an emphasis upon preferred embodiments, it will be obvious to those of ordinary skill in the art that variations of the preferred embodiments may be used and that it is intended that the invention may be practiced otherwise than as specifically described herein.

Accordingly, this invention includes all modifications encompassed within the spirit and scope of the invention as defined by the following claims.

EXPLANATIONS OF LETTERS OR NUMERALS 1,1' . . . Bio-electrode, 2 . . . Conductive substrate, 3 . . . Living body contact layer, 4 . . . Ionic polymer (ionic material), 5 . . . Carbon material, 6 . . . Resin, 7 . . . Living body, 8 . . . Aluminum disk, 9 . . . Copper wire.

What is claimed is:

1. A bio-electrode composition comprising an (A) ionic material and a (B) resin other than the ionic material (A), wherein the ionic material (A) comprises both a repeating unit "a" of a lithium salt, a sodium salt, a potassium salt, or an ammonium salt of sulfonamide comprising a partial structure represented by the following general formula (1) and a repeating unit "b" comprising a silicon atom, the general formula (1) being:

$$—R^1—C(=O)—N^-—SO_2—Rf_1M^+ \quad (1)$$

wherein,
R¹ represents a single bond, or a linear, a branched, or a cyclic divalent hydrocarbon group comprising 1 to 40 carbon atoms, which may be substituted by a heteroatom, or mediated by a heteroatom;

Rf₁ represents a linear or a branched alkyl group comprising 1 to 4 carbon atoms or a phenyl group, comprising one or more fluorine atoms or a trifluoromethyl group; and M⁺ represents any of a lithium ion, a sodium ion, a potassium ion, or an ammonium ion.

2. The bio-electrode composition according to claim 1, wherein the ionic material (A) is a polymer comprising repeating units represented by the following general formula (2),

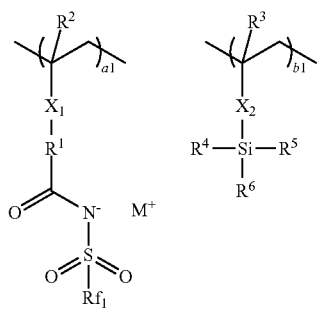

(2)

wherein,
each of R² and R³ independently represents a hydrogen atom or a methyl group;

X₁ represents any of a single bond, a phenylene group, a naphthylene group, an ether group, an ester group, or an amide group;

X₂ represents any of an arylene group comprising 6 to 12 carbon atoms, a —C(=O)—O—R⁷— group, or a —C(=O)—NH—R⁷— group;

R⁷ represents any of a single bond, a linear, a branched, or a cyclic alkylene group comprising 2 to 12 carbon atoms, or a phenylene group, and may include one or more groups selected from an ether group, a carbonyl group, an ester group, and an amide group;

each of R⁴, R⁵, and R⁶ independently represents a linear, a branched, or a cyclic alkyl group comprising 1 to 6 carbon atoms, or an aryl group comprising 6 to 10 carbon atoms, and may include one or more selected from a siloxane bond, a silicon atom, and a halogen atom;

R⁴ and R⁵, or R⁴, R⁵, and R⁶ may be bonded to form a ring or a three-dimensional structure; and "a1" and "b1" are numbers satisfying the equations 0<a1<1.0, 0<b1<1.0.

3. The bio-electrode composition according to claim 2, wherein the polymer comprising the repeating units represented by the general formula (2) further comprises a repeating unit represented by the following general formula (2)',

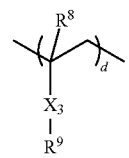

(2)' wherein,
R⁸ represents a hydrogen atom or a methyl group;

X₃ represents any of a single bond, a phenylene group, a naphthylene group, an ether group, an ester group, a phenylene group comprising an ester group, and an amide group;

R⁹ represents a linear or a branched alkyl group comprising 1 to 80 carbon atoms, comprising at least one ether group, and may include an aromatic group; and "d" is a number satisfying the equation 0≤d<1.0.

4. The bio-electrode composition according to claim 3, wherein the M⁺ of the general formula (1) is an ammonium ion represented by the following general formula (3),

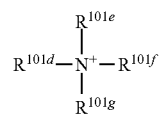

(3)

wherein,
each of $R^{101d}$, $R^{101e}$, $R^{101f}$, and $R^{101g}$ independently represents any of a hydrogen atom, a linear, a branched, or a cyclic alkyl group comprising 1 to 12 carbon atoms, a linear, a branched, or a cyclic alkenyl group or an alkynyl group comprising 2 to 12 carbon atoms, or an aromatic group comprising 4 to 20 carbon atoms, and may include one or more selected from an ether group, a carbonyl group, an ester group, a hydroxy group, an amino group, a nitro group, a sulfonyl group, a sulfinyl group, a halogen atom, and a sulfur atom; and $R^{101d}$ and $R^{101e}$, or $R^{101d}$, $R^{101e}$, and $R^{101f}$ may form a ring together with a nitrogen atom bonded thereto, and in this case, $R^{101d}$ and $R^{101e}$, or $R^{101d}$, $R^{101e}$, and $R^{101f}$ represent an alkylene group comprising 3 to 10 carbon atoms, or form a heteroaromatic ring comprising a nitrogen atom in the formula in the ring.

5. The bio-electrode composition according to claim 2, wherein the M⁺ of the general formula (1) is an ammonium ion represented by the following general formula (3),

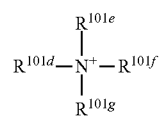

(3)

wherein,
each of $R^{101d}$, $R^{101e}$, $R^{101f}$, and $R^{101g}$ independently represents any of a hydrogen atom, a linear, a branched, or a cyclic alkyl group comprising 1 to 12 carbon atoms, a linear, a branched, or a cyclic alkenyl group or an alkynyl group comprising 2 to 12 carbon atoms, or an aromatic group comprising 4 to 20 carbon atoms, and may include one or more selected from an ether group, a carbonyl group, an ester group, a hydroxy group, an amino group, a nitro group, a sulfonyl group, a sulfinyl group, a halogen atom, and a sulfur atom; and $R^{101d}$ and $R^{101e}$, or $R^{101d}$, $R^{101e}$, and $R^{101f}$ may form a ring together with a nitrogen atom bonded thereto, and in this case, $R^{101d}$ and $R^{101e}$, or $R^{101d}$, $R^{101e}$, and $R^{101f}$ represent an alkylene group comprising 3 to 10 carbon atoms, or form a heteroaromatic ring comprising a nitrogen atom in the formula in the ring.

6. The bio-electrode composition according to claim 1, wherein the ionic material (A) is a polymer comprising the repeating unit "a", the repeating unit "b", and a repeating unit represented by the following general formula (2)',

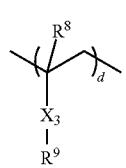

(2)' wherein, $R^8$ represents a hydrogen atom or a methyl group;

$X_3$ represents any of a single bond, a phenylene group, a naphthylene group, an ether group, an ester group, a phenylene group comprising an ester group, and an amide group;

$R^9$ represents a linear or a branched alkyl group comprising 1 to 80 carbon atoms, comprising at least one ether group, and may include an aromatic group; and "d" is a number satisfying the equation $0<d<1.0$.

7. The bio-electrode composition according to claim 6, wherein the $M^+$ of the general formula (1) is an ammonium ion represented by the following general formula (3),

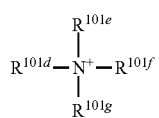

(3)

wherein, each of $R^{101d}$, $R^{101e}$, $R^{101f}$, and $R^{101g}$ independently represents any of a hydrogen atom, a linear, a branched, or a cyclic alkyl group comprising 1 to 12 carbon atoms, a linear, a branched, or a cyclic alkenyl group or an alkynyl group comprising 2 to 12 carbon atoms, or an aromatic group comprising 4 to 20 carbon atoms, and may include one or more selected from an ether group, a carbonyl group, an ester group, a hydroxy group, an amino group, a nitro group, a sulfonyl group, a sulfinyl group, a halogen atom, and a sulfur atom; and $R^{101d}$ and $R^{101e}$, or $R^{101d}$, $R^{101e}$, and $R^{101f}$ may form a ring together with a nitrogen atom bonded thereto, and in this case, $R^{101d}$ and $R^{101e}$, or $R^{101d}$, $R^{101e}$, and $R^{101f}$ represent an alkylene group comprising 3 to 10 carbon atoms, or form a heteroaromatic ring comprising a nitrogen atom in the formula in the ring.

8. The bio-electrode composition according to claim 1, wherein the $M^+$ of the general formula (1) is an ammonium ion represented by the following general formula (3),

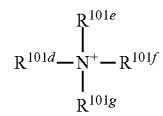

(3)

wherein, each of $R^{101d}$, $R^{101e}$, $R^{101f}$, and $R^{101g}$ independently represents any of a hydrogen atom, a linear, a branched, or a cyclic alkyl group comprising 1 to 12 carbon atoms, a linear, a branched, or a cyclic alkenyl group or an alkynyl group comprising 2 to 12 carbon atoms, or an aromatic group comprising 4 to 20 carbon atoms, and may include one or more selected from an ether group, a carbonyl group, an ester group, a hydroxy group, an amino group, a nitro group, a sulfonyl group, a sulfinyl group, a halogen atom, and a sulfur atom; and $R^{101d}$ and $R^{101e}$, or $R^{101d}$, $R^{101e}$, and $R^{101f}$ may form a ring together with a nitrogen atom bonded thereto, and in this case, $R^{101d}$ and $R^{101e}$, or $R^{101d}$, $R^{101e}$, and $R^{101f}$ represent an alkylene group comprising 3 to 10 carbon atoms, or form a heteroaromatic ring comprising a nitrogen atom in the formula in the ring.

9. The bio-electrode composition according to claim 1, wherein the resin (B) comprises a silicone resin;

diorganosiloxane; and organohydrogen polysiloxane; wherein the silicon resin comprises both a $R_xSiO_{(4-x)/2}$ unit, wherein R represents a substituted or an unsubstituted monovalent hydrocarbon group comprising 1 to 10 carbon atoms, and "x" represents a number of 2.5 to 3.5, and a $SiO_2$ unit;

the diorganosiloxane comprises an alkenyl group; and the organohydrogen polysiloxane comprises a SiH group.

10. The bio-electrode composition according to claim 1, further comprising an organic solvent.

11. The bio-electrode composition according to claim 1, further comprising a carbon material.

12. The bio-electrode composition according to claim 11, wherein the carbon material is formed of carbon black and/or carbon nanotube.

13. A polymer comprising repeating units represented by the following general formula (2),

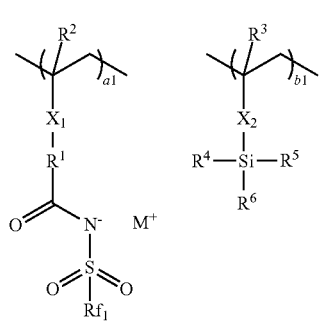

(2)

wherein, $R^1$ represents a single bond, or a linear, a branched, or a cyclic divalent hydrocarbon group comprising 1 to 40 carbon atoms, which may be substituted by a heteroatom, or mediated by a heteroatom;

$Rf_1$ represents a linear or a branched alkyl group comprising 1 to 4 carbon atoms or a phenyl group comprising one or more fluorine atoms or a trifluoromethyl group;

$M^+$ represents any of a lithium ion, a sodium ion, a potassium ion, or an ammonium ion;

each of $R^2$ and $R^3$ independently represents a hydrogen atom or a methyl group;

$X_1$ represents any of a single bond, a phenylene group, a naphthylene group, an ether group, an ester group, or an amide group;

$X_2$ represents any of an arylene group comprising 6 to 12 carbon atoms, a —C(=O)—O—$R^7$— group, or a —C(=O)—NH—$R^7$— group;

$R^7$ represents any of a single bond, a linear, a branched, or a cyclic alkylene group comprising 2 to 12 carbon atoms, or a phenylene group and may include one or more groups selected from an ether group, a carbonyl group, an ester group, and an amide group;

each of $R^4$, $R^5$, and $R^6$ independently represents a linear, a branched, or a cyclic alkyl group comprising 1 to 6 carbon atoms, or an aryl group comprising 6 to 10 carbon atoms, and may include one or more selected from a siloxane bond, a silicon atom, and a halogen atom;

$R^4$ and $R^5$, or $R^4$, $R^5$, and $R^6$ may be bonded to form a ring or a three-dimensional structure; and "a1" and "b1" are numbers satisfying the equations $0<a1<1.0$, $0<b1<1.0$.

14. The polymer according to claim 13, the polymer further comprising a repeating unit represented by the following general formula (2)',

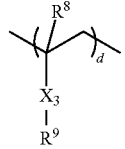

(2)' wherein, $R^8$ represents a hydrogen atom or a methyl group;

$X_3$ represents any of a single bond, a phenylene group, a naphthylene group, an ether group, an ester group, a phenylene group comprising an ester group, or an amide group;

$R^9$ represents a linear, or a branched alkyl group comprising 1 to 80 carbon atoms, comprising at least one ether group, and may include an aromatic group; and "d" is a number satisfying the equation $0 \leq d < 1.0$.

* * * * *